United States Patent
Coates et al.

(10) Patent No.: US 11,124,500 B2
(45) Date of Patent: Sep. 21, 2021

(54) DISUBSTITUTED PYRAZOLE COMPOUNDS

(71) Applicant: Eli Lilly and Company, Indianapolis, IN (US)

(72) Inventors: David Andrew Coates, New Palestine, IN (US); Timothy Barrett Durham, Indianapolis, IN (US); Richard Duane Johnston, Greenfield, IN (US); Steven Marc Massey, Indianapolis, IN (US); Patrick Gianpietro Spinazze, Avon, IN (US); Douglas Richard Stack, Fishers, IN (US); James Lee Toth, Knightstown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/902,806

(22) Filed: Jun. 16, 2020

(65) Prior Publication Data
US 2020/0392118 A1 Dec. 17, 2020

Related U.S. Application Data

(60) Provisional application No. 62/975,887, filed on Feb. 13, 2020, provisional application No. 62/862,382, filed on Jun. 17, 2019.

(51) Int. Cl.
| | |
|---|---|
| *C07D 403/14* | (2006.01) |
| *A61P 1/16* | (2006.01) |
| *A61P 3/10* | (2006.01) |
| *A61P 13/12* | (2006.01) |
| *A61P 9/04* | (2006.01) |

(52) U.S. Cl.
CPC .............. *C07D 403/14* (2013.01); *A61P 1/16* (2018.01); *A61P 3/10* (2018.01); *A61P 9/04* (2018.01); *A61P 13/12* (2018.01)

(58) Field of Classification Search
CPC .................................................. C07D 403/14
See application file for complete search history.

(56) References Cited

U.S. PATENT DOCUMENTS

| | | |
|---|---|---|
| 2011/0015395 A1 | 1/2011 | Lee et al. |
| 2017/0183328 A1 | 6/2017 | Dowling et al. |

FOREIGN PATENT DOCUMENTS

| | | |
|---|---|---|
| WO | 2017075367 | 5/2017 |

OTHER PUBLICATIONS

International Search Report of the International Searching Authority pertaining to International Application No. PCT/US2020/037894; dated Sep. 24, 2020; 5 pages.
Written Opinion of the International Searching Authority pertaining to International Application No. PCT/US2020/037894; dated Sep. 24, 2020; 12 pages.
J. Hepatology. EASL International Liver Congress Abstracts, Supplement N°1S vol. 70, (Apr. 2019).
Cirillo, P., Gersch, M. S., Mu, W., Scherer, P. M., Kim, K. M., Gesualdo, L., . . . & Sautin, Y. Y. (2009). Ketohexokinase-dependent metabolism of fructose induces proinflammatory mediators in proximal tubular cells. Journal of the American Society of Nephrology, 20(3), 545-553.
Maryanoff, B. E., O'Neill, J. C., McComsey, D. F., Yabut, S. C., Luci, D. K., Jordan Jr, A. D., . . . & Petrounia, I. (2011). Inhibitors of ketohexokinase: discovery of pyrimidinopyrimidines with specific substitution that complements the ATP-binding site. *ACS medicinal chemistry letters*, 2(7), 538-543.
Ishimoto, T., Lanaspa, M. A., Le, M. T., Garcia, G. E., Diggle, C. P., MacLean, P. S., . . . & Rivard, C. J. (2012). Opposing effects of fructokinase C and A isoforms on fructose-induced metabolic syndrome in mice. Proceedings of the National Academy of Sciences, 109(11), 4320-4325.
Vos, M. B., & Lavine, J. E. (2013). Dietary fructose in nonalcoholic fatty liver disease. Hepatology, 57(6), 2525-2531.
Huard, K, Ahn, K., Amor, P., Beebe, D. A., Borzilleri, K. A., Chrunyk, B. A., . . . & Dowling, M. S. (2017). Discovery of fragment-derived small molecules for in vivo inhibition of ketohexokinase (KHK). *Journal o medicinal chemistry*, 60(18), 7835-7849.
Softie, S., Gupta, M. K., Wang, G. X., Fujisaka, S., O'neill, B. T., Rao, I. N., . . . & Newgard, C. B. (2017). Divergent effects of glucose and fructose on hepatic lipogenesis and insulin signaling. *The Journal of clinical investigation*, 127(11), 4059-4074.

(Continued)

*Primary Examiner* — Brian E McDowell
(74) *Attorney, Agent, or Firm* — Macharri R. Vorndran-Jones

(57) ABSTRACT

The present invention provides a compound of Formula I

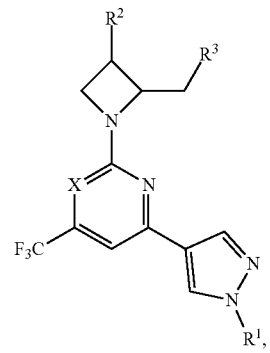

or a pharmaceutically acceptable salt thereof, and the use of compounds of Formula I for treating metabolic conditions, such as type 2 diabetes mellitus, heart failure, diabetic kidney disease, and non-alcoholic steatohepatitis.

17 Claims, No Drawings

(56) References Cited

OTHER PUBLICATIONS

Mirtschink, P., Jang, C., Arany, Z., Krek, W., (2018). Fructose metabolism, cardiometabolic risk, and the epidemic of coronary artery disease, European Heart Journal, vol. 39, Issue 26, Jul. 7, 2018, pp. 2497-2505.

Hannou, S.A., et al., "Fructose Metabolism and Metabolic Disease," *J. Clin. Invest.*, (2018), 128(2), 544-555.

DISUBSTITUTED PYRAZOLE COMPOUNDS

The present invention relates to novel ketohexokinase (KHK) inhibitor compounds, to pharmaceutical compositions comprising the compounds and to the use of the compounds for the treatment of certain conditions, such as type 2 diabetes mellitus (T2DM), heart failure, diabetic kidney disease and non-alcoholic steatohepatitis (NASH).

KHK, also referred to as fructokinase, is the rate-limiting enzyme involved in fructose metabolism. It catalyses the phosphorylation of fructose to fructose-1-phosphate (F1P), causing concomitant depletion of cellular ATP levels. In contrast to glucose, fructose metabolism lacks feedback inhibition and it triggers accumulation of downstream intermediates involved in, for example, lipogenesis, gluconeogenesis and oxidative phosphorylation (Hannou, S. A., et al.; *J. Cin. Invest.*, 128(2), 544-555, 2018). This has negative metabolic consequences which are associated with a number of serious metabolic disorders.

KHK exists in two alternatively spliced isoforms consisting of KHK-C and KHK-A differing in exon 3. KHK-C is expressed primarily in the liver, kidney and intestine, whereas KHK-A is more ubiquitous. Mice deficient in both isoforms are fully protected from fructose-induced metabolic syndrome. However, the adverse metabolic effects are exacerbated in mice lacking KHK-A only (Ishimoto T, et al.; *Proc. Natl. Acad. Sci. USA*, 109(11), 4320-4325, 2012).

Several epidemiologic and experimental studies have reported that increased consumption of fructose, and more precisely increased fructose metabolism, may play an important role in the development of certain disorders, including metabolic syndrome and in particular, in the development of T2DM (Softic et al.; *J. Cin. Invest.*, 127(11), 4059-4074, 2017), heart failure (Mirtschink, P., et al.; *Eur. Heart J.*, 39, 2497-2505, 2018), diabetic kidney disease (Cirillo, P., et al.; *J. Am. Soc. Nephrol.*, 20, 545-553, 2009) and NAFLD/NASH (Vos, M. B., et al.; *Hepatology*, 57, 2525-2531, 2013). Targeting inhibition of KHK is expected to limit fructose metabolism and provide effective treatment options for a number of metabolic disorders.

US 2017/0183328 A1 discloses substituted 3-azabicyclo [3.1.0]hexanes as KHK inhibitors. Recently published data shows that ketohexokinase inhibitor PF-06835919 administered for 6 weeks reduces whole liver fat as measured by magnetic resonance imaging-proton density fat fraction in subjects with non-alcoholic fatty liver disease (*J. Hepatology.* EASL International Liver Congress Abstracts, Supplement No 1S Vol. 70, April 2019).

Compounds containing carboxylic functional groups carry a risk associated with the formation of acyl glucuronide metabolites (Vleet Van et al., *Toxicology Letters*, 272 (2017) 1-7). Acyl glucuronide metabolites are often unstable and may be chemically reactive leading to covalent bonding with macromolecules and toxicity.

There is a need for alternate treatments for metabolic syndrome and associated indications including T2DM, heart failure, diabetic kidney disease and NASH. In particular, there is a need for compounds which are potent inhibitors of KHK. There is a need for KHK inhibitor compounds having advantageous properties, for example, good oral bioavailability to support once daily dosing. Furthermore, there is a need for KHK inhibitor compounds which do not have a carboxylic acid moiety and lack the ability to form acyl glucuronides.

Accordingly, in one embodiment, the present invention provides a compound of the Formula I:

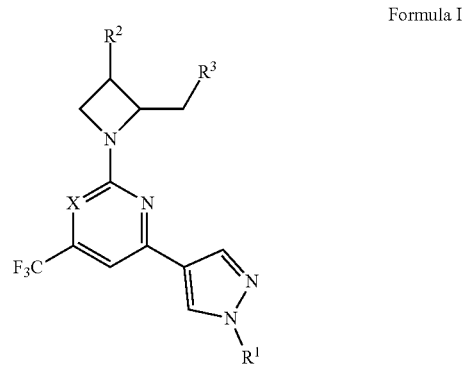

Formula I wherein
X is N, or C substituted with CN;
$R^1$ is selected from: H,

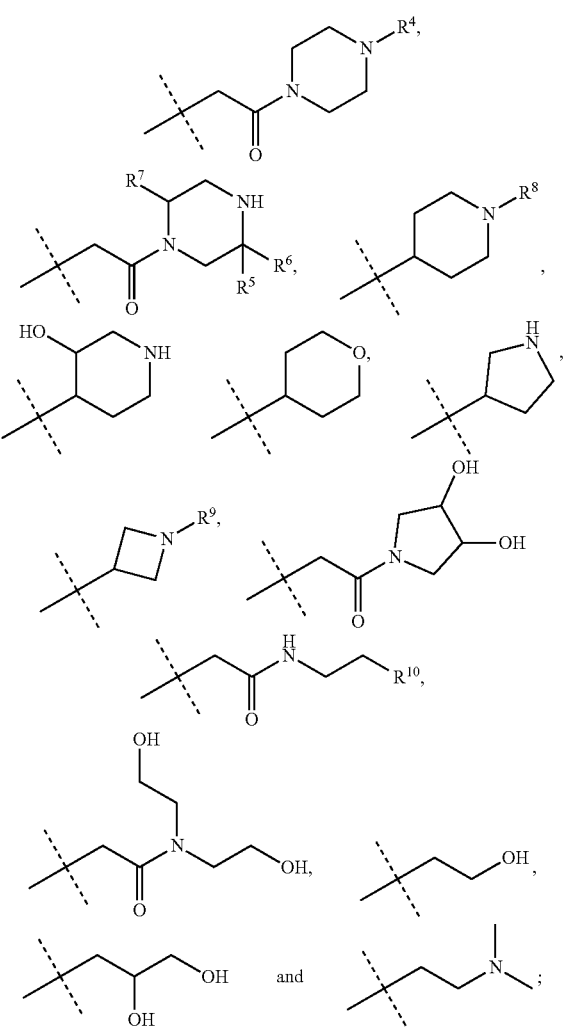

$R^2$ and $R^3$ are both H, or one is H and the other is OH;
$R^4$, $R^5$, $R^6$, $R^7$ and $R^9$ are independently H or $CH_3$;

$R^8$ is H, $CH_3$, $CH_2CH_2OH$, $C(=O)CH_2NH_2$, or $C(=O)CH_3$; and $R^{10}$ is OH or $NH_2$;

or a pharmaceutically acceptable salt thereof.

In a particular embodiment, $R^1$ is selected from: H,

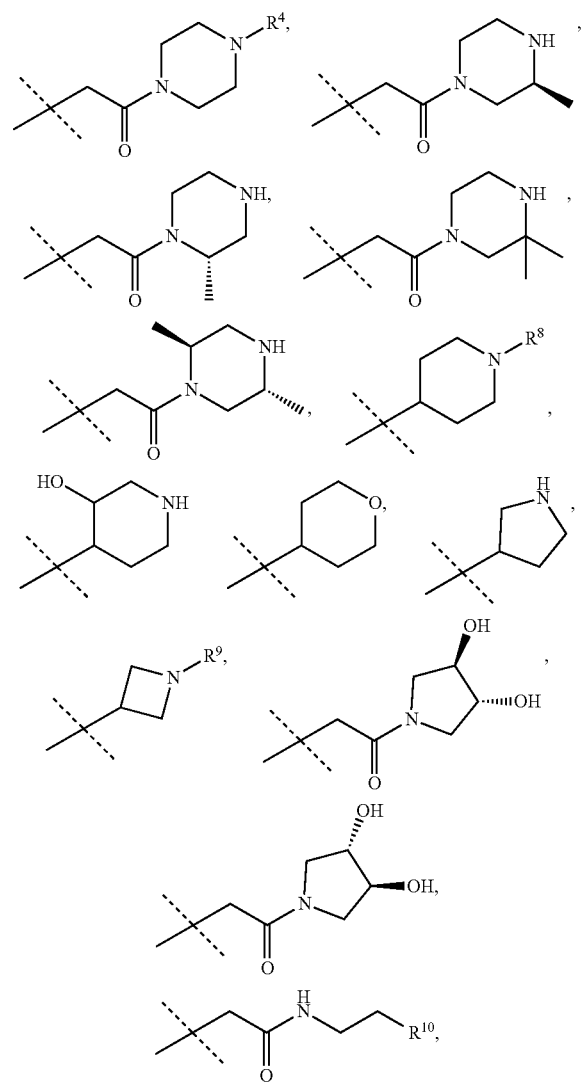

or a pharmaceutically acceptable salt thereof.

In a particular embodiment, there is provided a compound of Formula I wherein X is N or C substituted with CN;

$R^1$ is selected from:

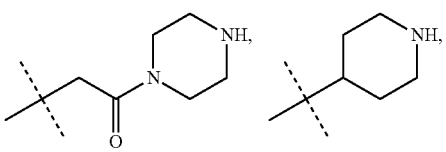

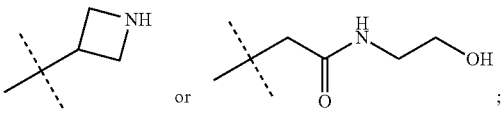

and wherein $R^2$ is H and $R^3$ is OH, or $R^2$ is OH and $R^3$ is H, or $R^2$ and $R^3$ are both H;

or a pharmaceutically acceptable salt thereof.

In a particular embodiment, the compound is of Formula Ia:

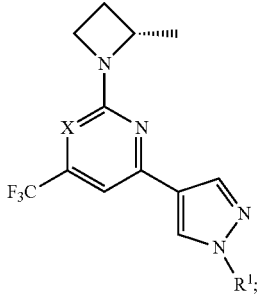

Formula Ia or a pharmaceutically acceptable salt thereof.

In a particular embodiment, the compound is of Formula Ic:

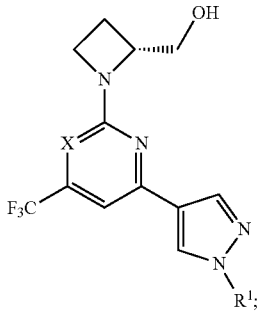

Formula Ic or a pharmaceutically acceptable salt thereof.

In a particular embodiment, the compound is of Formula Ie:

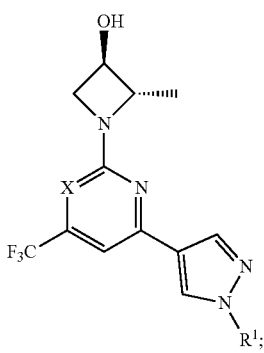

Formula Ie or a pharmaceutically acceptable salt thereof.

In an embodiment, X is N.

In an embodiment, X is C substituted with CN.

In an embodiment, R¹ is

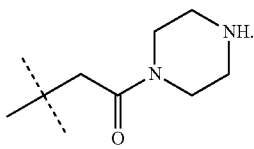

In an embodiment, the compound of Formula I is:

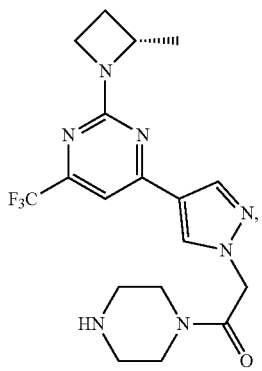 [SMILES: C[C@H]1CCN1c1nc(-c2cnn(CC(=O)N3CCNCC3)c2)cc(C(F)(F)F)n1]

or a pharmaceutically acceptable salt thereof.

In a particular embodiment, there is provided a succinate salt of

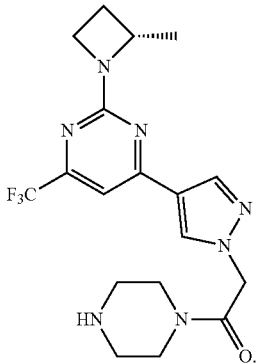 [SMILES: C[C@H]1CCN1c1nc(-c2cnn(CC(=O)N3CCNCC3)c2)cc(C(F)(F)F)n1]

In a preferred embodiment, the succinate salt is the sesquisuccinate salt.

In an embodiment, the compound of Formula I is:

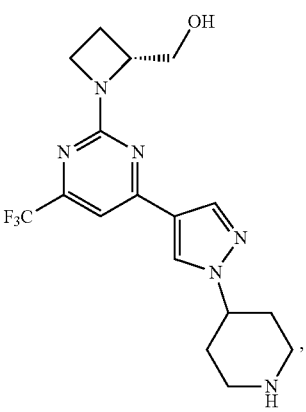 [SMILES: OC[C@H]1CCN1c1nc(-c2cnn(C3CCNCC3)c2)cc(C(F)(F)F)n1]

or a pharmaceutically acceptable salt thereof.

In an embodiment, the compound of Formula I is:

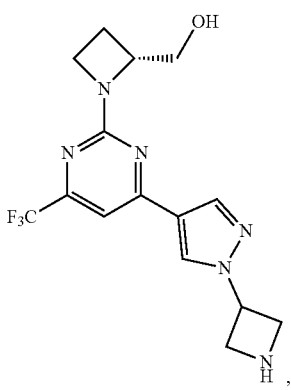 [SMILES: OC[C@H]1CCN1c1nc(-c2cnn(C3CNC3)c2)cc(C(F)(F)F)n1]

or a pharmaceutically acceptable salt thereof.

In an embodiment, the compound of Formula I is:

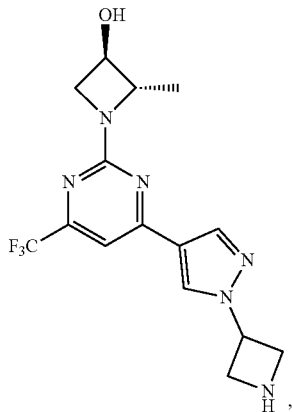 [SMILES: C[C@H]1[C@H](O)CN1c1nc(-c2cnn(C3CNC3)c2)cc(C(F)(F)F)n1]

or a pharmaceutically acceptable salt thereof.

In an embodiment, the compound of Formula I is:

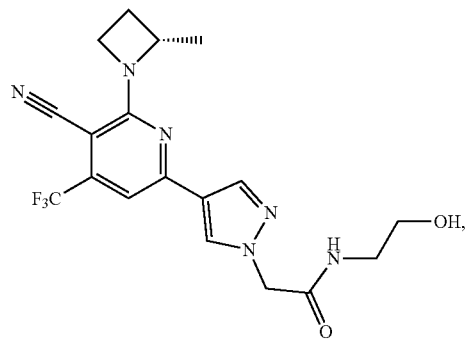 [SMILES: C[C@H]1CCN1c1nc(-c2cnn(CC(=O)NCCO)c2)cc(C(F)(F)F)c1C#N]

or a pharmaceutically acceptable salt thereof.

In an embodiment, the compound of Formula I is:

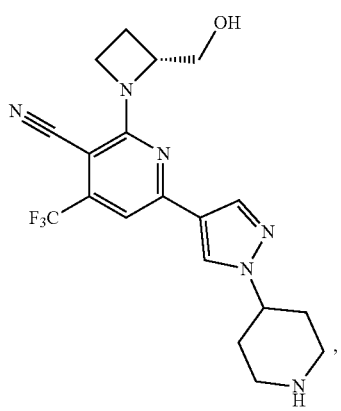 [SMILES: N#Cc1c(C(F)(F)F)cc(-c2cnn(C3CCNCC3)c2)nc1N1CC[C@@H]1CO]

or a pharmaceutically acceptable salt thereof.

In an embodiment, the compound of Formula I is:

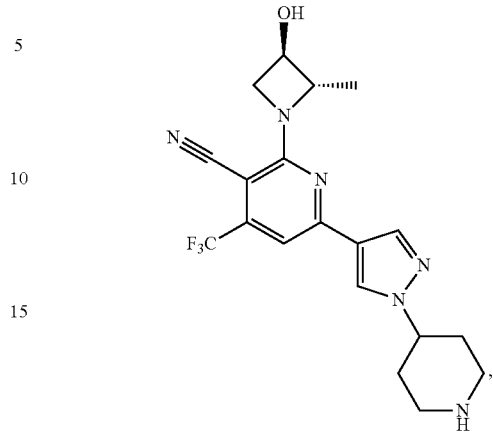

or a pharmaceutically acceptable salt thereof.

In a particular embodiment, the compound is selected from:

2-[4-[2-[(2S)-2-methylazetidin-1-yl]-6-(trifluoromethyl)pyrimidin-4-yl]pyrazol-1-yl]-1-piperazin-1-yl-ethanone;

[(2R)-1-[4-[1-(4-piperidyl)pyrazol-4-yl]-6-(trifluoromethyl)pyrimidin-2-yl]azetidin-2-yl]methanol;

[(2R)-1-[4-[1-(azetidin-3-yl)pyrazol-4-yl]-6-(trifluoromethyl)pyrimidin-2-yl]azetidin-2-yl]methanol;

(2S,3R)-1-[4-[1-(azetidin-3-yl)pyrazol-4-yl]-6-(trifluoromethyl)pyrimidin-2-yl]-2-methyl-azetidin-3-ol;

2-[4-[5-cyano-6-[(2S)-2-methylazetidin-1-yl]-4-(trifluoromethyl)-2-pyridyl]pyrazol-1-yl]-N-(2-hydroxyethyl)acetamide;

2-[(2R)-2-(hydroxymethyl)azetidin-1-yl]-6-[1-(4-piperidyl)pyrazol-4-yl]-4-(trifluoromethyl)pyridine-3-carbonitrile;

2-[(2S,3R)-3-hydroxy-2-methyl-azetidin-1-yl]-6-[1-(4-piperidyl)pyrazol-4-yl]-4-(trifluoromethyl)pyridine-3-carbonitrile;

2-[(2S)-2-methylazetidin-1-yl]-6-[1-(1-methyl-4-piperidyl)pyrazol-4-yl]-4-(trifluoromethyl)pyridine-3-carbonitrile;

6-[1-[1-(2-hydroxyethyl)-4-piperidyl]pyrazol-4-yl]-2-[(2S)-2-methylazetidin-1-yl]-4-(trifluoromethyl)pyridine-3-carbonitrile;

6-[1-[2-(dimethylamino)ethyl]pyrazol-4-yl]-2-[(2S)-2-methylazetidin-1-yl]-4-(trifluoromethyl)pyridine-3-carbonitrile;

6-[1-(2-hydroxyethyl)pyrazol-4-yl]-2-[(2S)-2-methylazetidin-1-yl]-4-(trifluoromethyl)pyridine-3-carbonitrile;

2-[(2S)-2-methylazetidin-1-yl]-6-[1-(4-piperidyl)pyrazol-4-yl]-4-(trifluoromethyl)pyridine-3-carbonitrile;

2-[(2S)-2-methylazetidin-1-yl]-4-[1-(4-piperidyl)pyrazol-4-yl]-6-(trifluoromethyl)pyrimidine;

(2S,3R)-2-methyl-1-[4-[1-[(3R)-pyrrolidin-3-yl]pyrazol-4-yl]-6-(trifluoromethyl)pyrimidin-2-yl]azetidin-3-ol;

(2S,3R)-2-methyl-1-[4-[1-[(3S)-pyrrolidin-3-yl]pyrazol-4-yl]-6-(trifluoromethyl)pyrimidin-2-yl]azetidin-3-ol;

[(2R)-1-[4-[1-[(3R)-pyrrolidin-3-yl]pyrazol-4-yl]-6-(trifluoromethyl)pyrimidin-2-yl]azetidin-2-yl]methanol;

6-[1-(azetidin-3-yl)pyrazol-4-yl]-2-[(2S)-2-methylazetidin-1-yl]-4-(trifluoromethyl)pyridine-3-carbonitrile;

6-[1-[1-(2-aminoacetyl)-4-piperidyl]pyrazol-4-yl]-2-[(2S)-2-methylazetidin-1-yl]-4-(trifluoromethyl)pyridine-3-carbonitrile;

6-[1-(1-acetyl-4-piperidyl)pyrazol-4-yl]-2-[(2S)-2-methylazetidin-1-yl]-4-(trifluoromethyl)pyridine-3-carbonitrile;

2-[(2S)-2-methylazetidin-1-yl]-6-[1-[2-(4-methylpiperazin-1-yl)-2-oxo-ethyl]pyrazol-4-yl]-4-(trifluoromethyl)pyridine-3-carbonitrile;

2-[4-[5-cyano-6-[(2S)-2-methylazetidin-1-yl]-4-(trifluoromethyl)-2-pyridyl]pyrazol-1-yl]-N,N-bis(2-hydroxyethyl)acetamide;

6-[1-[2-[(3R,4R)-3,4-dihydroxypyrrolidin-1-yl]-2-oxo-ethyl]pyrazol-4-yl]-2-[(2S)-2-methylazetidin-1-yl]-4-(trifluoromethyl)pyridine-3-carbonitrile;

6-[1-[2-[(3S,4S)-3,4-dihydroxypyrrolidin-1-yl]-2-oxo-ethyl]pyrazol-4-yl]-2-[(2S)-2-methylazetidin-1-yl]-4-(trifluoromethyl)pyridine-3-carbonitrile;

6-[1-(2,3-dihydroxypropyl)pyrazol-4-yl]-2-[(2S)-2-methylazetidin-1-yl]-4-(trifluoromethyl)pyridine-3-carbonitrile;

2-[(2S)-2-methylazetidin-1-yl]-6-(1H-pyrazol-4-yl)-4-(trifluoromethyl)pyridine-3-carbonitrile;

2-[(2S)-2-methylazetidin-1-yl]-6-(1-tetrahydropyran-4-ylpyrazol-4-yl)-4-(trifluoromethyl)pyridine-3-carbonitrile;

6-[1-(3-hydroxy-4-piperidyl)pyrazol-4-yl]-2-[(2S)-2-methylazetidin-1-yl]-4-(trifluoromethyl)pyridine-3-carbonitrile;

N-(2-aminoethyl)-2-[4-[2-[(2S)-2-methylazetidin-1-yl]-6-(trifluoromethyl)pyrimidin-4-yl]pyrazol-1-yl]acetamide;

2-[4-[2-[(2S)-2-methylazetidin-1-yl]-6-(trifluoromethyl)pyrimidin-4-yl]pyrazol-1-yl]-1-[(3S)-3-methylpiperazin-1-yl]ethanone;

2-[4-[2-[(2S)-2-methylazetidin-1-yl]-6-(trifluoromethyl)pyrimidin-4-yl]pyrazol-1-yl]-1-[(2S)-2-methylpiperazin-1-yl]ethanone;

1-(3,3-dimethylpiperazin-1-yl)-2-[4-[2-[(2S)-2-methylazetidin-1-yl]-6-(trifluoromethyl)pyrimidin-4-yl]pyrazol-1-yl]ethanone;

1-[(2S,5R)-2,5-dimethylpiperazin-1-yl]-2-[4-[2-[(2S)-2-methylazetidin-1-yl]-6-(trifluoromethyl)pyrimidin-4-yl]pyrazol-1-yl]ethanone;

4-[1-(azetidin-3-yl)pyrazol-4-yl]-2-[(2S)-2-methylazetidin-1-yl]-6-(trifluoromethyl)pyrimidine;

2-[(2S)-2-methylazetidin-1-yl]-4-[1-(1-methylazetidin-3-yl)pyrazol-4-yl]-6-(trifluoromethyl)pyrimidine;

(2S,3R)-2-methyl-1-[4-[1-(1-methylazetidin-3-yl)pyrazol-4-yl]-6-(trifluoromethyl)pyrimidin-2-yl]azetidin-3-ol; or

[(2R)-1-[4-[1-(1-methylazetidin-3-yl)pyrazol-4-yl]-6-(trifluoromethyl)pyrimidin-2-yl]azetidin-2-yl]methanol;

or a pharmaceutically acceptable salt thereof.

In a particular embodiment, the compound is 2-[4-[2-[(2S)-2-Methylazetidin-1-yl]-6-(trifluoromethyl)pyrimidin-4-yl]pyrazol-1-yl]-1-piperazin-1-yl-ethanone sesquisuccinate, which is also known as ethanone, 2-[4-[2-[(2S)-2-methyl-1-azetidinyl]-6-(trifluoromethyl)-4-pyrimidinyl]-1H-pyrazol-1-yl]-1-(1-piperazinyl)-, butanedioate (1:1.5) or butanedioic acid-2-(4-{2-[(2S)-2-methylazetidin-1-yl]-6-(trifluoromethyl)pyrimidin-4-yl}-1H-pyrazol-1-yl)-1-(piperazin-1-yl)ethan-1-one (1.5/1).

Formula I encompasses Formulae Ia, Ib, Ic, Id, Ie, If, Ig and Ih and reference to Formula I below, for example in the methods of treatment and therapeutic uses, is also be read as a reference to each and all of these sub-formulae.

In an embodiment, there is provided a method of treating T2DM in a patient in need of such treatment, comprising administering to the patient an effective amount of a compound of Formula I, or a pharmaceutically acceptable salt thereof.

In an embodiment, there is provided a method of treating heart failure in a patient in need of such treatment, comprising administering to the patient an effective amount of a compound of Formula I, or a pharmaceutically acceptable salt thereof.

In an embodiment, there is provided a method of treating diabetic kidney disease in a patient in need of such treatment, comprising administering to the patient an effective amount of a compound of Formula I, or a pharmaceutically acceptable salt thereof.

In an embodiment, there is provided a method of treating NASH in a patient in need of such treatment, comprising administering to the patient an effective amount of a compound of Formula I, or a pharmaceutically acceptable salt thereof.

In an embodiment, there is provided a method of treating a disease selected from the group consisting of metabolic syndrome, NAFLD, obesity, cardiovascular disease, coronary artery disease, chronic kidney disease, dyslipidenia and diabetic complications for example diabetic retinopathy, in a patient in need of such treatment, comprising administering to the patient an effective amount of a compound of Formula I, or a pharmaceutically acceptable salt thereof.

Furthermore, in an embodiment, there is provided a compound of Formula I, or a pharmaceutically acceptable salt thereof, for use in therapy. In an embodiment, there is provided a compound of Formula I, or a pharmaceutically acceptable salt thereof, for use in treating T2DM. In an embodiment, there is provided a compound of Formula I, or a pharmaceutically acceptable salt thereof, for use in treating heart failure. In an embodiment, there is provided a compound of Formula I, or a pharmaceutically acceptable salt thereof, for use in treating diabetic kidney disease. In an embodiment, there is provided a compound of Formula I, or a pharmaceutically acceptable salt thereof, for use in treating NASH. In an embodiment, there is provided a compound of Formula I, or a pharmaceutically acceptable salt thereof, for use in treating metabolic syndrome, NAFLD, obesity, cardiovascular disease, coronary artery disease, chronic kidney disease, dyslipidemia or diabetic complications for example diabetic retinopathy.

Furthermore, in an embodiment, there is provided the use of a compound of Formula I, or a pharmaceutically acceptable salt thereof, for the manufacture of a medicament for treating T2DM. In an embodiment, there is provided the use of a compound of Formula I, or a pharmaceutically acceptable salt thereof, for the manufacture of a medicament for treating heart failure. In an embodiment, there is provided the use of a compound of Formula I, or a pharmaceutically acceptable salt thereof, for the manufacture of a medicament for treating diabetic kidney disease. In an embodiment, there is provided the use of a compound of Formula I, or a pharmaceutically acceptable salt thereof, for the manufacture of a medicament for treating NASH. In an embodiment, there is provided the use of a compound of Formula I, or a pharmaceutically acceptable salt thereof, for the manufacture of a medicament for treating metabolic syndrome, NAFLD, obesity, cardiovascular disease, coronary artery disease, chronic kidney disease, dyslipidemia or diabetic complications for example diabetic retinopathy.

In an embodiment, there is provided a pharmaceutical composition, comprising a compound of Formula I, or a pharmaceutically acceptable salt thereof, with one or more pharmaceutically acceptable carriers, diluents, or excipients. In an embodiment, there is provided a process for preparing a pharmaceutical composition, comprising admixing a compound of Formula I, or a pharmaceutically acceptable salt thereof, with one or more pharmaceutically acceptable carriers, diluents, or excipients.

As used herein, the terms "treating" or "to treat" includes restraining, slowing, stopping, or reversing the progression or severity of an existing symptom or disorder.

As used herein, the term "patient" refers to a mammal. Preferably, the patient is human.

As used herein, the term "effective amount" refers to the amount or dose of compound of Formula I, or a pharmaceutically acceptable salt thereof, which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of Formula I are effective at a dosage per day that falls within the range of about 0.1 to about 15 mg/kg of body weight.

The compounds of Formula I are formulated as pharmaceutical compositions administered by any route which makes the compound bioavailable. Preferably, such compositions are for oral administration. Such pharmaceutical compositions and processes for preparing same are well known in the art (See, e.g., Remington, J. P., "*Remington: The Science and Practice of Pharmacy*", L. V. Allen, Editor, 22$^{nd}$ Edition, Pharmaceutical Press, 2012).

The compounds of Formula I and the pharmaceutically acceptable salts thereof may be used in the methods of treatment and therapeutic uses of the invention, with certain configurations being preferred. It will be understood that the following preferences are applicable both to the treatment methods, the therapeutic uses and to the compounds of the invention.

Compounds of the present invention include:

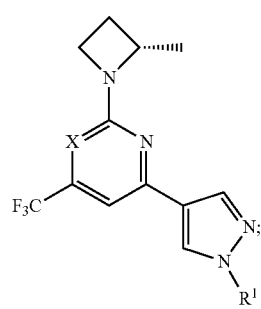

Formula Ia

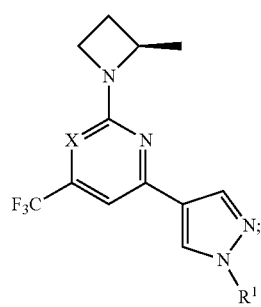

Formula Ib

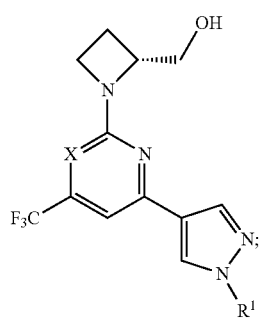

Formula Ic

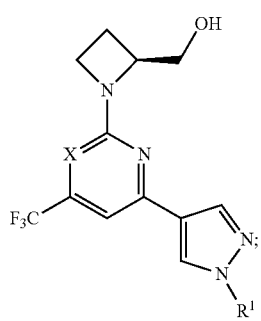

Formula Id

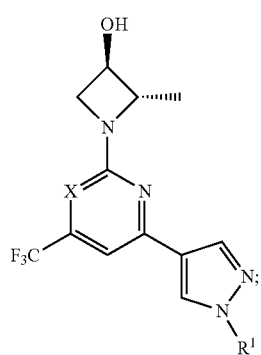

Formula Ie

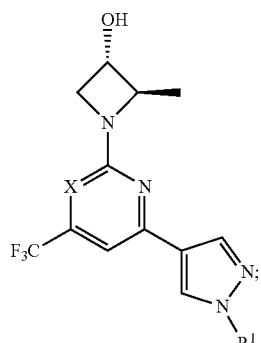

Formula If

13

-continued

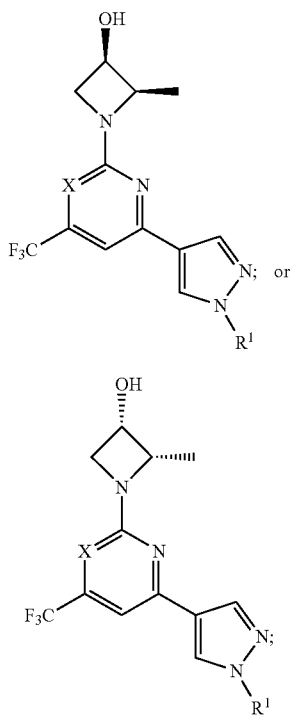

Formula Ig

Formula Ih and pharmaceutically acceptable salts thereof.

Although the present invention contemplates all individual enantiomers and diasteromers, as well as mixtures of said compounds, including racemates, compounds of Formula Ia, Formula Ic and Formula Ie, and pharmaceutically acceptable salts thereof, are particularly preferred.

Individual enantiomers may be separated or resolved by one of ordinary skill in the art at any convenient point in the synthesis of compounds of Formula I, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of Formula I can be formed, for example, by reaction of an appropriate free base of a compound of Formula I and an appropriate pharmaceutically acceptable acid in a suitable solvent under standard conditions well known in the art (See, for example, Bastin, R. J., et al.; *Org. Process. Res. Dev.*, 4, 427-435, 2000 and Berge, S. M., et al.; *J. Pharm. Sci.*, 66, 1-19, 1977). A preferred salt is a succinate salt. A particularly preferred salt is the sesquisuccinate salt. In the sesquisuccinate salt, the ratio of free base:succinate is 1:1.5. The succinate salt is also known as the butanedioate salt.

The compounds of Formula I, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

Without limiting the scope of the invention, the following schemes, preparations, and examples are provided to further illustrate the invention. In addition, one of ordinary skill in the art appreciates that compounds of Formula I may be prepared by using starting material or intermediate with the corresponding desired stereochemical configuration which can be prepared by one of skill in the art.

Certain abbreviations are defined as follows: "ACN" refers to acetonitrile; "BOC" refers to tert-butoxycarbonyl; "DCM" refers to methylene chloride or dichloromethane; "DIPEA" refers to N,N-diisopropylethylamine; "DMF" refers to N,N-dimethylformamide; "DMSO" refers to dimethyl sulfoxide; "ELSD" refers to Evaporative light scattering detector; "ES/MS" refers to Electrospray Mass Spectrometry; "EtOAc" refers to ethyl acetate; "EtOH" refers to ethanol or ethyl alcohol; "h" refers to hour or hours; "HATU" refers to 1-[Bis(dimethyl-amino)methylene]-1H-1,2,3-triazolo[4,5-b]pyridinium 3-oxide hexafluorophosphate; "HPLC" refers to high-performance liquid chromatography; "IPA" refers to isopropyl alcohol; "Me" refers to methyl; "MeOH" refers to methanol; "MTBE" refers to methyl-tert-butyl ether; "min" refers to minute or minutes; "m/z" refers to mass-to-charge ratio; "Ph" refers to phenyl; "RBF" refers to round bottom flask; "RT" refers to room temperature; "SCX" refers to selective cation exchange; "SEM" refers to standard error of the mean; "SFC" refers to supercritical fluid chromatography; "TFA" refers to trifluoroacetic acid; "THF" refers to tetrahydrofuran.

Scheme 1

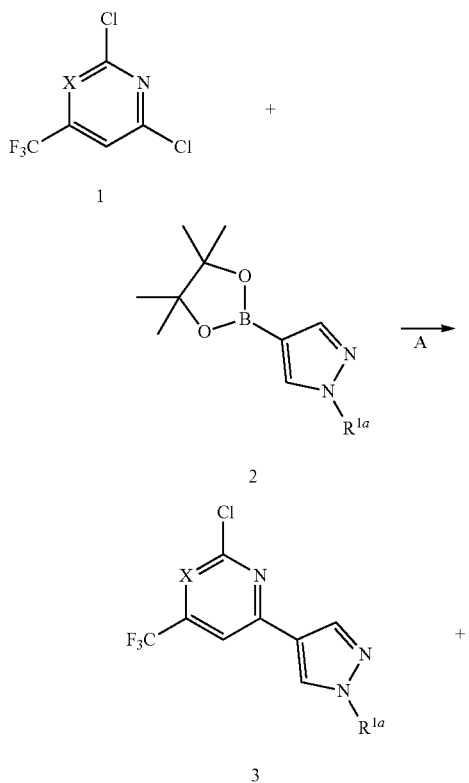

-continued

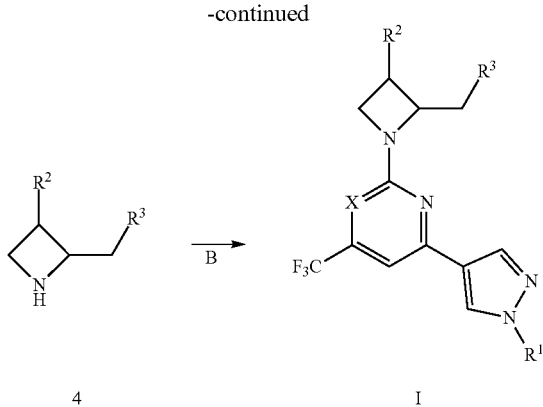

Scheme 1 depicts the general preparation of the compounds of Formula I. $R^{1a}$ may be the same as $R^1$ in the final compound of Formula I or it may be a group requiring transformation to reach $R^1$ of Formula I. The routine synthetic transformations of $R^{1a}$, such as BOC-deprotection, ester hydrolysis and amide coupling reactions may be performed either before or after Step B. In Step A, a Suzuki cross-coupling reaction between heteroaryl dichloride 1 and pyrazole boronate ester 2 yields substituted pyrazole compound 3. This reaction is performed using a base, for example 2 M aqueous $Na_2CO_3$, in an organic solvent, for example 1,4-dioxane, in the presence of a palladium catalyst, such as tetrakis(triphenylphosphine)palladium(0) or bis(triphenylphosphine)palladium(II) dichloride, at elevated temperature. In Step B, compound 3 is subjected to a nucleophilic aromatic substitution reaction with substituted azetidine 4 to give a compound of Formula I. This reaction is performed in the presence of an organic base, such as DIPEA, in an organic solvent, such as 1,4-dioxane, at elevated temperature.

Scheme 2

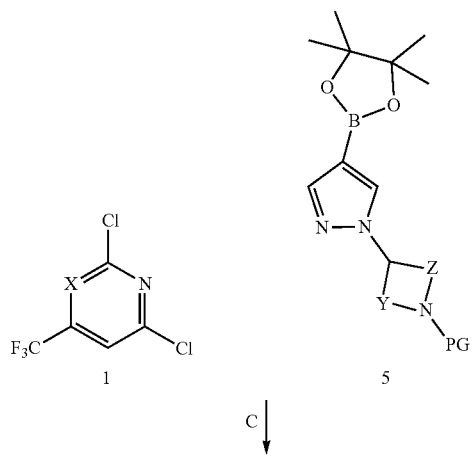

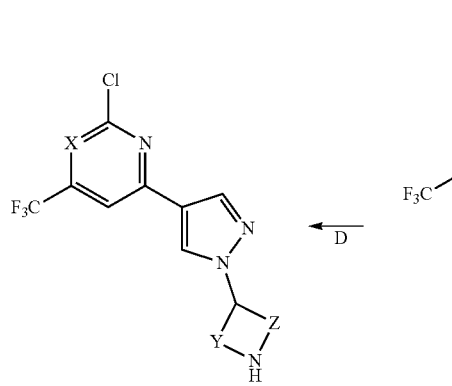

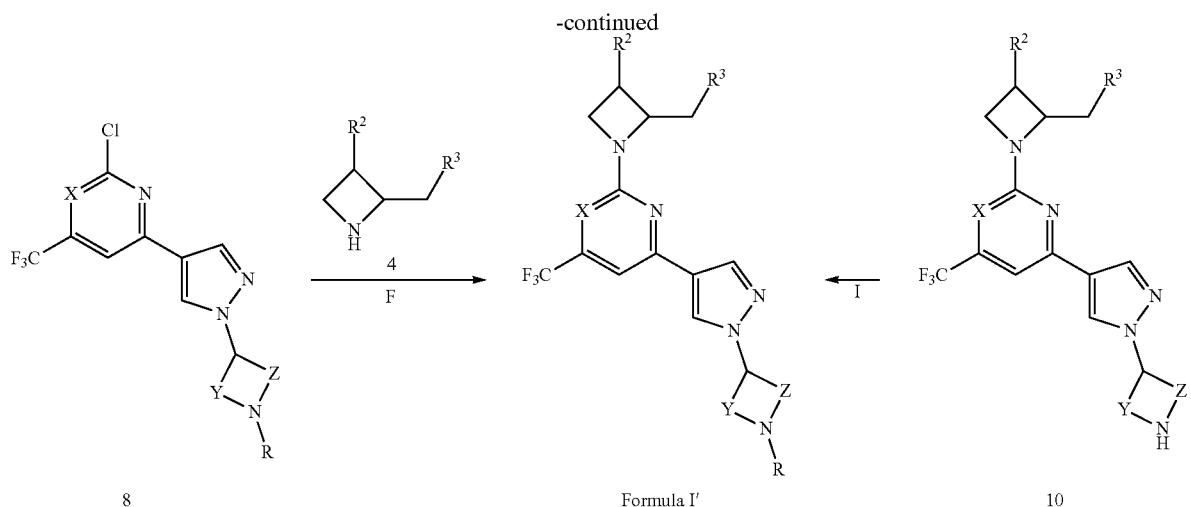

Scheme 2 depicts the preparation of a subset of the compounds of Formula I wherein the pyrazole is substituted with a nitrogen-containing heterocycle (Formula I'). Pyrazole boronate ester 5 is substituted with a nitrogen containing heterocycle as depicted in Scheme 2, wherein "Y" and "Z" may each independently be —CH₂— or —CH₂—CH₂—, and "PG" is a nitrogen protecting group such as BOC. In Step C, a Suzuki cross-coupling reaction between heteroaryl dichloride 1 and pyrazole boronate ester 5 yields substituted pyrazole compound 6. As described in Step A of Scheme 1, this reaction is performed using a base, for example 2 M aqueous Na₂CO₃, in an organic solvent, for example 1,4-dioxane, in the presence of a palladium catalyst, such as tetrakis(triphenylphosphine)palladium(0) or bis(triphenylphosphine)palladium(II) dichloride, at elevated temperature. Two different routes can be taken as depicted in Scheme 2, Route A and Route B.

In Route A, substituted pyrazole compound 6 undergoes deprotection in Step D to give compound 7. For example if "PG" is BOC, deprotection can be accomplished with TFA. In Step E, the heterocyclic nitrogen of compound 7 can undergo substitution reactions, for example reductive amination, acylation, or amide coupling to give compound 8. Such substitutions are depicted as "R" in this scheme. In Step F, compound 8 is subjected to a nucleophilic aromatic substitution reaction with substituted azetidine 4 to give compound of Formula I'. As described in Step B of Scheme 1, this reaction is performed in the presence of an organic base, such as DIPEA, in an organic solvent, such as 1,4-dioxane, at elevated temperature. This may be the final step or alternatively, the R group may be subjected to further routine synthetic transformations such as protecting group removal.

In Route B, substituted pyrazole compound 6 undergoes nucleophilic aromatic substitution reaction in Step G with substituted azetidine 4 to give compound 9. This can be accomplished by nucleophilic aromatic substitution reaction with substituted azetidine 4 in the presence of an organic base, such as DIPEA, in an organic solvent, such as 1,4-dioxane at elevated temperature. Alternatively, Steps C and G can be accomplished in a one-pot procedure, wherein the Suzuki cross-coupling reaction of Step C is completed first, and then azetidine 4 is added to the reaction along with an organic base (e.g. DIPEA), and then Step G proceeds at elevated temperature. Protecting group "PG" is removed in Step H (e.g. with TFA if PG is BOC) to give compound 10. In Step I the nitrogen group of compound 10 can undergo substitution reactions, for example reductive amination, acylation, or amide coupling to give compound of Formula I'. This may be the final step or alternatively, the R group may be subjected to further routine synthetic transformations such as protecting group removal.

Scheme 3

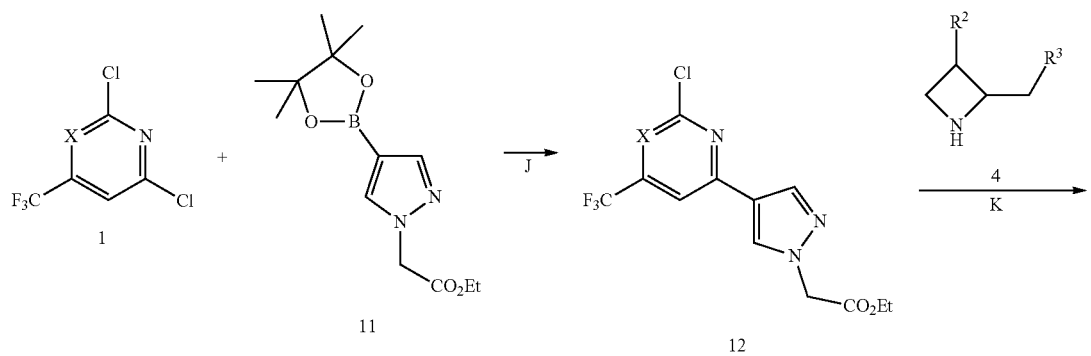

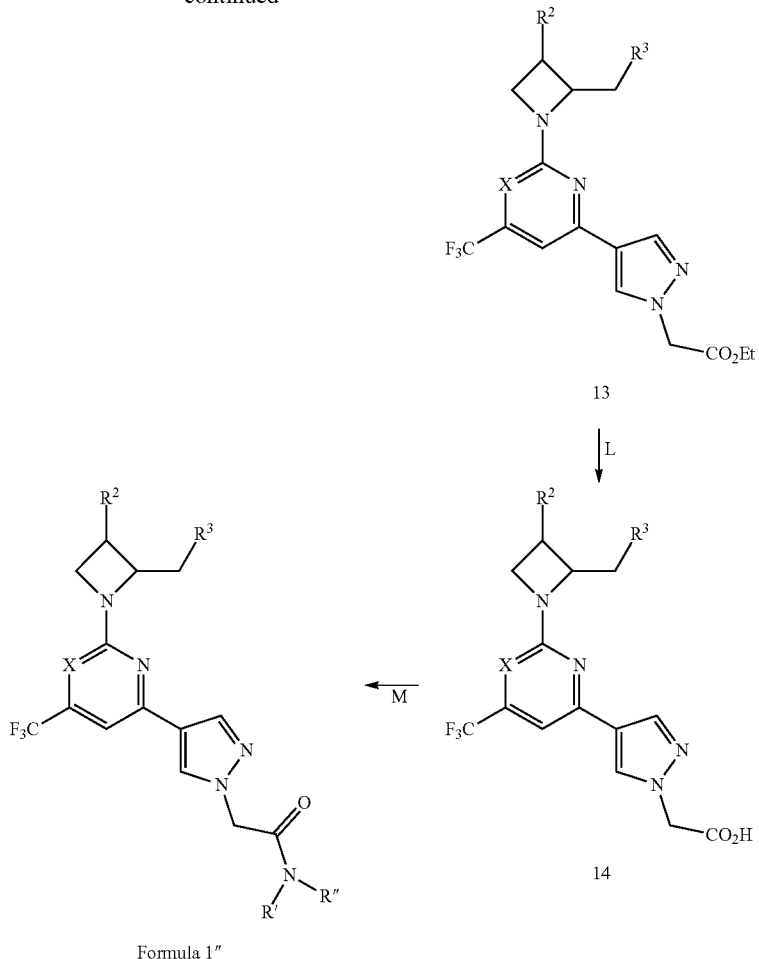

Formula I″

Scheme 3 depicts the preparation of a subset of the compounds of Formula I wherein the pyrazole is substituted with an acetamide group (Formula I″). In Step J, a Suzuki cross-coupling reaction between heteroaryl dichloride 1 and pyrazole boronate ester 11 yields substituted pyrazole compound 12. As described in Schemes 1 and 2, this reaction is performed using a base, for example 2 M aqueous Na$_2$CO$_3$, in an organic solvent, for example 1,4-dioxane, in the presence of a palladium catalyst, such as tetrakis(triphenylphosphine)palladium(0) or bis(triphenylphosphine)palladium(II) dichloride, at elevated temperature. In Step K, heteroaryl chloride 12 undergoes nucleophilic aromatic substitution with azetidine 4 in the presence of an organic base, such as DIPEA, in an organic solvent, such as 1,4-dioxane, at elevated temperature to give compound 13. In Step L, ester hydrolysis using a base e.g. sodium hydroxide gives acid 14. In Step M, acid 14 undergoes amide coupling reaction with an amine of the formula HNR'R″ to give amide compound of Formula I″. The amine HNR'R″ can be cyclic (e.g. an optionally substituted piperazine). Step M may be the final step or there may be further routine synthetic transformations such as protecting group removal.

PREPARATIONS AND EXAMPLES

The following Preparations and Examples further illustrate various embodiments of the invention and represent typical synthesis of the compounds of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1200 liquid chromatography system. Electrospray mass spectrometry measurements (acquired in positive and/or negative mode) are performed on a Mass Selective Detector quadrupole mass spectrometer interfaced to an HPLC which may or may not have an ELSD. LC-MS conditions (low pH): column: PHENOMENEX® GEMINI® NX C18 2.0×50 mm 3.0 μm, 110 Å; gradient: 5-95% B in 1.5 min, then 95% B for 0.5 min column temperature: 50° C.+/−10° C.; flow rate: 1.2 mL/min; 1 μL injection volume; Solvent A: deionized water with 0.1% HCOOH; Solvent B: ACN with 0.1% formic acid; wavelength 200-400 nm and 212-216 nm. If the HPLC is equipped with an ELSD the settings are 45° C. evaporator temperature, 40° C. nebulizer temperature, and 1.6 SLM gas flow rate. Alternate LC-MS conditions (high pH): column: Waters xBridge® C18 column 2.1×50 mm, 3.5 μm; gradient: 5-95% B in 1.5 min, then 95% B for 0.50 min; column temperature: 50° C.+/−10° C.; flow rate: 1.2 mL/min; 1 μL injection volume; Solvent A: 10 mM NH$_4$HCO$_3$ pH 9; Solvent B: ACN; wavelength: 200-400 nm and 212-216 nm; if had ELSD: 45° C. evaporator temp, 40° C. nebulizer temp, and 1.60 SLM gas flow rate.

The XRPD patterns of crystalline solids are obtained on a Bruker D4 Endeavor X-ray powder diffractometer, equipped with a CuKα, source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of 0.2 2θ° is presumed to take into account these potential variations without hindering the unequivocal identification of the indicated crystal form. Confirmation of a crystal form may be made based on any unique combination of distinguishing peaks.

Preparation 1

(2S)-1-Benzhydryl-2-methyl-azetidine [(1R,4S)-7,7-dimethyl-2-oxo-norbornan-1-yl]methanesulfonic Acid Salt

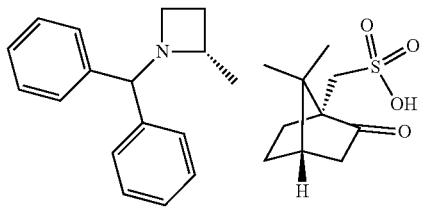

Assemble a 2000 mL 3-neck RBF with an addition funnel, nitrogen inlet and a thermometer adapter. Purge the vessel with nitrogen and add (3R)-butane-1,3-diol (25 g, 277 mmol), DIPEA (127 mL, 731 mmol) and ACN (556 mL). Cool the mixture to -30° C. Add trifluoromethanesulfonic anhydride (101 mL, 601 mmol) dropwise over 3 h such that the internal temperature is maintained between -35 and -30° C. After the completion of the addition, stir for 10 min at -35 to -30° C. Add trifluoromethanesulfonic anhydride (1.9 mL, 11 mmol) dropwise over 5 min such that the internal temperature is maintained between -35 and -30° C. After the completion of the addition, stir for 10 min at -35 to -30° C. Add DIPEA (127 mL, 731 mmol) dropwise over 15 min such that the internal temperature is maintained between -35 and -30° C. After the completion of the addition, stir for 10 min at -35 to -30° C. In a separate flask under nitrogen, dissolve aminodiphenylmethane (48.0 mL, 270 mmol) in ACN (49 mL) and transfer the resulting solution to the addition funnel. Add the amine solution to the cold triflate dropwise over 40 min such that the internal temperature is maintained between -20 to -35° C. After the completion of the addition, stir for 30 min at -35 to -30° C. Transfer the reaction to a water bath and allow it to slowly warm over 30 min. Remove the bath and allow the reaction to warm to RT over 30 min. Transfer the vessel to a heating mantle and warm the reaction to 45° C. for 30 min, then cool to RT. Pour the resulting mixture into 1200 mL of water and extract with toluene (400 mL×3). Combine the extracts and wash with water and saturated aqueous NaCl solution. Dry the organics over anhydrous $Na_2SO_4$, filter and concentrate in vacuo. Dry the residue under vacuum overnight, then dissolve it in DCM (400 mL). Prepare a silica gel pad on a fritted funnel and equilibrate it with 1:1 heptane/EtOAc. Load the product solution onto the silica gel pad and wash with 1600 mL of 1:1 heptane/EtOAc. Concentrate the filtrate to give a red oil. Dissolve the oil in MeOH (250 mL) and place the flask in a water bath (~10° C.). Add L(-)-camphorsulfonic acid (61.6 g, 265 mmol) portion-wise keeping the internal temperature below 20° C. Stir the resulting mixture for 15 min and then concentrate in vacuo to give a brown foam. Dry the foam on a vacuum pump for 2 h. Dissolve the foam in DCM (130 mL), then slowly add EtOAc (1100 mL) to the stirring solution via addition funnel. Transfer the resulting mixture to a 4000 mL beaker and stir open to the atmosphere overnight. Cool the beaker in an ice bath for 10 min. Collect the precipitate in a fritted funnel by vacuum filtration washing with a minimal amount of ice-cold EtOAc. Dry the solid on the frit for 2 h. Dissolve the resulting white solid in a minimal amount of DCM, transfer to a 2000 mL beaker and then dilute slowly with EtOAc until the clear solution starts to become cloudy. Stir the suspension for 4 h while open to the atmosphere. Collect the solids by vacuum filtration using a fritted funnel and dry on the frit overnight to give the title compound (111.8 g, 238.06 mmol, 86% Yield) as a white solid. $^1$H NMR (400 MHz, DMSO-$d_6$) δ 10.54-10.47 (m, 1H), 7.61 (d, J=7.3 Hz, 5H), 7.47-7.37 (m, 7H), 5.85 (d, J=10.3 Hz, 1H), 4.68-4.61 (m, 1H), 3.91-3.83 (m, 2H), 3.37 (s, 8H), 2.99 (d, J=14.6 Hz, 1H), 2.77-2.68 (m, 1H), 2.51-2.44 (m, 4H), 2.30-2.16 (m, 2H), 1.91-1.81 (m, 2H), 1.42-1.28 (m, 3H), 1.08 (s, 3H), 1.01 (d, J=6.6 Hz, 3H), 0.77 (s, 4H); >98% ee [HPLC: Chiralcel® OJ (10 cm×4.6 mm, 5 μm), 5 mL/min, 40° C. isocratic 10% EtOH (0.2% $^i$PrNH$_2$)/CO$_2$].

Preparation 2

[(1R,4S)-7,7-Dimethyl-2-oxo-norbornan-1-yl]methanesulfonate (2S)-2-methylazetidin-1-ium Salt

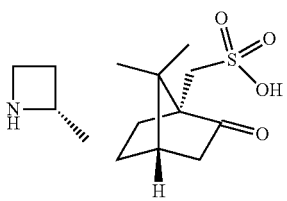

To a 2250 mL Parr vessel add 20 wt % Pd(OH)$_2$ on carbon (6.62 g). Purge the bottle with nitrogen and add MeOH (250 mL). To the resulting suspension, slowly add (2S)-1-benzhydryl-2-methyl-azetidine [(1R,4S)-7,7-dimethyl-2-oxonorbornan-1-yl]methanesulfonic acid salt (111 g, 236 mmol) dissolved in MeOH (250 mL). Seal the vessel. Purge with nitrogen followed by hydrogen and pressurize to 60 PSI. Vigorously shake the reaction vessel in a Parr Shaker apparatus for 15 h at RT. Purge the vessel with nitrogen and then filter the reaction mixture through a pad of Celite, washing with MeOH. Concentrate the filtrate to give a white solid and dry under vacuum. Suspend the solid in 780 mL of 1:1 MTBE/EtOAc and heat the mixture to 65° C. for 20 h then cool to RT and stir overnight. Collect the solids by filtration. Suspend the solids in 380 mL of MTBE and stir at RT for 24 h. Collect the white solid by filtration to give the title compound (41.5 g, 137 mmol, 58% Yield). $^1$H NMR (400 MHz, DMSO-$d_6$) δ 8.68-8.55 (m, 1H), 4.51-4.42 (m, 1H), 3.91-3.75 (m, 1H), 3.36 (s, 3H), 2.91 (d, J=14.6 Hz, 1H), 2.69-2.61 (m, 1H), 2.52-2.46 (m, 2H), 2.28-2.22 (m, 1H), 2.17-2.10 (m, 1H), 1.96 (t, J=4.5 Hz, 1H), 1.89-1.79 (m, 1H), 1.43 (d, J=6.7 Hz, 2H), 1.36-1.26 (m, 1H), 1.05 (s, 2H), 0.75 (s, 2H).

Preparation 3

(R)-2-Azetidinemethanol Hydrochloride

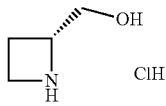

To a 2-neck RBF, equipped with a nitrogen inlet, add: (R)-1-(tert-butoxycarbonyl)azetidine-2-carboxylic acid (30 g, 146 mmol), THF (300 mL), and 4-methylmorpholine (17.7 mL, 161 mmol). Cool the mixture to −10° C. and add isobutyl chloroformate (21 mL, 161 mmol) dropwise. Stir the mixture for 30 min and then warm to RT. Remove the resulting solid by filtration. Cool the filtrate to 0° C. and add a solution of sodium borohydride (11.1 g, 292 mmol) in water (90 mL) dropwise (caution: gas evolution). After the addition, warm the mixture to RT and stir for 30 min. Dilute the mixture with MTBE (300 mL) and water (100 mL). Wash the mixture with saturated aqueous NaHCO$_3$ (200 mL) and then saturated aqueous NaCl (200 mL). Dry the organic phase over MgSO$_4$, filter, and concentrate to dryness to give an oil (27 g). Carefully add HCl (4.0 M) in 1,4-dioxane (110 mL) [Caution: Gas evolution] and stir the resulting mixture for 3 h at RT. Evaporate the solvent in vacuo to give the title compound as an oil (16 g, 89%). Use this material directly in preparations 9, 11, 16 and 36.

Preparation 4

(2S,3R)-2-methylazetidin-3-ol [(1R,4S)-7,7-dimethyl-2-oxo-norbornan-1-yl]methanesulfonic Acid

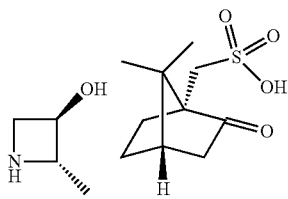

Step 1

Equip a 3-neck 500 mL RBF with an addition funnel and temperature probe. To the flask add but-2-en-1-ol (cistrans mixture) (23.7 mL, 267 mmol) and chloroform (200 mL). Cool the solution in an ice bath until the internal temperature reaches 1.2° C. Add bromine (13.7 mL, 267 mmol) dropwise by addition funnel over 2 h at a rate of ~1 drop/6 s. After the addition is complete warm the reaction to RT and stir for 30 min. Turn off the stirring and allow the reaction to stand for 3 days. Quench with sat. Na$_2$S$_2$O$_3$ solution and stir vigorously for 10 min. Allow the mixture to stand for 3 days. Remove the organic layer and extract the aqueous fraction with DCM (×3). Combine the organics and dry over Na$_2$SO$_4$, filter and concentrate in vacuo to give 2,3-dibromobutan-1-ol (62.3 g, 269 mmol).

Step 2

Procedure A

Equip a 3-neck 1 L RBF with an addition funnel and temperature probe. To the flask add 2,3-dibromobutan-1-ol (62.3 g, 269 mmol) and THF (180 mL). Place the flask in a water bath at RT. Add a solution of KOH (15.1 g, 269 mmol) in water (135 mL) dropwise over 10 min via the addition funnel. Stir at RT for 2 h. Separate the organic phase. Extract the aqueous fraction with 3×150 mL EtOAc. Combine the organics, wash once with ~200 mL brine, dry over Na$_2$SO$_4$ and filter. Carefully concentrate the organics (100 mbar, 30° C. until minimum volume, then 10 mbar, 30° C. for 10 min) to give 37 g of a mixture of 2-(1-bromoethyl)oxirane (60% mass), 2,3-dibromobutan-1-ol (36% mass), and EtOAc (4% mass) as determined by $^1$H NMR. To the mixture, add EtOH (100 mL), aminodiphenylmethane (36 mL, 208.6 mmol), and NaHCO$_3$ (26 g, 309 mmol). Heat the reaction mixture to 65° C. overnight. Cool to RT.

Procedure B

In a first flask, add 2,3-dibromobutan-1-ol (72.6 g, 313 mmol) and THF (200 mL). Place the flask in a water bath at RT. Add a solution of KOH (17.6 g, 314 mmol) in water (150 mL). Stir at RT overnight. Separate the organic phase. Extract the aqueous fraction with EtOAc (3×150 mL). Combine the organics, wash once with ~200 mL saturated aqueous NaCl solution, dry over Na$_2$SO$_4$ and filter. Concentrate the organic layer in vacuo (100 mbar, 30° C. until minimum volume, then 10 mbar, 30° C. for 10 min) to give 41.1 g of a mixture of 2-(1-bromoethyl)oxirane (75% mass), 2,3-dibromobutan-1-ol (22% mass), and EtOAc (3% mass) as determined by $^1$H NMR.

In a second flask, add 2,3-dibromobutan-1-ol (10 g, 43 mmol) and THF (30 mL). Place the flask in a water bath at RT. Add a solution of KOH (2.42 g, 43.1 mmol) in water (20 mL). Stir at RT overnight. Separate the organic phase. Extract the aqueous fraction with 3×50 mL EtOAc. Combine the organics, wash once with ~200 mL saturated aqueous NaCl solution, dry over Na$_2$SO$_4$ and filter. Concentrate the organic layer in vacuo (100 mbar, 30° C. until minimum volume, then 10 mbar, 30° C. for 10 min) to give 5.4 g of a mixture of 2-(1-bromoethyl)oxirane (66% mass), 2,3-dibromobutan-1-ol (32% mass), and EtOAc (2% mass) as determined by $^1$H NMR.

In a third flask, add 2,3-dibromobutan-1-ol (10 g, 43 mmol) and THF (30 mL). Place the flask in a water bath at RT. Add a solution of KOH (2.42 g, 43.1 mmol) in water (20 mL). Heat the mixture to 50° C. for 2 h. Cool to RT. Separate the organic phase. Extract the aqueous fraction with 3×50 mL EtOAc. Combine the organics, wash once with ~200 mL brine, dry over Na$_2$SO$_4$ and filter. Concentrate the organic layer in vacuo (100 mbar, 30° C. until minimum volume, then 10 mbar, 30° C. for 10 min) to give 5.4 g of a mixture of 2-(1-bromoethyl)oxirane (70% mass), 2,3-dibromobutan-1-ol (28% mass), and EtOAc (2% mass) as determined by $^1$H NMR.

Combine the mixtures from the three reactions together in a RBF to give 51.9 g of 2-(1-bromoethyl)oxirane (73% mass). Add EtOH (100 mL), aminodiphenylmethane (44 mL, 255.0 mmol), and NaHCO$_3$ (32 g, 380.926 mmol). Stir the resulting mixture at RT for 2 h and then heat to 65° C. and continue stirring overnight. Cool to RT. Combine the crude reaction mixtures from Procedures A and B together for purification. Remove the solids by filtration, washing with EtOH. Concentrate the filtrate to dryness. Dissolve the resulting oil in DCM. Wash the resulting solution twice with NH$_4$Cl solution, dry over Na$_2$SO$_4$, filter and concentrate to a volume of ~150 mL. Allow the mixture to stand overnight. Remove the solids by filtration. Purify the filtrate by normal phase silica chromatography (70% MTBE:hexanes) to provide crude 1-benzhydryl-2-methyl-azetidin-3-ol (66.8 g). ES/MS (m/z): 254 (M+H).

Step 3

Dissolve 1-benzhydryl-2-methyl-azetidin-3-ol (66.8 g) in MeOH (608 mL). Purify the resulting solution using a 5×25 cm Lux i-Cellulose 5 column using a solvent system of 85/15 CO$_2$/EtOH with 0.5% dimethylethylamine and a flow rate of 300 mL/min to give (2S,3R)-1-benzhydryl-2-methyl-azetidin-3-ol (19.2 g).

Step 4

Charge a RBF with (2S,3R)-1-benzhydryl-2-methyl-azetidin-3-ol (19.2 g, 75.8 mmol), L(−)-camphorsulfonic acid (19 g, 80.2 mmol), EtOH (100 mL) and Et$_2$O (50 mL). Heat the mixture until nearly all the solids dissolve, then briefly sonicate. Heat the mixture to reflux, then cool to RT and store in the freezer overnight. Collect the solids by filtration, wash with a large volume of Et$_2$O and dry under reduced pressure to give (2S,3R)-1-benzhydryl-2-methyl-azetidin-3-ol; [(1R,4S)-7,7-dimethyl-2-oxo-norbornan-1-yl]methanesulfonic acid (31.9 g, 65.7 mmol).

Step 5

Charge a RBF with 20% palladium hydroxide on carbon (50 wt-% water) (2 g). Wet the catalyst with a small volume of EtOH. To the suspension add a partial solution of (2S,3R)-1-benzhydryl-2-methyl-azetidin-3-ol; [(1R,4S)-7,7-dimethyl-2-oxo-norbornan-1-yl]methanesulfonic acid (20 g, 41.2 mmol) in EtOH (400 mL). Sparge the suspension with nitrogen for 5 min and then briefly with hydrogen. Stir the reaction mixture under a balloon of hydrogen until all starting material is gone by LC-MS analysis. Filter the reaction mixture through a pad of Celite®.

In a second flask, using the same procedure, hydrogenate (2S,3R)-1-benzhydryl-2-methyl-azetidin-3-ol; [(1R,4S)-7,7-dimethyl-2-oxo-norbornan-1-yl]methanesulfonic acid (10 g, 20.6 mmol) with 20% palladium hydroxide on carbon (50 wt-% water) (1 g) in EtOH (200 mL).

In a third flask using the same procedure, hydrogenate (2S,3R)-1-benzhydryl-2-methyl-azetidin-3-ol; [(1R,4S)-7,7-dimethyl-2-oxo-norbornan-1-yl]methanesulfonic acid (2 g, 4.12 mmol) with 20% Palladium hydroxide on carbon (50 wt-% water) (0.2 g) in EtOH (40 mL).

Combine the three filtrates together and concentrate in vacuo. Suspend the material in n-heptane and sonicate for 10 min and then collect the solids by filtration. Repeat the sonication-filtration sequence four more times. Dry the solid under vacuum overnight to give the title compound (20.11 g; 53% yield over 5 steps). $^1$H NMR (399.85 MHz, MeOD): 4.35-4.25 (m, 2H), 4.07 (dd, J=6.9, 10.6 Hz, 1H), 3.78 (dd, J=7.0, 10.6 Hz, 1H), 3.30 (m, 1H), 2.79 (d, J=14.9 Hz, 1H), 2.70-2.63 (m, 1H), 2.40-2.33 (m, 1H), 2.08-2.03 (m, 2H), 1.92 (d, J=18.4 Hz, 1H), 1.69-1.62 (m, 1H), 1.54 (d, J=6.6 Hz, 3H), 1.47-1.41 (m, 1H), 1.14 (s, 3H), 0.88 (s, 3H).

Preparation 5

Ethyl 2-(4-(4,4,5,5-tetramethyl-1,3,2-dioxaborolan-2-yl)pyrazol-1-yl)acetate

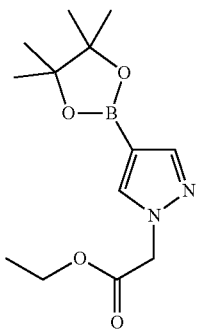 [SMILES: CCOC(=O)Cn1cc(B2OC(C)(C)C(C)(C)O2)cn1]

Charge a 500 mL RBF with 4-(4,4,5,5-tetramethyl-1,3,2-dioxaborolan-2-yl)-1H-pyrazole (15 g, 77.32 mmol), ACN (150 mL), potassium carbonate (32.06 g, 232.0 mmol,) and ethyl bromoacetate (9.09 mL, 81.2 mmol). Stir the slurry at RT overnight. Partition the reaction mixture between EtOAc (300 mL) and water (250 mL). Separate the layers and extract the aqueous layer with EtOAc. Combine the organics and wash with saturated aqueous sodium chloride (500 mL), dry over sodium sulfate, filter and concentrate in-vacuo to give a light yellow oil. Purify by silica gel chromatography using a gradient of 0 to 5% MeOH in DCM to give the title compound (16.8 g, 76%). $^1$H NMR (400 MHz, DMSO-d$_6$) δ 7.94 (s, 1H), 7.60 (s, 1H), 5.08 (s, 2H), 4.14 (q, J=7.1 Hz, 2H), 1.26 (m, 12H), 1.2 (t, J=7.2 Hz, 3H).

Preparation 6

2-[4-[2-[(2S)-2-Methylazetidin-1-yl]-6-(trifluoromethyl)pyrimidin-4-yl]pyrazol-1-yl]acetic Acid

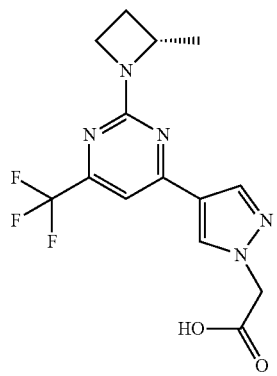 [SMILES: C[C@H]1CCN1c1nc(-c2cnn(CC(=O)O)c2)cc(C(F)(F)F)n1]

Charge a 2000 mL RBF with ethyl 2-(4-(4,4,5,5-tetramethyl-1,3,2-dioxaborolan-2-yl)pyrazol-1-yl)acetate (39.15 g, 132.8 mmol), 2,4-dichloro-6-(trifluoromethyl)pyrimidine (27.9 g, 126 mmol), 1,4-dioxane (800 mL), aqueous Na$_2$CO$_3$ (2 M, 200 mL, 400 mmol) and bis(triphenylphosphine)palladium(II) dichloride (2.8 g, 4.0 mmol). Heat the mixture to 85° C. After 2 h, cool the mixture to RT. Divide the reaction mixture into two portions and carry forward according to the following methods:

Method A:

To the first portion of the reaction mixture add [(1R,4S)-7,7-dimethyl-2-oxo-norbornan-1-yl]methanesulfonate (2S)-2-methylazetidin-1-ium salt (18.69 g, 59.75 mmol) and heat to 70° C. for 2.5 h. Cool to RT. Add aqueous NaOH (2 M, 166 mL, 332 mmol) and stir overnight at RT. Add EtOAc (500 mL) and stir the mixture for 30 min. Acidify the mixture to pH=7 using aqueous HCl (5 M) and extract with EtOAc (4×250 mL). Combine the organics, wash with saturated aqueous NaCl, dry over Na$_2$SO$_4$, filter and concentrate in-vacuo. Dissolve the residue in DCM (125 mL) and add heptane (125 mL) dropwise. Stir the mixture for 30 min. Collect the solid by filtration and wash with 1:1 DCM/heptane (50 mL). Air-dry the solid.

Method B:

Concentrate the second portion of the reaction mixture in-vacuo to remove the 1,4-dioxane. Partition the mixture between EtOAc and water. Separate the aqueous layer and concentrate the organic layer to dryness. To the flask containing the residue add 1,4-dioxane (420 mL), aqueous Na$_2$CO$_3$ (2 M, 75 mL, 150 mmol) and [(1R,4S)-7,7-dimethyl-2-oxo-norbornan-1-yl]methanesulfonate (2S)-2-methylazetidin-1-ium salt (18.69 g, 59.75 mmol). Heat the mixture to 70° C. and stir for 1.5 h. Cool the mixture to RT. Add aqueous NaOH (2 M, 125 mL, 250 mmol) and stir overnight. Add EtOAc (500 mL) and stir for 30 min. Separate the aqueous phase and allow it to sit overnight. Acidify the aqueous mixture to pH=7 using aqueous HCl (5 M) and extract with EtOAc (2×250 mL). Combine the organics, wash with saturated aqueous NaCl, dry over Na$_2$SO$_4$, filter and concentrate in-vacuo to give a solid.

Purification Method:

Combine the products from Methods A and B and dissolve in THF (485 mL). Add SiliaMetS® Thiol resin (32 g). Stir the mixture for 1 h and then filter. Concentrate the filtrate in-vacuo to give the title compound as a white powder (31.7 g, 72%). ES/MS (m/z): 342 (M+H); 340 (M–H).

Preparation 7 tert-Butyl 4-[2-[4-[2-[(2S)-2-methylazetidin-1-yl]-6-(trifluoromethyl)pyrimidin-4-yl]pyrazol-1-yl]acetyl]piperazine-1-carboxylate

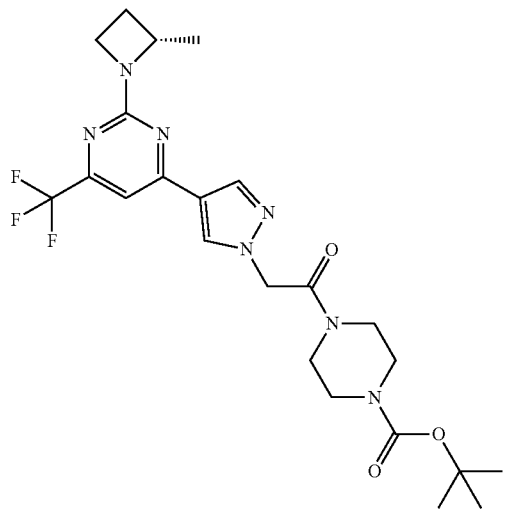 [SMILES: C[C@H]1CCN1c1nc(-c2cnn(CC(=O)N3CCN(C(=O)OC(C)(C)C)CC3)c2)cc(C(F)(F)F)n1]

Charge a 1 L RBF with 2-[4-[2-[(2S)-2-methylazetidin-1-yl]-6-(trifluoromethyl)pyrimidin-4-yl]pyrazol-1-yl]acetic acid (31.7 g, 91.0 mmol), tert-butyl piperazine-1-carboxylate (20.5 g, 109 mmol) and DCM (320 mL). To the resulting solution add Et$_3$N (25.6 mL, 182 mmol) and then dropwise 2,4,6-tripropyl-1,3,5,2,4,6-trioxatriphosphorinane-2,4,6-trioxide anhydride solution (50 wt % in EtOAc, 68 mL, 114.2 mmol). Stir at RT for 1 h. Wash the reaction with water (500 mL) and then saturated aqueous NaCl. Dry the organics over Na$_2$SO$_4$, filter, and concentrate under high vacuum to give the title compound (52.5 g, estimated 88 wt % pure based on theoretical quantitative yield of product). ES/MS (m/z): 510 (M+H); 508 (M–H).

Preparation 8 tert-Butyl 4-[4-[2-chloro-6-(trifluoromethyl)pyrimidin-4-yl]pyrazol-1-yl]piperidine-1-carboxylate

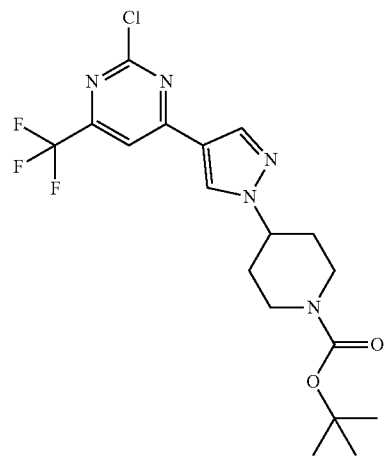 [SMILES: CC(C)(C)OC(=O)N1CCC(n2cc(-c3cc(C(F)(F)F)nc(Cl)n3)cn2)CC1]

To a microwave vial add 2,4-dichloro-6-(trifluoromethyl)pyrimidine (0.7 g, 3.05 mmol) and 1,4-dioxane (15 mL). To the solution add tert-butyl 4-(4-(4,4,5,5-tetramethyl-1,3,2-dioxaborolan-2-yl)-1H-pyrazol-1-yl)piperidine-1-carboxylate (1.55 g, 4.0 mmol), tetrakis(triphenylphosphine)palladium(0) (0.195 g, 0.17 mmol) and aqueous Na$_2$CO$_3$ (2 M, 5.5 mL, 11 mmol). Seal the vial and heat in a microwave reactor at 85° C. for 1 h. In a second vial, carry out the same reaction at the same scale. Combine the reaction mixtures in a separatory funnel. Dilute the reaction mixture with saturated aqueous sodium bicarbonate and extract twice with EtOAc. Combine the extracts and dry over Na$_2$SO$_4$, filter, and concentrate. Purify the residue by silica gel chromatography using a gradient of 0 to 50% EtOAc/hexanes to give the title compound as a white solid (2.33 g, 88%). ES/MS (m/z): 432,434 (M+H); 430,432 (M–H).

Preparation 9 tert-Butyl 4-[4-[2-[(2R)-2-(hydroxymethyl)azetidin-1-yl]-6-(trifluoromethyl)pyrimidin-4-yl]pyrazol-1-yl]piperidine-1-carboxylate

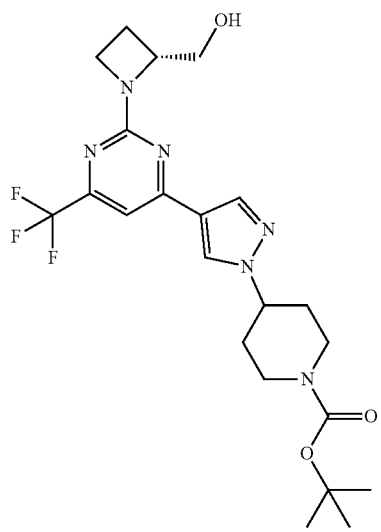 [SMILES: CC(C)(C)OC(=O)N1CCC(n2cc(-c3cc(C(F)(F)F)nc(N4CC[C@@H]4CO)n3)cn2)CC1]

In three separate microwave reaction vials, combine tert-butyl 4-[4-[2-chloro-6-(trifluoromethyl)pyrimidin-4-yl]pyrazol-1-yl]piperidine-1-carboxylate (1 g, 2.3 mmol) and 1,4-dioxane (16 mL). Add (R)-2-azetidinemethanol hydrochloride (0.52 g, 4.3 mmol) and DIPEA (1.6 mL, 9.3 mmol). Seal the vials and heat in a microwave reactor to 130° C. for 2.5 h. Combine the resulting reaction mixtures, then dilute the mixture with saturated aqueous NaHCO₃ and extract twice with EtOAc. Combine the extracts and dry over Na₂SO₄, filter, and concentrate. Purify the residue by silica gel chromatography using a gradient of 10 to 80% EtOAc/hexanes to give the title compound as a white foam (3.2 g, 95%). ES/MS (m/z): 483 (M+H).

Preparation 10 tert-Butyl 3-[4-[2-chloro-6-(trifluoromethyl)pyrimidin-4-yl]pyrazol-1-yl]azetidine-1-carboxylate

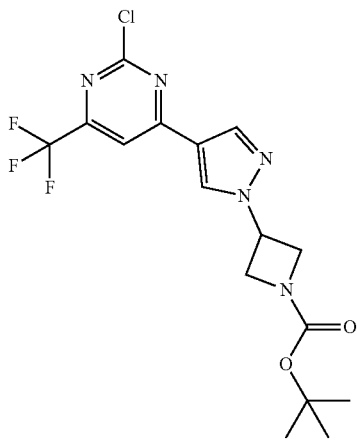 [SMILES: CC(C)(C)OC(=O)N1CC(n2cc(-c3cc(C(F)(F)F)nc(Cl)n3)cn2)C1]

To a microwave vial add 2,4-dichloro-6-(trifluoromethyl)pyrimidine (0.50 g, 2.30 mmol) and 1,4-dioxane (22 mL) and water (2 mL). To the solution add tert-butyl 3-(4-(4,4,5,5-tetramethyl-1,3,2-dioxaborolane-2-yl)-1H-pyrazole-1-yl)azetidine-1-carboxylate (0.630 g, 1.71 mmol), [1,1'-bis(diphenylphosphino)ferrocene]dichloropalladium(II) (0.20 g, 0.26 mmol) and K₂CO₃ (500 mg, 3.67 mmol). Seal the vial and stir at RT overnight. Load the crude reaction on a silica cartridge, dry in vacuum oven and purify the residue by flash chromatography (gradient 0 to 45% EtOAc/hexane) to give the title compound as alight brown oil (0.375 g, 49%). ES/MS (m/z).:348 (M+H-ᵗBu); 402 (M–H).

Preparation 11 tert-Butyl 3-[4-[2-[(2R)-2-(hydroxymethyl)azetidin-1-yl]-6-(trifluoromethyl)pyrimidin-4-yl]pyrazol-1-yl]azetidine-1-carboxylate

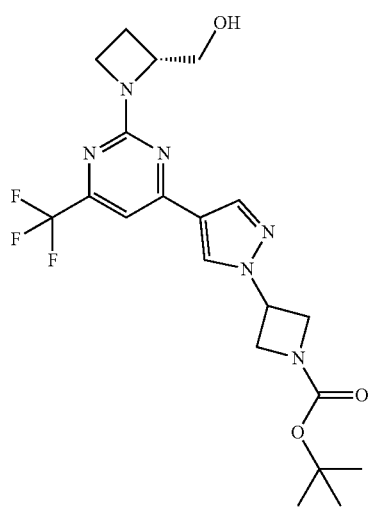 [SMILES: CC(C)(C)OC(=O)N1CC(n2cc(-c3cc(C(F)(F)F)nc(N4CC[C@@H]4CO)n3)cn2)C1]

To a vial combine tert-butyl 3-[4-[2-chloro-6-(trifluoromethyl)pyrimidin-4-yl]pyrazol-1-yl]azetidine-1-carboxylate (190 mg, 0.47 mmol) and THF (18 mL). Add (R)-2-azetidinemethanol hydrochloride (150 mg, 1.23 mmol) and DIPEA (1.0 mL, 5.7 mmol). Seal the vial and heat in the microwave reactor to 100° C. for 1 h 40 min. After cooling to RT, load the crude reaction on a silica cartridge, dry in vacuum oven and purify the residue by silica gel chromatography using a gradient of 0 to 80% (5% MeOH/EtOAc)/hexanes to give the title compound as a colorless oil (153 mg, 72%). ES/MS (m/z): 455 (M+H).

Preparation 12 tert-Butyl 3-[4-[2-[(2S,3R)-3-hydroxy-2-methyl-azetidin-1-yl]-6-(trifluoromethyl)pyrimidin-4-yl]pyrazol-1-yl]azetidine-1-carboxylate

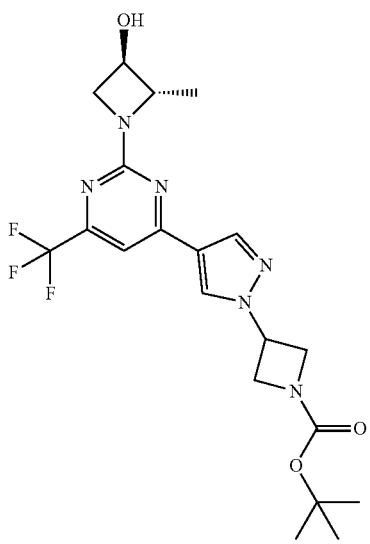 [SMILES: C[C@H]1[C@H](O)CN1c1nc(-c2cnn(C3CN(C(=O)OC(C)(C)C)C3)c2)cc(C(F)(F)F)n1]

Prepare the title compound essentially as described in Preparation 11 using (2S,3R)-2-methylazetidin-3-ol [(1R,4S)-7,7-dimethyl-2-oxo-norbornan-1-yl]methanesulfonic acid. ES/MS (m/z): 455 (M+H).

Preparation 13 tert-Butyl 3-[4-[2-[(2S)-2-methylazetidin-1-yl]-6-(trifluoromethyl)pyrimidin-4-yl]pyrazol-1-yl]azetidine-1-carboxylate

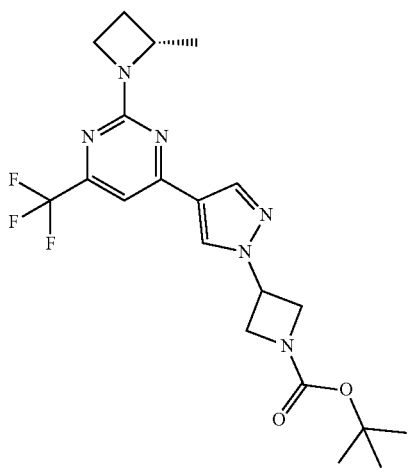 [SMILES: C[C@H]1CCN1c1nc(-c2cnn(C3CN(C(=O)OC(C)(C)C)C3)c2)cc(C(F)(F)F)n1]

Prepare the title compound essentially as described in Preparation 11 using [(1R,4S)-7,7-dimethyl-2-oxo-norbornan-1-yl]methanesulfonate (2S)-2-methylazetidin-1-ium salt. Purify the reaction by silica gel chromatography using 45% EtOAc/hexanes. ES/MS (m/z): 439 (M+H).

Preparation 14

2-[4-[5-Cyano-6-[(2S)-2-methylazetidin-1-yl]-4-(trifluoromethyl)-2-pyridyl]pyrazol-1-yl]acetic Acid

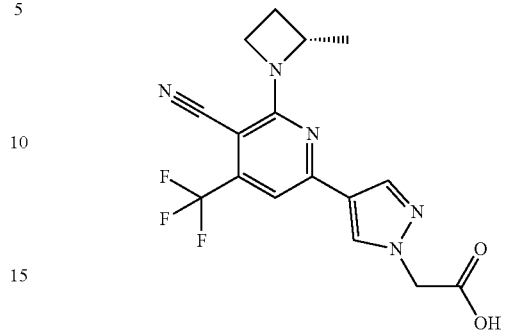

Charge an RBF with ethyl 2-(4-(4,4,5,5-tetramethyl-1,3,2-dioxaborolan-2-yl)pyrazol-1-yl)acetate (2.95 g, 10.5 mmol), 2,6-dichloro-4-(trifluoromethyl)pyridine-3-carbonitrile (2 g, 8.3 mmol), 1,4-dioxane (52.4 mL) and aqueous $Na_2CO_3$ (2 M, 13.3 mL, 26.6 mmol). Sparge the mixture with nitrogen for 10 min. Add bis(triphenylphosphine)palladium(II) dichloride (191 mg, 0.27 mmol). Stir the mixture at RT for 16.5 h. Equip the flask with a reflux condenser and add [(1R,4S)-7,7-dimethyl-2-oxo-norbornan-1-yl]methanesulfonate (2S)-2-methylazetidin-1-ium salt (2.73 g, 9.10 mmol). Heat the mixture to 70° C. and stir for 3 h, then cool to RT. Add aqueous NaOH (2 M, 21 mL, 42 mmol) and stir the mixture at RT for 15 min. Evaporate the organic solvent in-vacuo. Dilute the residue with water (50 mL) and decant the water away from the solid. Repeat this process two times with water (50 mL).

Collect the solid by vacuum filtration and air-dry overnight. Add 2-methyltetrahydrofuran (30.4 mL) and aqueous citric acid (6.5 wt %, 30.4 mL). Stir for 5 min and then separate the layers. Wash the organic layer with aqueous citric acid (6.5 wt %, 30.4 mL). Dry the organic solution over $MgSO_4$, filter, and concentrate to give the title compound (3.14 g, estimated 97 wt % pure based on theoretical quantitative yield of product). ES/MS (m/z): 366 (M+H); 364 (M−H).

Preparation 15 tert-Butyl 4-[4-[6-chloro-5-cyano-4-(trifluoromethyl)-2-pyridyl]pyrazol-1-yl]piperidine-1-carboxylate

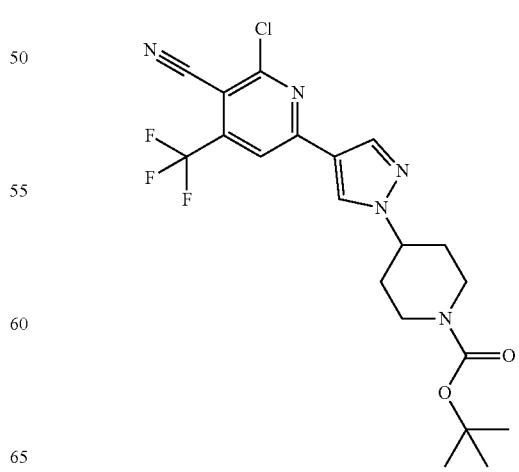

Method A:

To a microwave reactor vial add 2,6-dichloro-4-(trifluoromethyl)pyridine-3-carbonitrile (497 mg, 2.063 mmol), tert-butyl 4-[4-(4,4,5,5-tetramethyl-1,3,2-dioxaborolan-2-yl)pyrazol-1-yl]piperidine-1-carboxylate (867.2 mg, 2.3 mmol), 1,1'-bis(diphenylphosphino)ferrocene-palladium(II) dichloride DCM complex (91.2 mg, 0.109 mmol), aqueous potassium carbonate (3 M solution, 2.1 mL, 6.3 mmol), and 1,4-dioxane (10.5 mL). Sparge the mixture with nitrogen for 5 min, seal, and heat to 80° C. After 1 h, cool to RT. Filter the mixture over a Celite® plug, rinsing with EtOAc. Concentrate and purify the residue by silica gel chromatography using a gradient of 15 to 40% EtOAc in hexanes, then briefly dry in-vacuo at 35° C. to give the title compound (705 mg, 64%). ES/MS (m/z): 454,456 (M−H).

Method B:

To an RBF add 2,6-dichloro-4-(trifluoromethyl)pyridine-3-carbonitrile (1.07 g, 4.44 mmol) and 1,4-dioxane (25 mL). Add tert-butyl 4-[4-(4,4,5,5-tetramethyl-1,3,2-dioxaborolan-2-yl)pyrazol-1-yl]piperidine-1-carboxylate (2.08 g, 5.51 mmol), tetrakis(triphenylphosphine)palladium(0) (200 mg, 0.17 mmol) and aqueous Na$_2$CO$_3$ (2 M, 8.5 mL, 17 mmol). Degas the reaction with nitrogen and heat the reaction at 85° C. for 1.5 h. Decant the organic phase from the reaction and split the crude reaction into two equal amounts to use in Preparations 16 and 17. ES/MS (m/z): 454 (M−H).

Preparation 16 tert-Butyl 4-[4-[5-cyano-6-[(2R)-2-(hydroxymethyl)azetidin-1-yl]-4-(trifluoromethyl)-2-pyridyl]pyrazol-1-yl]piperidine-1-carboxylate

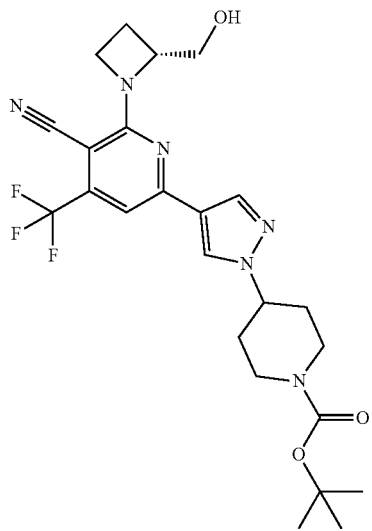 [SMILES: CC(C)(C)OC(=O)N1CCC(n2cc(-c3cc(C(F)(F)F)c(C#N)c(N4CC[C@@H]4CO)n3)cn2)CC1]

In a microwave vial add ½ of the crude reaction product from Preparation 15, Method B, (R)-2-azetidinemethanol hydrochloride (0.5 g, 4 mmol), DIPEA (1.6 mL, 9.2 mmol) and additional amount of 1,4-dioxane (16 mL). Heat the reaction at 120° C. for 2 h. Cool and concentrate the reaction to a crude product. Purify the residue by silica gel chromatography using a gradient of 50 to 80% EtOAc/hexanes, and purify again by silica gel chromatography using a gradient of 2 to 5% IPA/DCM to give the title compound as a tan solid (264 mg, 26%). ES/MS (m/z): 507 (M+H).

Preparation 17 tert-Butyl 4-[4-[5-cyano-6-[(2S,3R)-3-hydroxy-2-methyl-azetidin-1-yl]-4-(trifluoromethyl)-2-pyridyl]pyrazol-1-yl]piperidine-1-carboxylate

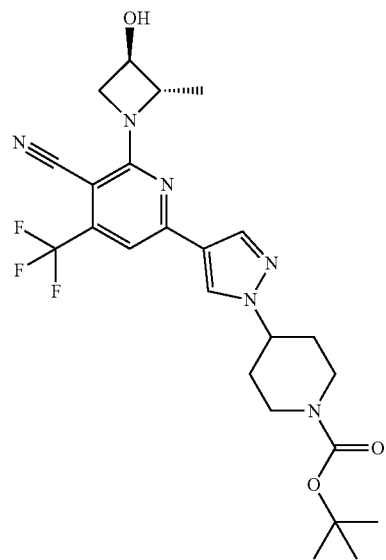 [SMILES: C[C@H]1[C@H](O)CN1c1nc(-c2cnn(C3CCN(C(=O)OC(C)(C)C)CC3)c2)cc(C(F)(F)F)c1C#N]

Prepare the title compound essentially as described in Preparation 16 using the second 2 of the crude reaction product from Preparation 15 and (2S,3R)-2-methylazetidin-3-ol [(1R,4S)-7,7-dimethyl-2-oxo-norbornan-1-yl]methanesulfonic acid. ES/MS (m/z): 507 (M+H).

Preparation 18

2-Chloro-6-[1-(4-piperidyl)pyrazol-4-yl]-4-(trifluoromethyl)pyridine-3-carbonitrile Hydrochloride

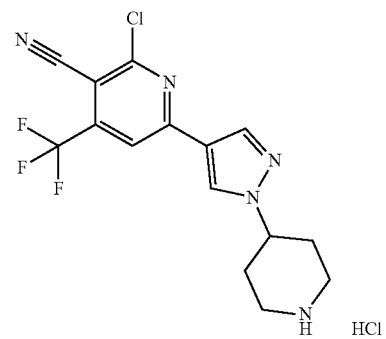 [SMILES: N#Cc1c(C(F)(F)F)cc(-c2cnn(C3CCNCC3)c2)nc1Cl ; Cl]

To a vial add tert-butyl 4-[4-[6-chloro-5-cyano-4-(trifluoromethyl)-2-pyridyl]pyrazol-1-yl]piperidine-1-carboxylate (705 mg, 1.5 mmol), 4 M HCl in 1,4-dioxane (1.5 mL, 6.0 mmol), and DCM (1.5 mL). Stir the mixture at RT. After 1 h, concentrate the mixture in-vacuo and dry the residue under vacuum overnight to give the title compound (608 mg), which is used as-is without further purification in Preparations 19 and 20. ES/MS (m/z): 356, 358 (free base M+H).

Preparation 19

2-Chloro-6-[1-(1-methyl-4-piperidyl)pyrazol-4-yl]-4-(trifluoromethyl)pyridine-3-carbonitrile

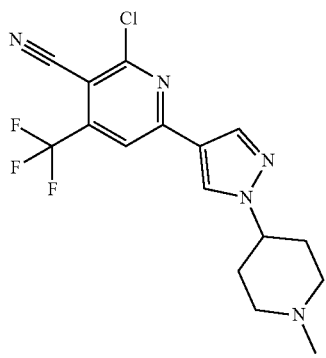 [SMILES: CN1CCC(n2cc(-c3cc(C(F)(F)F)c(C#N)c(Cl)n3)cn2)CC1]

To a vial add 2-chloro-6-[1-(4-piperidyl)pyrazol-4-yl]-4-(trifluoromethyl)pyridine-3-carbonitrile hydrochloride (303.3 mg, 0.74 mmol), 13.3 M formaldehyde in water (0.2 mL, 3 mmol), sodium triacetoxyborohydride (378 mg, 1.73 mmol), and 1,2-dichloroethane (6.0 mL). Stir the mixture at RT for 30 min. Add saturated aqueous sodium bicarbonate and extract with DCM two times. Combine the extracts and concentrate in-vacuo to give the title compound (285 mg, 99% yield). ES/MS (m/z): 370, 372 (M+H).

Preparation 20 tert-Butyl 4-[4-[5-cyano-6-[(2S)-2-methylazetidin-1-yl]-4-(trifluoromethyl)-2-pyridyl]pyrazol-1-yl]piperidine-1-carboxylate

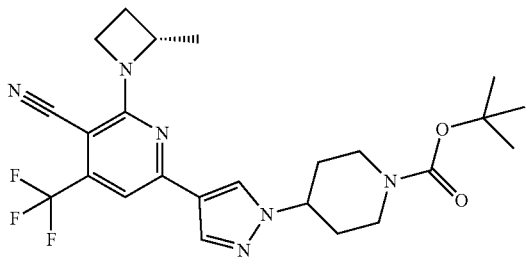 [SMILES: C[C@H]1CCN1c1nc(-c2cnn(C3CCN(C(=O)OC(C)(C)C)CC3)c2)cc(C(F)(F)F)c1C#N]

Prepare the title compound from 2,6-dichloro-4-(trifluoromethyl)pyridine-3-carbonitrile and tert-butyl 4-(4-(4,4,5,5-tetramethyl-1,3,2-dioxaborolan-2-yl)-1H-pyrazol-1-yl)piperidine-1-carboxylate using essentially the same procedure as Example 10 below.

ES/MS (m/z): 491 (M+H)

Preparation 21 tert-Butyl 4-[4-[2-[(2S)-2-methylazetidin-1-yl]-6-(trifluoromethyl)pyrimidin-4-yl]pyrazol-1-yl]piperidine-1-carboxylate

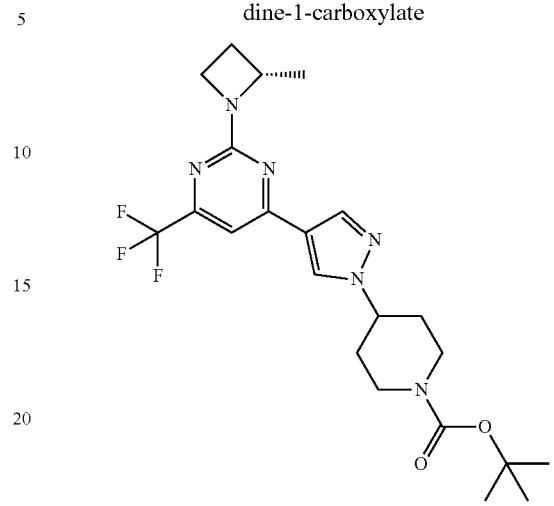

Dissolve 2,4-dichloro-6-(trifluoromethyl)pyrimidine (0.258 g, 1.1 mmol) in 1,4-dioxane (6 mL) and add tert-butyl 4-(4-(4,4,5,5-tetramethyl-1,3,2-dioxaborolan-2-yl)-1H-pyrazol-1-yl)piperidine-1-carboxylate (0.591 g, 1.52 mmol), tetrakis(triphenylphosphine)palladium(0) (68 mg, 0.059 mmol) and 2M aqueous sodium carbonate (2.2 mL, 4.4 mmol). Heat the mixture to 85° C. in a microwave reactor for 1 h. Cool to RT and add [(1R,4S)-7,7-dimethyl-2-oxo-norbornan-1-yl]methanesulfonate (2S)-2-methylazetidin-1-ium salt (0.414 g, 1.36 mmol) and DIPEA (0.6 mL, 3.4 mmol). Heat the mixture for 2 h at 110° C. Dilute the mixture with saturated aqueous sodium bicarbonate and extract twice with EtOAc. Combine the extracts, dry over sodium sulfate, then filter and evaporate. Purify the residue by silica gel chromatography using a gradient of 0 to 50% EtOAc/hexanes to give the title compound (215 mg, 41%) as a white solid. ES/MS (m/z): 467 (M+H).

Preparation 22 tert-Butyl 3-[4-[6-chloro-5-cyano-4-(trifluoromethyl)-2-pyridyl]pyrazol-1-yl]azetidine-1-carboxylate

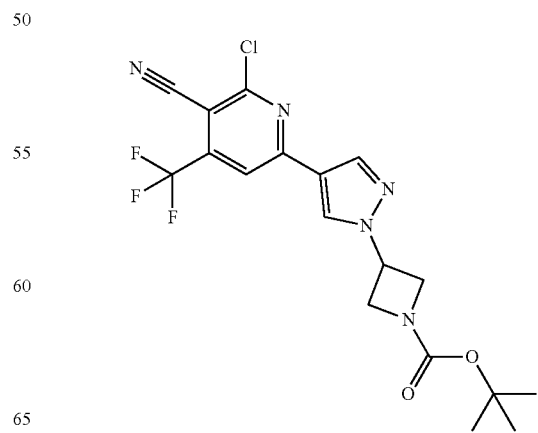

To a vial add 3-cyano-2,6-dichloro-4-(trifluoromethyl)pyridine (0.360 g, 1.49 mmol), 1,4-dioxane (7.5 ml), tert-butyl 3-(4-(4,4,5,5-tetramethyl-1,3,2-dioxaborolan-2-yl)-1H-pyrazol-1-yl)azetidine-1-carboxylate (0.727 g, 1.98 mmol), tetrakis(triphenylphosphine)palladium(0) (95 mg, 0.08 mmol), and 2M aqueous sodium carbonate (2.8 mL, 5.6 mmol, 2 mol/L). Seal the vessel and heat in a microwave reactor at 85° C. for 1 h. Dilute with saturated sodium bicarbonate and extract twice with EtOAc. Combine the extracts, dry over sodium sulfate, filter and evaporate. Purify the residue by silica gel chromatography using a gradient of 0 to 90% EtOAc/hexanes to give the title compound (0.609 g, 95%). ES/MS (m/z): 426, 428 (M−H).

Preparation 23

2-Chloro-6-(1-tetrahydropyran-4-ylpyrazol-4-yl)-4-(trifluoromethyl)pyridine-3-carbonitrile

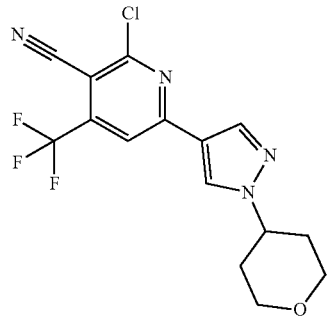 [SMILES: N#Cc1c(C(F)(F)F)cc(-c2cnn(C3CCOCC3)c2)nc1Cl]

Prepare the title compound from 1-tetrahydropyran-4-yl-4-(4,4,5,5-tetramethyl-1,3,2-dioxaborolan-2-yl)pyrazole using essentially the same procedure as Preparation 22. ES/MS (m/z): 357, 359 (M+H).

Preparation 24 tert-Butyl 3-[4-[5-cyano-6-[(2S)-2-methylazetidin-1-yl]-4-(trifluoromethyl)-2-pyridyl]pyrazol-1-yl]azetidine-1-carboxylate

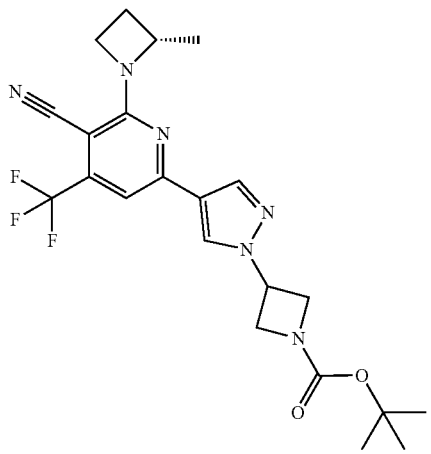 [SMILES: C[C@H]1CCN1c1nc(-c2cnn(C3CN(C(=O)OC(C)(C)C)C3)c2)cc(C(F)(F)F)c1C#N]

Dissolve tert-butyl 3-[4-[6-chloro-5-cyano-4-(trifluoromethyl)-2-pyridyl]pyrazol-1-yl]azetidine-1-carboxylate (603 mg, 1.410 mmol) in THF (18 mL). Add [(1R,4S)-7,7-dimethyl-2-oxo-norbornan-1-yl]methanesulfonate (2S)-2-methylazetidin-1-ium salt (519 mg, 1.711 mmol) and DIPEA (0.75 mL, 4.3 mmol), then heat the mixture to 130° C. for 2.5 h. Evaporate the solvent and purify the residue by silica gel chromatography using a gradient from 0 to 50% EtOAc/hexanes to give the title compound (498 mg, 76%) as a colorless oil. ES/MS (m/z): 463 (M+H), 461 (M−H).

Preparation 25 tert-Butyl N-[2-[4-[4-[5-cyano-6-[(2S)-2-methylazetidin-1-yl]-4-(trifluoromethyl)-2-pyridyl]pyrazol-1-yl]-1-piperidyl]-2-oxo-ethyl]carbamate

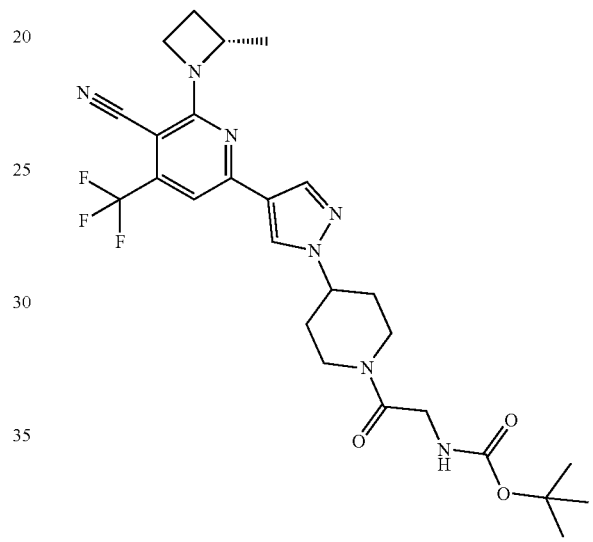

Dissolve 2-[(2S)-2-methylazetidin-1-yl]-6-[1-(4-piperidyl)pyrazol-4-yl]-4-(trifluoromethyl)pyridine-3-carbonitrile (0.129 g, 0.330 mmol) in DCM (1 mL). Add 2-(tert-butoxycarbonylamino)acetic acid (69 mg, 0.39 mmol), HATU (0.175 g, 0.460 mmol) and DIPEA (0.18 mL, 1.0 mmol). Stir the mixture at RT for 3 h, then dilute with saturated aqueous sodium bicarbonate and extract twice with DCM. Combine the organics, dry over sodium sulfate, then filter and evaporate. Purify the residue by reverse-phase chromatography on silica-bound C18 (solvent A=10 mM aqueous ammonium bicarbonate, solvent B=ACN; gradient 10 to 91% B) to give the title compound (129 mg, 71%). ES/MS (m/z): 548 (M+H).

Preparation 26

1-(2,2-Dimethyl-[1,3]dioxolan-4-ylmethyl)-4-(4,4,5,5-tetramethyl-[1,3,2]dioxaborolan-2-yl)-1H-pyrazole

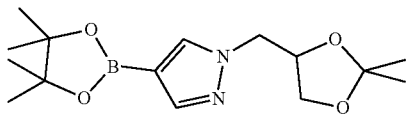

Suspend 4-(4,4,5,5-tetramethyl-1,3,2-dioxaborolan-2-yl)-1H-pyrazole (0.500 g, 2.50 mmol) in DMF (10 mL), then add 4-(chloromethyl)-2,2-dimethyl-1,3-dioxolane (0.73 mL, 5.0 mmol) and cesium carbonate (1.64 g, 5.03 mmol). Heat the mixture to 75° C. overnight. Dilute the reaction with saturated aqueous sodium bicarbonate and extract with EtOAc. Combine the organics and wash four times with saturated aqueous NaCl, then dry over sodium sulfate, filter and evaporate to give the title compound (780 mg), which is carried forward without further purification. ES/MS (m/z): 309 (M+H).

Preparation 27

2-Chloro-6-[1-[(2,2-dimethyl-1,3-dioxolan-4-yl)methyl]pyrazol-4-yl]-4-(trifluoromethyl)pyridine-3-carbonitrile

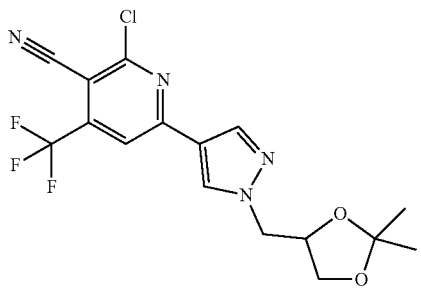 [SMILES: CC1(C)OCC(Cn2cc(-c3cc(C(F)(F)F)c(C#N)c(Cl)n3)cn2)O1]

Dissolve 3-cyano-2,6-dichloro-4-(trifluoromethyl)pyridine (0.352 g, 1.46 mmol) in 1,4-dioxane (7.3 mL). Add 1-(2,2-dimethyl-[1,3]dioxolan-4-ylmethyl)-4-(4,4,5,5-tetramethyl-[1,3,2]dioxaborolan-2-yl)-1H-pyrazole (0.602 g, 1.89 mmol), tetrakis(triphenylphosphine)palladium(0) (0.715 g, 0.619 mmol) and aqueous 2 M sodium carbonate (2.8 mL, 5.6 mmol). Purge the mixture with nitrogen for 15 min, then heat the mixture to 85° C. for 1.5 h. Dilute the reaction with saturated aqueous sodium bicarbonate and extract twice with EtOAc. Combine the organics and dry over sodium sulfate, then filter and evaporate. Purify the residue by silica gel chromatography using a gradient of 0 to 40% EtOAc/hexanes to give the title compound (207 mg, 36%) as a colorless oil. ES/MS (m/z): 387, 389 (M+H).

Preparation 28 tert-Butyl 4-[6-chloro-5-cyano-4-(trifluoromethyl)-2-pyridyl]pyrazole-1-carboxylate

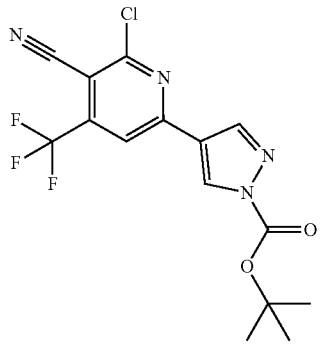 [SMILES: CC(C)(C)OC(=O)n1cc(-c2cc(C(F)(F)F)c(C#N)c(Cl)n2)cn1]

In a vial combine 3-cyano-2,6-dichloro-4-(trifluoromethyl)pyridine (195 mg, 0.785 mmol), tert-butyl 4-(4,4,5,5-tetramethyl-1,3,2-dioxaborolan-2-yl)pyrazole-1-carboxylate (250 mg, 0.85 mmol), 2 M aqueous sodium carbonate (2.5 mL, 5.0 mmol), and 1,4-dioxane (4 mL). Degas the reaction at RT by bubbling nitrogen through the reaction with stirring for 5 min. Add [1,1'-bis(diphenylphosphino)ferrocene]dichloropalladium(II) (185 mg, 0.240 mmol) and heat the reaction to 100° C. for 2 h. Add water and extract with EtOAc. Combine the extracts and concentrate in-vacuo. Purify the residue by silica gel chromatography using a gradient of 25 to 50% EtOAc/hexanes to give the title compound (40 mg, 14%) as an orange solid. ES/MS (m/z): 271, 273 (M−H—BOC).

Preparation 29 tert-Butyl N-[2-[[2-[4-[2-[(2S)-2-methylazetidin-1-yl]-6-(trifluoromethyl)pyrimidin-4-yl]pyrazol-1-yl]acetyl]amino]ethyl]carbamate

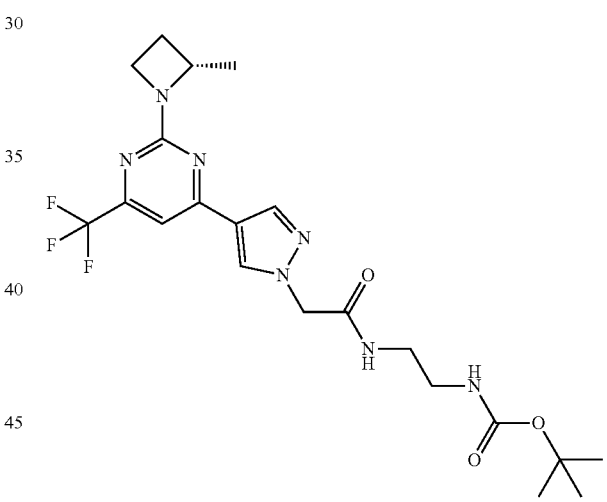

To a vial add 2-[4-[2-[(2S)-2-methylazetidin-1-yl]-6-(trifluoromethyl)pyrimidin-4-yl]pyrazol-1-yl]acetic acid (200 mg, 0.586 mmol), DMF (2 mL), DIPEA (0.31 mL, 1.76 mmol), HATU (0.267 g, 0.703 mmol), and N—BOC-ethylenediamine (0.102 mL, 0.644 mmol). Stir for 8 h at RT, then purify by preparative HPLC [parameters: solvents—aqueous 10 mM ammonium bicarbonate pH 10/5% MeOH (Solvent A) and ACN (Solvent B); precolumn—Waters BEH HILIC 100×30 mm 5 μm, 110 Å with a 15×30 mm BEH HILIC guard column; column: Phenomenex® Kinetex® EVO C18, 100×30 mm, 5 μm, 100 Å with a 15×30 mm EVO guard column using inline heater at 50° C.; gradient 33 to 67% B] to give the title compound (179 mg, 63%). ES/MS (m/z): 484 (M+H).

Prepare the compounds shown in Table 1 using essentially the same procedure as Preparation 29 and the appropriate commercially available amine.

TABLE 1

| Preparation Number | Name | Structure | ES/MS (m/z): (M + H) |
|---|---|---|---|
| 30 | tert-butyl (2S)-2-methyl-4-[2-[4-[2-[(2S)-2-methylazetidin-1-yl]-6-(trifluoromethyl)-pyrimidin-4-yl]pyrazol-1-yl]acetyl]piperazine-1-carboxylate | 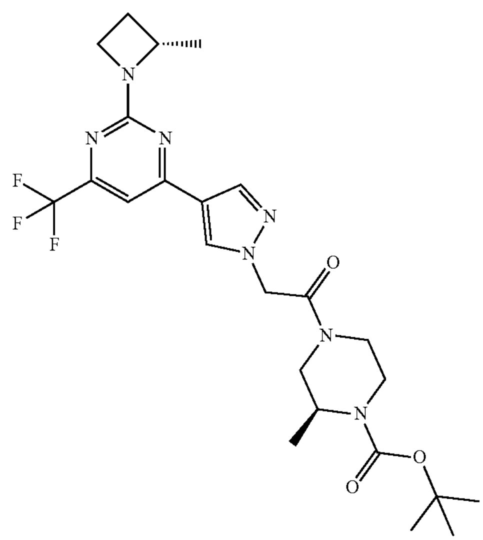 [SMILES: C[C@H]1CN(C(=O)Cn2cc(-c3cc(C(F)(F)F)nc(N4CC[C@@H]4C)n3)cn2)CCN1C(=O)OC(C)(C)C] | 524 |
| 31 | tert-butyl (3S)-3-methyl-4-[2-[4-[2-[(2S)-2-methylazetidin-1-yl]-6-(trifluoromethyl)-pyrimidin-4-yl]pyrazol-1-yl]acetyl]piperazine-1-carboxylate | 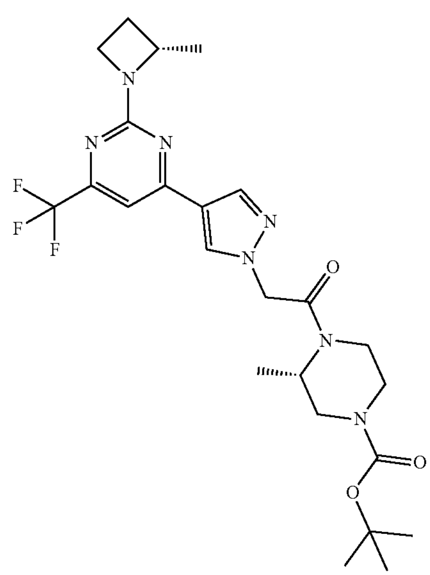 [SMILES: C[C@H]1CN(C(=O)OC(C)(C)C)CCN1C(=O)Cn1cc(-c2cc(C(F)(F)F)nc(N3CC[C@@H]3C)n2)cn1] | 524 |

TABLE 1-continued
| Preparation Number | Name | Structure | ES/MS (m/z): (M + H) |
|---|---|---|---|
| 32 | tert-butyl (2R,5S)-2,5-dimethyl-4-[2-[4-[2-[(2S)-2-methylazetidin-1-yl]-6-(trifluoromethyl)pyrimidin-4-yl]pyrazol-1-yl]acetyl]piperazine-1-carboxylate | 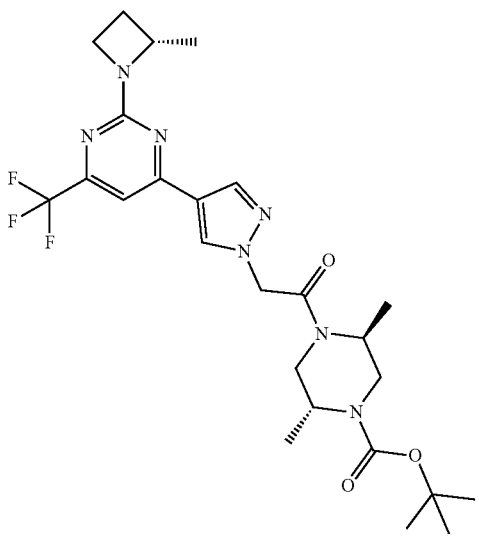 [SMILES: C[C@@H]1CN(C(=O)Cn2cc(-c3cc(C(F)(F)F)nc(N4CC[C@@H]4C)n3)cn2)[C@@H](C)CN1C(=O)OC(C)(C)C] | 538 |
| 33 | tert-butyl 2,2-dimethyl-4-[2-[4-[2-[(2S)-2-methylazetidin-1-yl]-6-(trifluoromethyl)-pyrimidin-4-yl]pyrazol-1-yl]acetyl]piperazine-1-carboxylate | 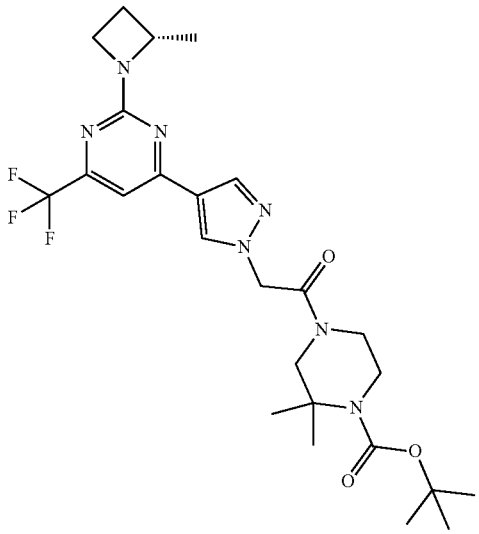 [SMILES: C[C@H]1CCN1c1nc(-c2cnn(CC(=O)N3CCN(C(=O)OC(C)(C)C)C(C)(C)C3)c2)cc(C(F)(F)F)n1] | 538 |

Preparation 34 tert-Butyl (3R)-3-[4-[2-[(2S,3R)-3-hydroxy-2-methyl-azetidin-1-yl]-6-(trifluoromethyl)pyrimidin-4-yl]pyrazol-1-yl]pyrrolidine-1-carboxylate

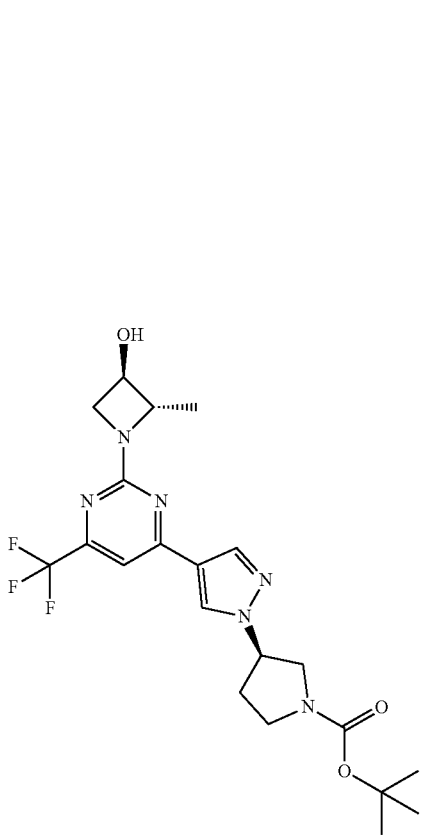 [SMILES: C[C@H]1[C@H](O)CN1c1nc(-c2cnn([C@@H]3CCN(C(=O)OC(C)(C)C)C3)c2)cc(C(F)(F)F)n1]

In a reaction vessel, combine 2,4-dichloro-6-(trifluoromethyl)pyrimidine (600 mg, 2.71 mmol) with (R)-tert-butyl 3-(4-(4,4,5,5-tetramethyl-1,3,2-dioxaborolan-2-yl)-1H-pyrazol-1-yl)pyrrolidine-1-carboxylate (1 g, 2.67 mmol), 2 M aqueous sodium carbonate (3 mL, 6 mmol) and bis(triphenylphosphine)palladium(II) dichloride (50 mg, 0.068 mmol) in 1,4-dioxane (6 mL). Degas with nitrogen and heat the mixture to 80° C. for 2 h. Dilute with EtOAc (75 mL), wash with water and saturated aqueous NaCl. Dry the organic layer over sodium sulfate, filter and concentrate. Combine the residue with (2S,3R)-2-methylazetidin-3-ol [(1R,4S)-7,7-dimethyl-2-oxo-norbornan-1-yl]methanesulfonic acid (420 mg, 1.32 mmol) in 1,4-dioxane (4 mL) and DIPEA (0.7 mL, 4 mmol) in a vial. Seal the vessel and heat to 120° C. in a microwave reactor for 1 h. Load the reaction mixture directly onto silica gel and purify by silica gel chromatography using a gradient from 0 to 80% EtOAc/hexanes to give the title compound (570 mg, 92%) as an off-white foam. ES/MS (m/z): 469 [M+H].

Preparation 35 tert-Butyl (3S)-3-[4-[2-[(2S,3R)-3-hydroxy-2-methyl-azetidin-1-yl]-6-(trifluoromethyl)pyrimidin-4-yl]pyrazol-1-yl]pyrrolidine-1-carboxylate

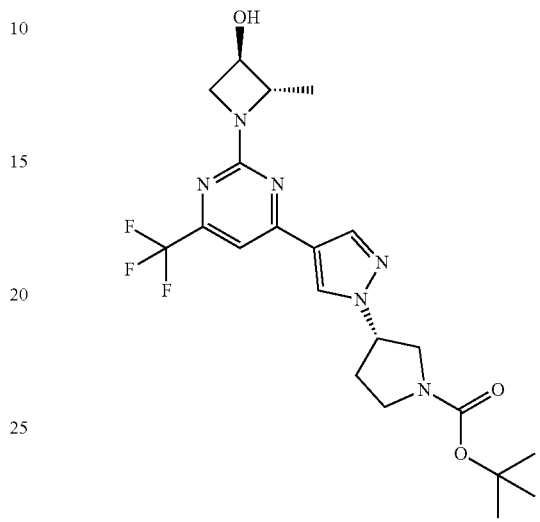

Prepare the title compound essentially as described in Preparation 34 using (S)-tert-butyl 3-(4-(4,4,5,5-tetramethyl-1,3,2-dioxaborolan-2-yl)-1H-pyrazol-1-yl)pyrrolidine-1-carboxylate. ES/MS (m/z): 469 [M+H].

Preparation 36 tert-Butyl 3-[(1R)-4-[2-[(2R)-2-(hydroxymethyl)azetidin-1-yl]-6-(trifluoromethyl)pyrimidin-4-yl]pyrazol-1-yl]pyrrolidine-1-carboxylate

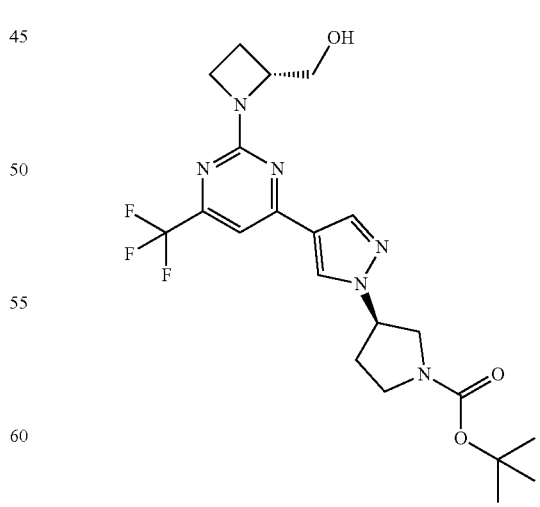

Prepare the title compound essentially as described in Preparation 34 using (R)-2-azetidinemethanol hydrochloride. ES/MS (m/z): 469 [M+H].

Preparation 37 tert-butyl 4-[4-[5-cyano-6-[(2S)-2-methylazetidin-1-yl]-4-(trifluoromethyl)-2-pyridyl]pyrazol-1-yl]-3-hydroxy-piperidine-1-carboxylate

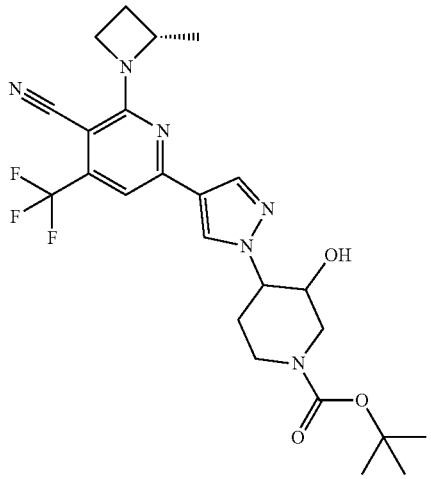 [SMILES: C[C@H]1CCN1c1nc(-c2cnn(C3CCN(C(=O)OC(C)(C)C)CC3O)c2)cc(C(F)(F)F)c1C#N]

To a vial add 4-(4,4,5,5-tetramethyl-1,3,2-dioxaborolan-2-yl)-1H-pyrazole (560 mg, 2.9 mmol), tert-butyl 7-oxa-4-azabicyclo[4.1.0]heptane-4-carboxylate (580 mg, 2.9 mmol,), DMF (10 mL), and cesium carbonate (1.7 g, 5.2 mmol). Heat the mixture to 80° C. for 6 h. Dilute the reaction with water and extract with EtOAc. Combine the extracts and dry over sodium sulfate, filter and concentrate to give crude tert-butyl 3-hydroxy-4-[4-(4,4,5,5-tetramethyl-1,3,2-dioxaborolan-2-yl)pyrazol-1-yl]piperidine-1-carboxylate (650 mg). Place this material in a RBF and add 2,6-dichloro-4-(trifluoromethyl)pyridine-3-carbonitrile (300 mg, 1.2 mmol), 1,4-dioxane (5 mL), and aqueous 2 M sodium carbonate (1.3 mL, 2.6 mmol). Degas the reaction at RT by bubbling nitrogen through the reaction with stirring for 5 min. Add tetrakis(triphenylphosphine)palladium(0) (80 mg, 0.06 mmol) and degas for an additional 3 min. Heat the reaction to 80° C. for 4 h, then cool to RT. Add DIPEA (0.6 mL, 3 mmol) and [(1R,4S)-7,7-dimethyl-2-oxo-norbornan-1-yl]methanesulfonate (2S)-2-methylazetidin-1-ium salt (410 mg, 1.4 mmol). Stir for 30 min at RT and then heat to 80° C. for 1 h. Dilute the mixture with water and extract with EtOAc. Combine the extracts and dry over sodium sulfate, filter and concentrate. Purify the residue by reverse phase chromatography (C18, gradient 10 to 100% ACN/aqueous 10 mM ammonium carbonate+5% methanol) to give the title compound (95 mg, 15%). ES/MS (m/z): 507 (M+H).

Example 1

2-[4-[2-[(2S)-2-Methylazetidin-1-yl]-6-(trifluoromethyl)pyrimidin-4-yl]pyrazol-1-yl]-1-piperazin-1-yl-ethanone

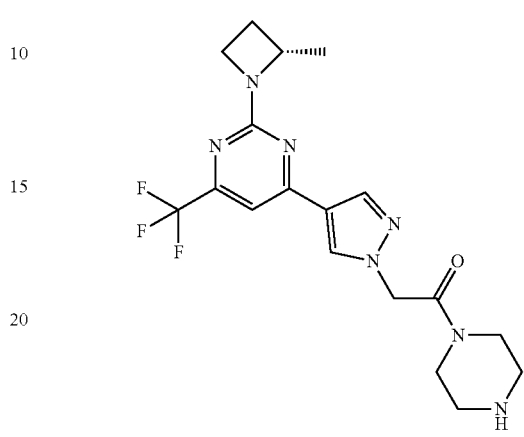

Charge a 2 L RBF with tert-butyl 4-[2-[4-[2-[(2S)-2-methylazetidin-1-yl]-6-(trifluoromethyl)pyrimidin-4-yl]pyrazol-1-yl]acetyl]piperazine-1-carboxylate (47.0 g, 89.5 mmol) and add DCM (470 mL). Add TFA (60 mL, 778 mmol) dropwise to the mixture and stir at RT for 19 h. Add more TFA (8 mL, 110 mmol) and continue stirring for 18 h. Slowly add the reaction mixture to a flask containing chilled aqueous NH$_4$OH (35 wt %, 150 mL, 1300 mmol). Separate the layers. Wash the organic layer with saturated aqueous NaCl, dry over Na$_2$SO$_4$, filter, and concentrate. Dissolve the residue in EtOAc (400 mL) and concentrate in-vacuo. Dissolve the residue in IPA (400 mL) and concentrate in vacuo to give the title compound as an off-white foam (32 g, 84%). ES/MS (m/z): 410 (M+H).

Example 1a

2-[4-[2-[(2S)-2-Methylazetidin-1-yl]-6-(trifluoromethyl)pyrimidin-4-yl]pyrazol-1-yl]-1-piperazin-1-yl-ethanone Sesquisuccinate

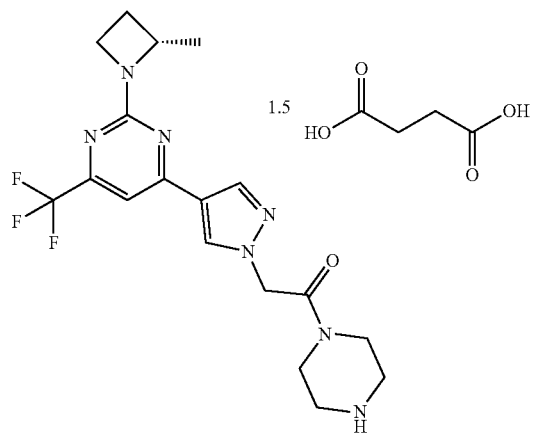 [SMILES: C[C@H]1CCN1c1nc(-c2cnn(CC(=O)N3CCNCC3)c2)cc(C(F)(F)F)n1 ; O=C(O)CCC(=O)O]

Add 2-[4-[2-[(2S)-2-methylazetidin-1-yl]-6-(trifluoromethyl)pyrimidin-4-yl]pyrazol-1-yl]-1-piperazin-1-yl-ethanone (959 g, 2.34 mol) and then IPA (11.5 L) to a reactor. Add succinic acid (550 g, 4.69 mol) and heat the mixture to 70-80° C. to give a solution. Stir the mixture between 70 and 80° C. for 2 h, then cool to 25° C. over 6 h. Filter the mixture and rinse with IPA (1 L). Dry the resulting solids at 40-50° C. for 6 h to provide the title compound (1070 g, 78%) as a white solid. $^1$H-NMR (400 MHz, DMSO-d$_6$) δ 8.41 (s, 1H), 8.18 (s, 1H), 7.33 (s, 1H), 5.24 (s, 2H), 4.53-4.43 (m, 1H), 4.06-3.93 (m, 2H), 3.58-3.47 (m, 4H), 2.95-2.82 (m, 4H), 2.47-2.40 (m, 1H), 2.37 (s, 6H-succinate methylene groups, 1.5 equiv), 2.02-1.92 (m, 1H), 1.50 (d, J=4 Hz, 3H). High-resolution ES-MS (m/z): theoretical 410.1911 (free base M+H), observed 410.1916.

XRPD peaks of Example 1a are listed in Table 2.

TABLE 2

X-ray powder diffraction peaks of Example 1a

| Peak | Angle (°2-Theta) | Relative Intensity (% of most intense peak) |
|---|---|---|
| 1 | 12.1 | 27.5% |
| 2 | 14.1 | 22.7% |
| 3 | 16.3 | 33.3% |
| 4 | 17.7 | 30.5% |
| 5 | 18.9 | 100.0% |
| 6 | 20.0 | 22.1% |
| 7 | 20.5 | 53.8% |
| 8 | 21.3 | 44.9% |
| 9 | 22.0 | 36.6% |
| 10 | 24.3 | 23.2% |

Example 2

[(2R)-1-[4-[1-(4-Piperidyl)pyrazol-4-yl]-6-(trifluoromethyl)pyrimidin-2-yl]azetidin-2-yl]methanol

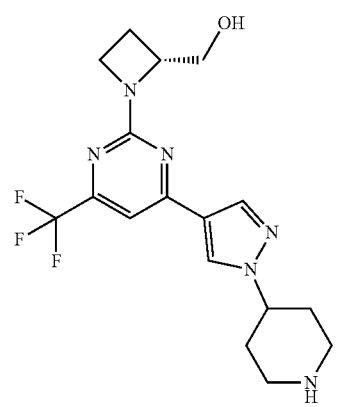 [SMILES: OC[C@H]1CCN1c1nc(-c2cnn(C3CCNCC3)c2)cc(C(F)(F)F)n1]

Dissolve tert-butyl 4-[4-[2-[(2R)-2-(hydroxymethyl)azetidin-1-yl]-6-(trifluoromethyl)pyrimidin-4-yl]pyrazol-1-yl]piperidine-1-carboxylate (2.55 g, 5.28 mmol) in DCM (50 mL) and add TFA (10 mL, 132 mmol). Stir the mixture at RT for 30 min then apply it directly to SCX resin. Wash the resin with MeOH and then with ammonia in MeOH solution (7 M). Combine the fractions containing the desired product and concentrate in vacuo. Purify the residue by silica gel chromatography using a gradient from 0 to 9% (7 M ammonia/MeOH)/DCM to give the title compound as a white powder (2.02 g, 94%). ES/MS (m/z): 383 (M+H); 381 (M−H).

Example 3

[(2R)-1-[4-[1-(Azetidin-3-yl)pyrazol-4-yl]-6-(trifluoromethyl)pyrimidin-2-yl]azetidin-2-yl]methanol

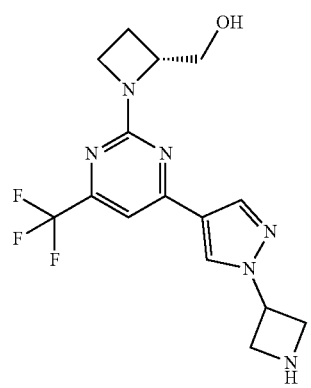 [SMILES: OC[C@H]1CCN1c1nc(-c2cnn(C3CNC3)c2)cc(C(F)(F)F)n1]

Dissolve tert-butyl 3-[4-[2-[(2R)-2-(hydroxymethyl)azetidin-1-yl]-6-(trifluoromethyl)pyrimidin-4-yl]pyrazol-1-yl]azetidine-1-carboxylate (153 mg, 0.336 mmol) in DCM (15 mL) and add TFA (5 mL, 66 mmol). Stir the mixture at RT for 1 h then concentrate under reduced pressure at RT. Co-evaporate the residue with DCM and dry under vacuum. Purify the residue by preparative HPLC (parameters: Solvent A=aqueous 10 mM ammonium bicarbonate pH 10/5% MeOH, Solvent B=ACN; column—Phenomenex® Kinetex® EVO C18, 100×30 mm, 5 um, 100 Å with 15×30 mm EVO guard column) to give the title compound (67 mg, 40%) as a white powder. ES/MS (m/z): 355 (M+H); 353 (M−H).

Example 4

(2S,3R)-1-[4-[1-(Azetidin-3-yl)pyrazol-4-yl]-6-(trifluoromethyl)pyrimidin-2-yl]-2-methyl-azetidin-3-ol

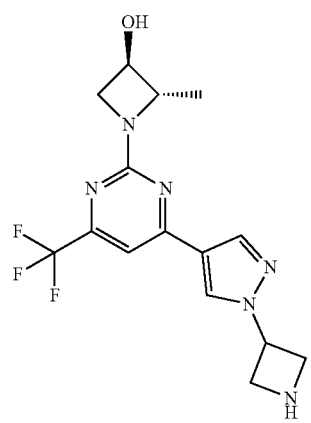 [SMILES: C[C@H]1[C@H](O)CN1c1nc(-c2cnn(C3CNC3)c2)cc(C(F)(F)F)n1]

Dissolve tert-butyl 3-[4-[2-[(2S,3R)-3-hydroxy-2-methyl-azetidin-1-yl]-6-(trifluoromethyl)pyrimidin-4-yl]

pyrazol-1-yl]azetidine-1-carboxylate (153 mg, 0.336 mmol) in DCM (15 mL) and add TFA (5 mL, 66 mmol). Stir the mixture at RT for 1 h then concentrate under reduced pressure at RT. Co-evaporate the residue with DCM and dry under vacuum. Purify the residue by preparative HPLC (parameters: Solvent A=aqueous 10 mM $NH_4HCO_3$ with 5% MeOH pH 10, Solvent B=CAN; column—Phenomenex® Kinetex® EVO C18, 100×30 mm, 5 μm, 100 Å with a 15×30 mm EVO guard column to give the title compound (79 mg, 57%) as a white powder. ES/MS (m/z): 355 (M+H); 353 (M−H).

Example 5

2-[4-[5-Cyano-6-[(2S)-2-methylazetidin-1-yl]-4-(trifluoromethyl)-2-pyridyl]pyrazol-1-yl]-N-(2-hydroxyethyl)acetamide

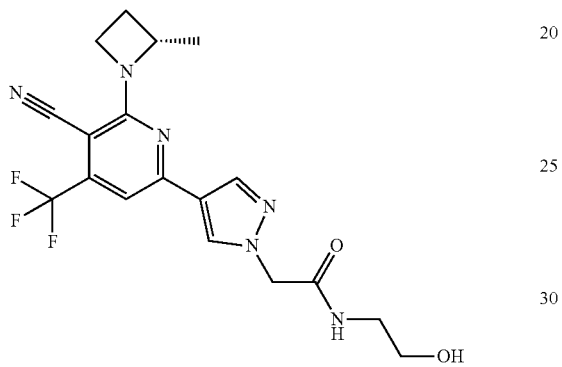

Dissolve 2-[4-[5-cyano-6-[(2S)-2-methylazetidin-1-yl]-4-(trifluoromethyl)-2-pyridyl]pyrazol-1-yl]acetic acid (351 mg, 0.96 mmol) in DMF (2 mL) and add HATU (482 mg, 1.24 mmol), ethanolamine (0.1 mL, 2 mmol) and DIPEA (0.5 mL, 3 mmol). Stir the mixture at RT for 2 d. Purify the reaction mixture directly by reversed-phase chromatography (C18-bonded silica) using a gradient from 5 to 95% MeCN/aqueous $(NH_4)_2CO_3$ (10 mM) to give the title compound (110 mg, 28%). ES/MS (m/z): 409 (M+H); 407 (M−H).

Example 6

2-[(2R)-2-(Hydroxymethyl)azetidin-1-yl]-6-[1-(4-piperidyl)pyrazol-4-yl]-4-(trifluoromethyl)pyridine-3-carbonitrile

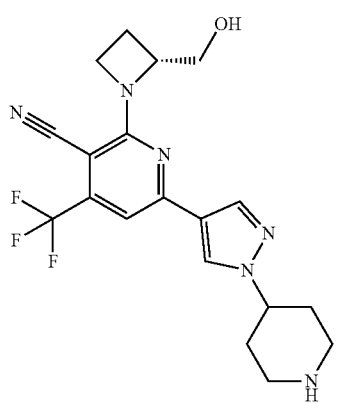 [SMILES: N#Cc1c(C(F)(F)F)cc(-c2cnn(C3CCNCC3)c2)nc1N1CC[C@@H]1CO]

Dissolve tert-butyl 4-[4-[5-cyano-6-[(2R)-2-(hydroxymethyl)azetidin-1-yl]-4-(trifluoromethyl)-2-pyridyl]pyrazol-1-yl]piperidine-1-carboxylate (264 mg, 0.52 mmol) in DCM (2 mL). Add TFA (2 mL) in one portion to the reaction and stir for 1 h. Concentrate the reaction, dilute with DCM and concentrate the reaction mixture. Dilute the reaction material with MeOH (1 mL) and add saturated aqueous $NaHCO_3$ to bring the pH-8. Purify the reaction mixture using reverse phase chromatography (40 g, C18, gradient 20-100% ACN/aqueous 10 mM $(NH_4)_2CO_3$ with 5% MeOH) to give the title compound (135.5 mg, 64%). ES/MS (m/z): 407 (M+H).

Example 7

2-[(2S,3R)-3-Hydroxy-2-methyl-azetidin-1-yl]-6-[1-(4-piperidyl)pyrazol-4-yl]-4-(trifluoromethyl)pyridine-3-carbonitrile

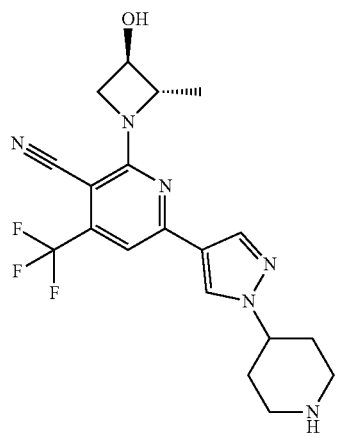 [SMILES: C[C@H]1[C@H](O)CN1c1nc(-c2cnn(C3CCNCC3)c2)cc(C(F)(F)F)c1C#N]

Dissolve tert-butyl 4-[4-[5-cyano-6-[(2S,3R)-3-hydroxy-2-methyl-azetidin-1-yl]-4-(trifluoromethyl)-2-pyridyl]pyrazol-1-yl]piperidine-1-carboxylate (220 mg, 0.43 mmol) in DCM (2 mL). Add TFA (2 mL) in one portion to the reaction and stir for 1 h. Concentrate the reaction, dilute with DCM and concentrate the reaction mixture. Dilute the reaction material with MeOH (1 mL) and add saturated aqueous $NaHCO_3$ to bring the pH-2. Purify the reaction mixture using reverse phase chromatography (40 g, C18, gradient 20-100% ACN/aqueous 10 mM $(NH_4)_2CO_3$ with 5% MeOH) to give the title compound (127 mg, 72%). ES/MS (m/z): 407 (M+H).

Example 8

2-[(2S)-2-Methylazetidin-1-yl]-6-[1-(1-methyl-4-piperidyl)pyrazol-4-yl]-4-(trifluoromethyl)pyridine-3-carbonitrile

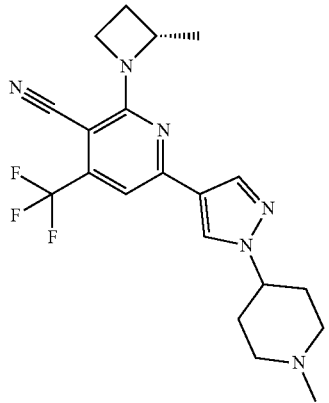 [SMILES: C[C@H]1CCN1c1nc(-c2cnn(C3CCN(C)CC3)c2)cc(C(F)(F)F)c1C#N]

To a vial add 2-chloro-6-[1-(1-methyl-4-piperidyl)pyrazol-4-yl]-4-(trifluoromethyl)pyridine-3-carbonitrile (261 mg, 0.68 mmol), [(1R,4S)-7,7-dimethyl-2-oxo-norbornan-1-yl]methanesulfonate (2S)-2-methylazetidin-1-ium salt (338 mg, 1.1 mmol), DIPEA (0.4 mL, 2 mmol), and THF (3.7 mL). Seal the vial and heat to 130° C. for 2 h. Partition the reaction mixture between DCM and aqueous 1 N HCl. Neutralize the aqueous phase with 1 N NaOH, then extract three times with DCM. Combine the organic extracts. Dry over sodium sulfate, filter, and concentrate in-vacuo. Dry the material at 50° C. in a vacuum oven for 1 h. Purify the residue by silica gel chromatography using a gradient of 5 to 10% MeOH/DCM, combine fractions containing the title compound, concentrate and dry in a vacuum oven at 50° C. overnight. Purify the residue by preparative HPLC (parameters: Solvent A=10 mM aqueous ammonium bicarbonate with 5% MeOH, Solvent B=ACN; column—Xbridge™ 30 mm×75 mm 5 μm, 45 mL/min; gradient—5 to 100% B) to give the title compound (73 mg, 26%). ES/MS (m/z): 405 (M+H).

To a 20 mL vial add 2-chloro-6-[1-(4-piperidyl)pyrazol-4-yl]-4-(trifluoromethyl)pyridine-3-carbonitrile hydrochloride (304.3 mg, 0.63 mmol), 2-[tert-butyl(dimethyl)silyl]oxyacetaldehyde (219 mg, 1.19 mmol), DIPEA (0.52 mL, 3.1 mmol), sodium triacetoxyborohydride (277.2 mg, 1.3 mmol) and DCM (2.0 mL). Stir the reaction mixture at RT for 2 h. Add 2-[tert-butyl(dimethyl)silyl]oxyacetaldehyde (219 mg, 1.2 mmol) and stir overnight at RT. Add a saturated solution of aqueous sodium bicarbonate and extract two times with DCM. Combine the organic phases, wash with saturated aqueous NaCl, dry over sodium sulfate, filter, and concentrate in-vacuo. Purify the residue by silica gel chromatography using a gradient of 40 to 70% EtOAc in hexanes to give 6-[1-[1-[2-[tert-butyl(dimethyl)silyl]oxyethyl]-4-piperidyl]pyrazol-4-yl]-2-chloro-4-(trifluoromethyl)pyridine-3-carbonitrile (220 mg, 58%).

To a vial add 6-[1-[1-[2-[tert-butyl(dimethyl)silyl]oxyethyl]-4-piperidyl]pyrazol-4-yl]-2-chloro-4-(trifluoromethyl)pyridine-3-carbonitrile (175 mg, 0.289 mmol), [(1R,4S)-7,7-dimethyl-2-oxo-norbornan-1-yl]methanesulfonate (2S)-2-methylazetidin-1-ium salt (136 mg, 0.45 mmol), DIPEA (0.15 mL, 0.85 mmol), and THF (1.5 mL, 18 mmol). Seal the vessel and heat to 130° C. for 60 min. Partition the reaction mixture between EtOAc and 1 N HCl, remove the organic layer, and extract the aqueous layer three times with EtOAc. Combine the organics, wash with saturated aqueous NaCl, dry over sodium sulfate, filter, and concentrate in-vacuo. Dissolve the residue in THF (1.3 mL) and cool the mixture to 0° C., then add 1 M tetrabutylammonium fluoride in THF (0.37 mL, 0.37 mmol) drop-wise. Allow the reaction to warm to RT and stir overnight. Concentrate the reaction mixture in-vacuo. Purify the residue by silica gel chromatography using 100% hexanes, then using a gradient of 1 to 10% (0.7 N ammonia in MeOH)/DCM to give the title compound (93 mg, 73%). ES/MS (m/z): 435 (M+H).

Example 9

6-[1-[1-(2-Hydroxyethyl)-4-piperidyl]pyrazol-4-yl]-2-[(2S)-2-methylazetidin-1-yl]-4-(trifluoromethyl)pyridine-3-carbonitrile

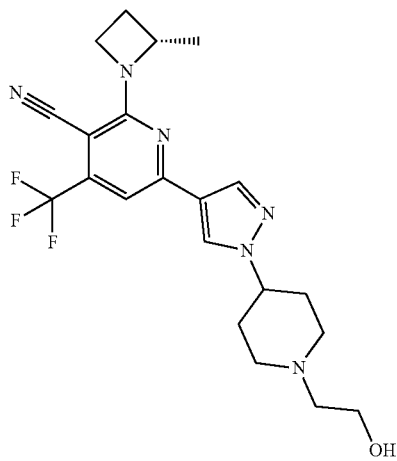 [SMILES: C[C@H]1CCN1c1nc(-c2cnn(C3CCN(CCO)CC3)c2)cc(C(F)(F)F)c1C#N]

Example 10

6-[1-[2-(Dimethylamino)ethyl]pyrazol-4-yl]-2-[(2S)-2-methylazetidin-1-yl]-4-(trifluoromethyl)pyridine-3-carbonitrile

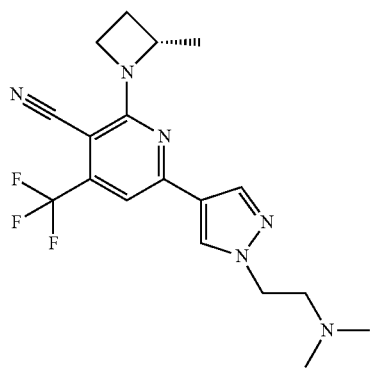 [SMILES: C[C@H]1CCN1c1nc(-c2cnn(CCN(C)C)c2)cc(C(F)(F)F)c1C#N]

To a reaction vessel add 2,6-dichloro-4-(trifluoromethyl) pyridine-3-carbonitrile (250 mg, 1.04 mmol), N,N-dimethyl-2-(4-(4,4,5,5-tetramethyl-1,3,2-dioxaborolan-2-yl)-1H-pyrazol-1-yl)ethanamine (271 mg, 1.07 mmol), 1,4-dioxane (10 mL), aqueous potassium carbonate (3 M, 1.04 mL, 3.12 mmol), and [1,1'-bis(diphenylphosphino)ferrocene]dichloropalladium(II)) (40 mg, 0.052 mmol). Seal the vessel and heat to 80° C. for 2 h, then cool the mixture to RT. Filter through a 3 g cartridge of Celite® using EtOAc to elute. Concentrate the filtrate by evaporation. To the residue add [(1R,4S)-7,7-dimethyl-2-oxo-norbornan-1-yl]methanesulfonate (2S)-2-methylazetidin-1-ium salt (378 mg, 1.24 mmol), DIPEA (0.9 mL, 5.2 mmol), and DMSO (10 mL). Heat the mixture to 120° C. for 6 h. Dilute the reaction mixture with water and load onto a Strata-XL® cartridge (8 g; previously washed with MeOH, dried, and then washed with water). Wash the cartridge with water followed by 1:1 MeOH/water and discard the eluents. Elute the product with MeOH followed by DCM and finally a 1:1 mixture of DCM/MeOH, pooling the eluted fractions. Concentrate the pooled fractions containing the title compound. Purify the residue by preparative HPLC (parameters: Solvent A=10 mM aqueous ammonium bicarbonate with 5% MeOH pH 10, Solvent B=ACN; precolumn—Waters BEH HILIC 100× 30 mm 5 μm, 110 Å with a 15×30 mm BEH HILIC guard column; column—Phenomenex® Kinetex® EVO C18, 100×30 mm, 5 μm, 100 Å with a 15×30 mm EVO guard column using inline heater at 50° C.; gradient 33 to 100% B) to give the title compound (53 mg, 13%). ES/MS (m/z): 379 (M+H).

Example 11

6-[1-(2-Hydroxyethyl)pyrazol-4-yl]-2-[(2S)-2-methylazetidin-1-yl]-4-(trifluoromethyl)pyridine-3-carbonitrile

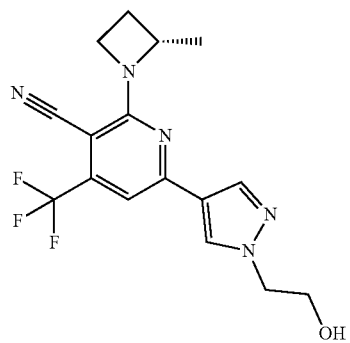 [SMILES: C[C@H]1CCN1c1nc(-c2cnn(CCO)c2)cc(C(F)(F)F)c1C#N]

Prepare the title compound using essentially the method described in Example 10 with 2-(4-(4,4,5,5-tetramethyl-1,3,2-dioxaborolan-2-yl)-1H-pyrazol-1-yl)ethanol. ES/MS (m/z): 352 (M+H).

Example 12

2-[(2S)-2-Methylazetidin-1-yl]-6-[1-(4-piperidyl)pyrazol-4-yl]-4-(trifluoromethyl)pyridine-3-carbonitrile

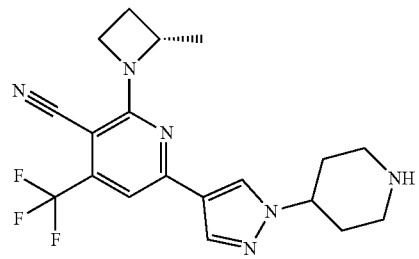 [SMILES: C[C@H]1CCN1c1nc(-c2cnn(C3CCNCC3)c2)cc(C(F)(F)F)c1C#N]

Dissolve tert-butyl 4-[4-[5-cyano-6-[(2S)-2-methylazetidin-1-yl]-4-(trifluoromethyl)-2-pyridyl]pyrazol-1-yl]piperidine-1-carboxylate (1.99 g, 4.06 mmol) in DCM (50 mL) and add TFA (10 mL, 132.3 mmol) slowly. Stir at RT for 30 min then load the reaction mixture onto four 10 g SCX cartridges. Wash the cartridges with MeOH and then with 7N ammonia in MeOH. Concentrate the basic washes in-vacuo. Purify the residue by reverse-phase chromatography on silica-bound C18 (Solvent A: 10 mM ammonium bicarbonate with 5% MeOH; Solvent B: ACN; gradient: 10-71% solvent B) to give the title compound (709 mg, 45%) as a white solid. ES/MS (m/z): 391 (M+H).

Example 13

2-[(2S)-2-Methylazetidin-1-yl]-4-[1-(4-piperidyl)pyrazol-4-yl]-6-(trifluoromethyl)pyrimidine

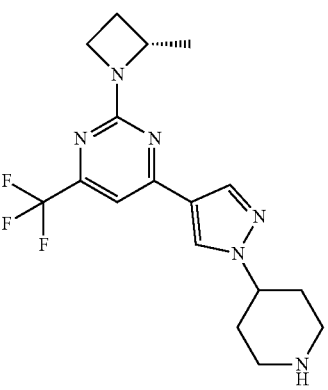 [SMILES: C[C@H]1CCN1c1nc(-c2cnn(C3CCNCC3)c2)cc(C(F)(F)F)n1]

Dissolve tert-butyl 4-[4-[2-[(2S)-2-methylazetidin-1-yl]-6-(trifluoromethyl)pyrimidin-4-yl]pyrazol-1-yl]piperidine-1-carboxylate (0.213 g, 0.457 mmol) in DCM (5 mL) and add TFA (1 mL). Stir the mixture for 25 min then load the reaction mixture directly onto a 10 g SCX cartridge. Wash the cartridge with MeOH and then elute with 7 N ammonia in MeOH. Concentrate the basic wash to give the title compound (129 mg, 77%). ES/MS (m/z): 367 (M+H).

Prepare the examples in Table 3 using essentially the method described in Example 13 and the appropriate protected amine.

TABLE 3

| Example Number | Name | Structure | ES/MS (m/z): (M + H) |
|---|---|---|---|
| 14 | (2S,3R)-2-Methyl-1-[4-[1-[(3R)-pyrrolidin-3-yl]pyrazol-4-yl]-6-(trifluoromethyl)pyrimidin-2-yl]azetidin-3-ol | 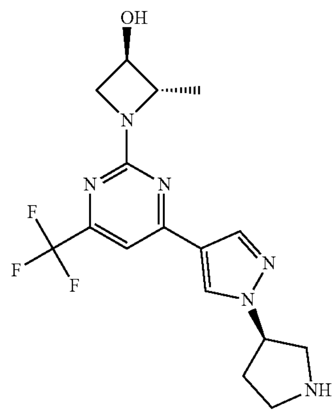 [SMILES: C[C@H]1[C@H](O)CN1c1nc(-c2cnn([C@@H]3CCNC3)c2)cc(C(F)(F)F)n1] | 369 |
| 15 | (2S,3R)-2-Methyl-1-[4-[1-[(3S)-pyrrolidin-3-yl]pyrazol-4-yl]-6-(trifluoromethyl)pyrimidin-2-yl]azetidin-3-ol | 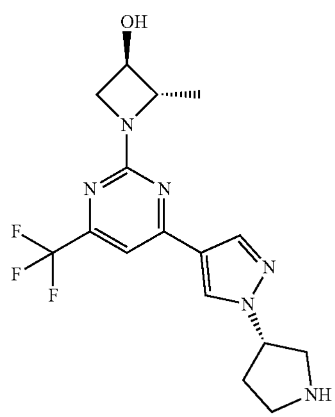 [SMILES: C[C@H]1[C@H](O)CN1c1nc(-c2cnn([C@H]3CCNC3)c2)cc(C(F)(F)F)n1] | 369 |
| 16 | [(2R)-1-[4-[1-[(3R)-Pyrrolidin-3-yl]pyrazol-4-yl]-6-(trifluoromethyl)pyrimidin-2-yl]azetidin-2-yl]methanol | 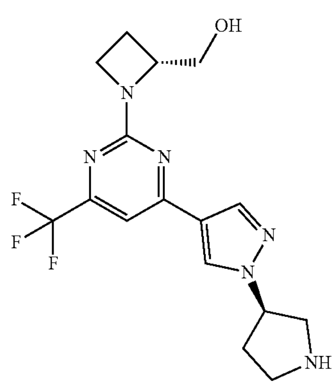 [SMILES: OC[C@H]1CCN1c1nc(-c2cnn([C@@H]3CCNC3)c2)cc(C(F)(F)F)n1] | 369 |

Example 17

6-[1-(Azetidin-3-yl)pyrazol-4-yl]-2-[(2S)-2-methyl-azetidin-1-yl]-4-(trifluoromethyl)pyridine-3-carbonitrile

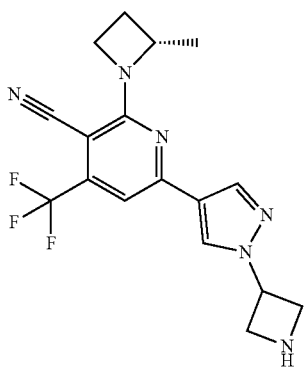 [SMILES: C[C@H]1CCN1c1nc(-c2cnn(C3CNC3)c2)cc(C(F)(F)F)c1C#N]

Prepare the title compound essentially using the same procedure as Example 12 starting from tert-butyl 3-[4-[5-cyano-6-[(2S)-2-methylazetidin-1-yl]-4-(trifluoromethyl)-2-pyridyl]pyrazol-1-yl]azetidine-1-carboxylate. Purify by preparative HPLC (parameters: solvent A—10 mM aqueous ammonium bicarbonate with 5% MeOH, solvent B—ACN; gradient 35 to 59% B; column—Phenomenex® Kinetex® EVO C18, 100×30 mm, 5 μm) to give the title compound. ES/MS (m/z): 363 (M+H).

Example 18

6-[1-[1-(2-Aminoacetyl)-4-piperidyl]pyrazol-4-yl]-2-[(2S)-2-methylazetidin-1-yl]-4-(trifluoromethyl)pyridine-3-carbonitrile

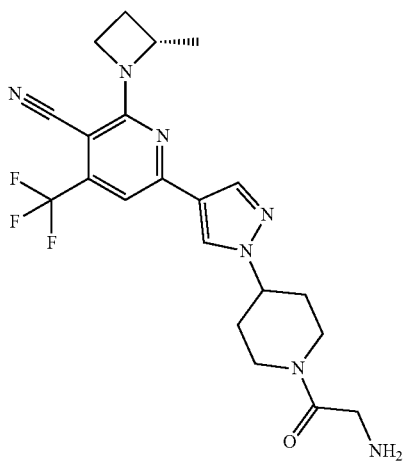 [SMILES: C[C@H]1CCN1c1nc(-c2cnn(C3CCN(C(=O)CN)CC3)c2)cc(C(F)(F)F)c1C#N]

Prepare the title compound using essentially the same procedure as Example 12 starting from tert-butyl N-[2-[4-[4-[5-cyano-6-[(2S)-2-methylazetidin-1-yl]-4-(trifluoromethyl)-2-pyridyl]pyrazol-1-yl]-1-piperidyl]-2-oxo-ethyl]carbamate. Purify by preparative HPLC (parameters: solvent A—10 mM ammonium bicarbonate with 5% MeOH; solvent B—MeOH; gradient—20 to 50% B, 55 mL/min; column—Phenomenex® Kinetex® EVO C18 30 mm×250 mm, 5 μm). ES/MS (m/z): 448 (M+H).

Example 19

6-[1-(1-Acetyl-4-piperidyl)pyrazol-4-yl]-2-[(2S)-2-methylazetidin-1-yl]-4-(trifluoromethyl)pyridine-3-carbonitrile

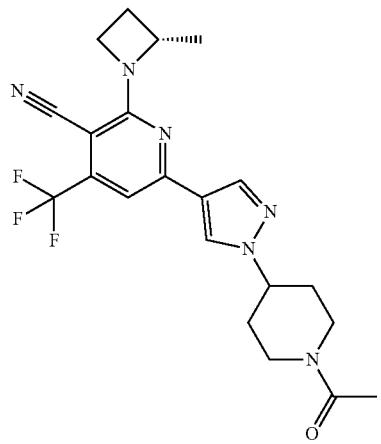 [SMILES: CC(=O)N1CCC(n2cc(-c3cc(C(F)(F)F)c(C#N)c(N4CC[C@@H]4C)n3)cn2)CC1]

Dissolve 2-[(2S)-2-methylazetidin-1-yl]-6-[1-(4-piperidyl)pyrazol-4-yl]-4-(trifluoromethyl)pyridine-3-carbonitrile (Example 12) (0.111 g, 0.284 mmol) in DCM (1 mL) and add pyridine (0.026 mL, 0.32 mmol). Cool the mixture to 0° C. and add acetyl chloride (0.024 mL, 0.34 mmol). Warm the mixture to RT and stir for 30 min. Cool the mixture to 0° C. and add pyridine (0.026 mL, 0.32 mmol) and acetyl chloride (0.024 mL, 0.34 mmol).

Warm to RT and stir for an additional 30 min. Dilute the reaction with saturated aqueous sodium bicarbonate and extract twice with DCM. Combine the organics, dry over sodium sulfate, filter and evaporate. Purify the residue by preparative HPLC (parameters: solvent A 20-10 mM ammonium bicarbonate with 5% MeOH; solvent B—MeOH; gradient 25-55%, 55 mL/min; column—Phenomenex® Kinetex® EVO C18 30 mm×250 mm, 5 μm) to give the title compound (67 mg, 55%). ES/MS (m/z): 433 (M+H).

Examples 20 to 23

Prepare the examples in Table 4 using essentially the procedure from Example 5 and the appropriate carboxylic acid and commercially available amine.

TABLE 4

| Example Number | Name | Structure | ES/MS (m/z): (M + H) |
|---|---|---|---|
| 20 | 2-[(2S)-2-Methylazetidin-1-yl]-6-[1-[2-(4-methylpiperazin-1-yl)-2-oxo-ethyl]pyrazol-4-yl]-4-(trifluoromethyl)pyridine-3-carbonitrile | 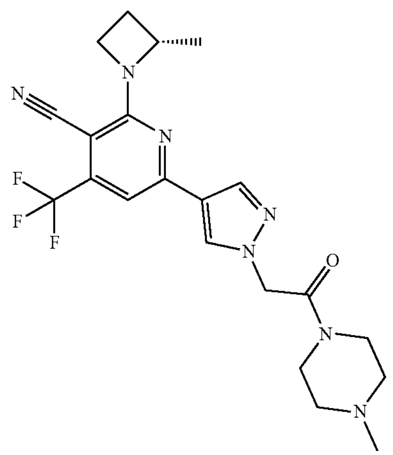 [SMILES: C[C@H]1CCN1c1nc(-c2cnn(CC(=O)N3CCN(C)CC3)c2)cc(C(F)(F)F)c1C#N] | 448 |
| 21 | 2-[4-[5-Cyano-6-[(2S)-2-methylazetidin-1-yl]-4-(trifluoromethyl)-2-pyridyl]pyrazol-1-yl]-N,N-bis(2-hydroxyethyl)acetamide | 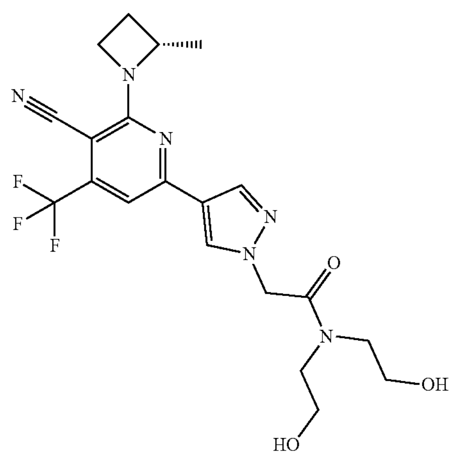 [SMILES: C[C@H]1CCN1c1nc(-c2cnn(CC(=O)N(CCO)CCO)c2)cc(C(F)(F)F)c1C#N] | 453 |
| 22 | 6-[1-[2-[(3R,4R)-3,4-Dihydroxypyrrolidin-1-yl]-2-oxo-ethyl]pyrazol-4-yl]-2-[(2S)-2-methylazetidin-1-yl]-4-(trifluoromethyl)pyridine-3-carbonitrile | 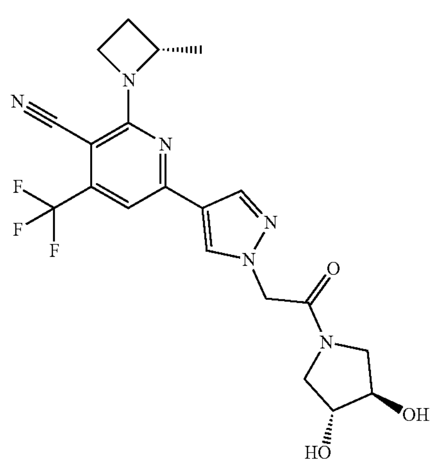 [SMILES: C[C@H]1CCN1c1nc(-c2cnn(CC(=O)N3C[C@@H](O)[C@H](O)C3)c2)cc(C(F)(F)F)c1C#N] | 451 |

TABLE 4-continued

| Example Number | Name | Structure | ES/MS (m/z): (M + H) |
|---|---|---|---|
| 23 | 6-[1-[2-[(3S,4S)-3,4-Dihydroxypyrrolidin-1-yl]-2-oxo-ethyl]pyrazol-4-yl]-2-[(2S)-2-methylazetidin-1-yl]-4-(trifluoromethyl)pyridine-3-carbonitrile | 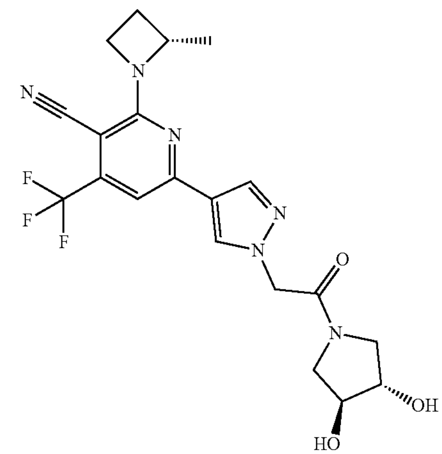 [SMILES: C[C@H]1CCN1c1nc(-c2cnn(CC(=O)N3C[C@H](O)[C@@H](O)C3)c2)cc(C(F)(F)F)c1C#N] | 451 |

Example 24

6-[1-(2,3-Dihydroxypropyl)pyrazol-4-yl]-2-[(2S)-2-methylazetidin-1-yl]-4-(trifluoromethyl)pyridine-3-carbonitrile

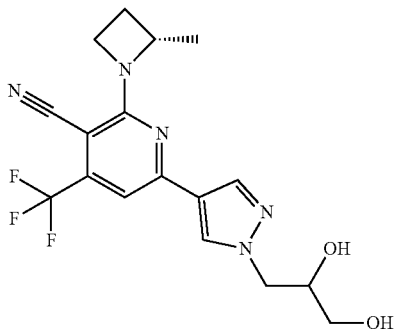 [SMILES: C[C@H]1CCN1c1nc(-c2cnn(CC(O)CO)c2)cc(C(F)(F)F)c1C#N]

Dissolve 2-chloro-6-[1-[(2,2-dimethyl-1,3-dioxolan-4-yl)methyl]pyrazol-4-yl]-4-(trifluoromethyl)pyridine-3-carbonitrile (0.204 g, 0.527 mmol) in THF (6 mL). Add aqueous hydrochloric acid (2 M, 3 mL, 6 mmol) to the mixture and stir at RT for 1.5 h. Dilute the mixture with saturated aqueous sodium bicarbonate and extract twice with EtOAc. Combine the organics and dry over sodium sulfate, then filter and evaporate to give crude 2-chloro-6-[1-(2,3-dihydroxypropyl)pyrazol-4-yl]-4-(trifluoromethyl)pyridine-3-carbonitrile (183 mg). Dissolve this crude material in its entirety in DMF (2 mL), then add [(1R,4S)-7,7-dimethyl-2-oxo-norbornan-1-yl]methanesulfonate (2S)-2-methylazetidin-1-ium salt (222 mg, 0.73 mmol) and DIPEA (0.37 mL, 2.1 mmol). Heat the mixture in a microwave reactor at 130° C. for 2.5 h. Purify the reaction mixture by preparative HPLC (parameters: solvent A—10 mM ammonium bicarbonate with 5% MeOH; solvent B—ACN; gradient 20 to 50% 60 mL/min; column—Phenomenex® Kinetex® EVO C18 30 mm×250 mm, 5 m) to give the title compound (102 mg, 51%). ES/MS (m/z): 382 (M+H).

Examples 24a and 24b

Example 24a: 6-[1-(2,3-Dihydroxypropyl)pyrazol-4-yl]-2-[(2S)-2-methylazetidin-1-yl]-4-(trifluoromethyl)pyridine-3-carbonitrile—Isomer 1

Example 24b: 6-[1-(2,3-Dihydroxypropyl)pyrazol-4-yl]-2-[(2S)-2-methylazetidin-1-yl]-4-(trifluoromethyl)pyridine-3-carbonitrile—Isomer 2

Separate the isomers of 6-[1-(2,3-dihydroxypropyl)pyrazol-4-yl]-2-[(2S)-2-methylazetidin-1-yl]-4-(trifluoromethyl)pyridine-3-carbonitrile (86 mg) using chiral SFC (parameters: column—Phenomenex® Lux® Cellulose-2, 21×250 mm; column temperature −40° C.; solvent—15% EtOH/CO2, 80 mL/min) to provide the title compounds [Isomer 1, first-eluting isomer: 35 mg, ES/MS (m/z): 382 (M+H); Isomer 2, second-eluting isomer: 39 mg, ES/MS (m/z): 382 (M+H)]. Analytical chiral SFC (parameters: column—Phenomenex® Lux® Cellulose-2, 4.6×150 mm; solvent—15% EtOH/CO$_2$, 5 mL/min): Isomer 1—retention time 3.10 min, 95.6% ee; Isomer 2—retention time 3.52 min—94.4% ee.

Example 25

2-[(2S)-2-Methylazetidin-1-yl]-6-(1H-pyrazol-4-yl)-4-(trifluoromethyl)pyridine-3-carbonitrile

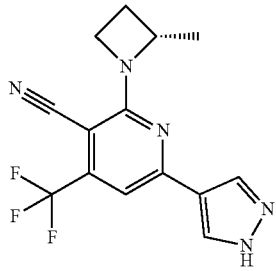 [SMILES: C[C@H]1CCN1c1nc(-c2cn[nH]c2)cc(C(F)(F)F)c1C#N]

In a vial combine tert-butyl 4-[6-chloro-5-cyano-4-(trifluoromethyl)-2-pyridyl]pyrazole-1-carboxylate (75 mg, 0.20 mmol), 1,4-dioxane (1.5 mL), and EtOH (1 mL). Add DIPEA (130 mg, 1.0 mmol) and [(1R,4S)-7,7-dimethyl-2-oxo-norbornan-1-yl]methanesulfonate (2S)-2-methylazetidin-1-ium salt (117 mg, 0.39 mmol). Heat the reaction in a microwave reactor at 200° C. for 2 h. Concentrate the reaction in-vacuo. Purify the residue by reverse-phase chromatography on silica-bound C18 using a gradient of 10 to 100% ACN/water with 0.1% formic acid to give the title compound (35 mg, 41%) as a pale yellow solid. ES/MS (m/z): 308 (M+H), 306 (M−H).

Example 26

2-[(2S)-2-Methylazetidin-1-yl]-6-(1-tetrahydropyran-4-ylpyrazol-4-yl)-4-(trifluoromethyl)pyridine-3-carbonitrile

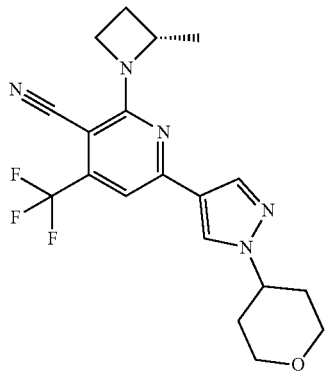 [SMILES: C[C@H]1CCN1c1nc(-c2cnn(C3CCOCC3)c2)cc(C(F)(F)F)c1C#N]

In a vial combine 2-chloro-6-(1-tetrahydropyran-4-ylpyrazol-4-yl)-4-(trifluoromethyl)pyridine-3-carbonitrile (105 mg, 0.29 mmol), 1,4-dioxane (1 mL), EtOH (0.5 mL), DIPEA (0.2 mL, 1 mmol), and [(1R,4S)-7,7-dimethyl-2-oxo-norbornan-1-yl]methanesulfonate (2S)-2-methylazetidin-1-ium salt (100 mg, 0.33 mmol). Heat the reaction in a microwave reactor at 150° C. for 2 h. Concentrate the reaction in-vacuo. Purify the residue by silica gel chromatography using a gradient of 40 to 50% EtOAc/hexanes to give the title compound (88 mg, 76%) as a light yellow solid. ES/MS (m/z): 392 (M+H).

Example 27

6-[1-(3-Hydroxy-4-piperidyl)pyrazol-4-yl]-2-[(2S)-2-methylazetidin-1-yl]-4-(trifluoromethyl)pyridine-3-carbonitrile

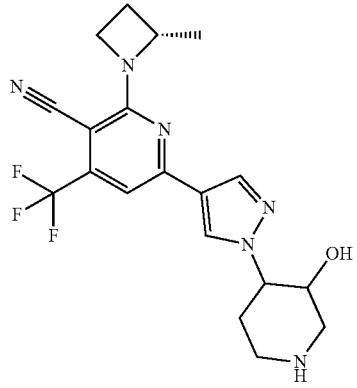 [SMILES: C[C@H]1CCN1c1nc(-c2cnn(C3CCNCC3O)c2)cc(C(F)(F)F)c1C#N]

Dissolve tert-butyl 4-[4-[5-cyano-6-[(2S)-2-methylazetidin-1-yl]-4-(trifluoromethyl)-2-pyridyl]pyrazol-1-yl]-3-hydroxy-piperidine-1-carboxylate (85 mg, 0.17 mmol) in DCM (1 mL), then add TFA (0.5 mL) and stir for 5 min. Concentrate the reaction in-vacuo. Purify the residue by reverse phase chromatography (C18, gradient 20 to 100% ACN/aqueous 10 mM ammonium carbonate+5% methanol) to give the title compound (27 mg, 40%) as a white solid. ES/MS (m/z): 407 (M+H).

Example 28

N-(2-Aminoethyl)-2-[4-[2-[(2S)-2-methylazetidin-1-yl]-6-(trifluoromethyl)pyrimidin-4-yl]pyrazol-1-yl]acetamide

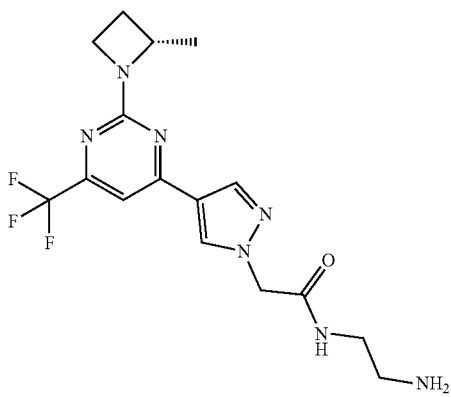 [SMILES: C[C@H]1CCN1c1nc(-c2cnn(CC(=O)NCCN)c2)cc(C(F)(F)F)n1]

Dissolve tert-butyl N-[2-[[2-[4-[2-[(2S)-2-methylazetidin-1-yl]-6-(trifluoromethyl)pyrimidin-4-yl]pyrazol-1-yl]acetyl]amino]ethyl]carbamate (340 mg) in neat TFA (5 mL) and stir at ambient temperature. After 2 min, quench with aqueous NaOH until basic. Extract with DCM and EtOAc. Combine the extracts, dry over sodium sulfate, filter, and concentrate. Purify the residue by preparative HPLC [parameters: solvents—10 mM aqueous ammonium bicarbonate pH 10/5% MeOH (Solvent A) and ACN (Solvent B); precolumn—Waters BEH HILIC 100×30 mm 5 μm, 110 Å with a 15×30 mm BEH HILIC guard column; column—Phenomenex® Kinetex® EVO C18, 100×30 mm, 5 μm, 100 Å with a 15×30 mm EVO guard column using an in-line heater at 50° C.; gradient 14 to 48% B] to give the title compound (45 mg, 17%). ES/MS (m/z): 384 (M+H).

Prepare the compounds shown in Table 5 using essentially the same procedure as Example 28 and the appropriate protected amine.

TABLE 5

| Example number | Name | Structure | ES/MS (m/z): (M + H) |
|---|---|---|---|
| 29 | 2-[4-[2-[(2S)-2-Methylazetidin-1-yl]-6-(trifluoromethyl)pyrimidin-4-yl]pyrazol-1-yl]-1-[(3S)-3-methylpiperazin-1-yl]ethanone | 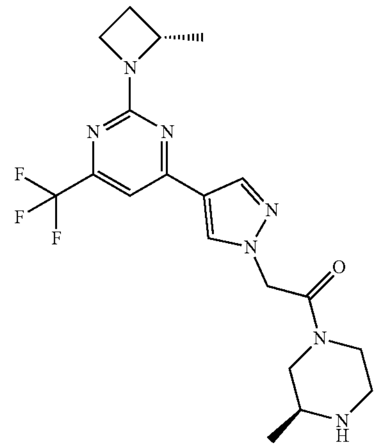 [SMILES: C[C@H]1CN(C(=O)Cn2cc(-c3cc(C(F)(F)F)nc(N4CC[C@@H]4C)n3)cn2)CCN1] | 424 |
| 30 | 2-[4-[2-[(2S)-2-Methylazetidin-1-yl]-6-(trifluoromethyl)pyrimidin-4-yl]pyrazol-1-yl]-1-[(2S)-2-methylpiperazin-1-yl]ethanone | 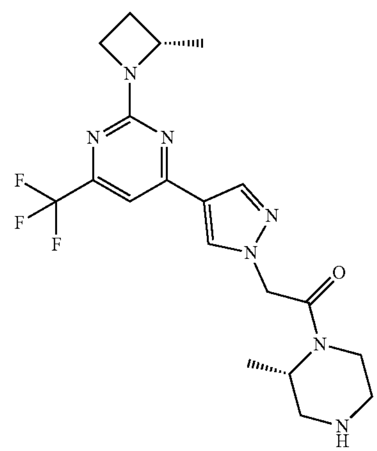 [SMILES: C[C@H]1CNCCN1C(=O)Cn1cc(-c2cc(C(F)(F)F)nc(N3CC[C@@H]3C)n2)cn1] | 424 |
| 31 | 1-(3,3-Dimethylpiperazin-1-yl)-2-[4-[2-[(2S)-2-methylazetidin-1-yl]-6-(trifluoromethyl)pyrimidin-4-yl]pyrazol-1-yl]ethanone | 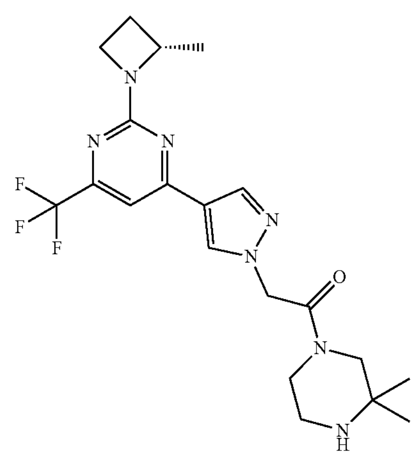 [SMILES: C[C@H]1CCN1c1nc(-c2cnn(CC(=O)N3CCNC(C)(C)C3)c2)cc(C(F)(F)F)n1] | 438 |

TABLE 5-continued

| Example number | Name | Structure | ES/MS (m/z): (M + H) |
|---|---|---|---|
| 32 | 1-[(2S,5R)-2,5-Dimethylpiperazin-1-yl]-2-[4-[2-[(2S)-2-methylazetidin-1-yl]-6-(trifluoromethyl)pyrimidin-4-yl]pyrazol-1-yl]ethanone | 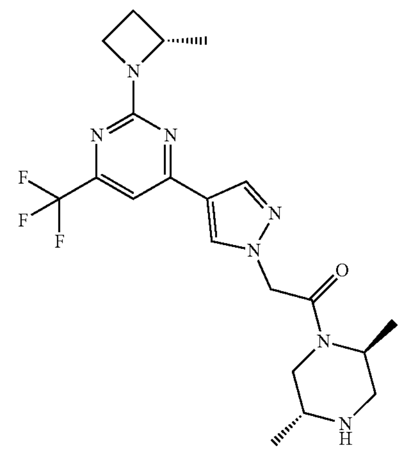 [SMILES: C[C@@H]1CN(C(=O)Cn2cc(-c3cc(C(F)(F)F)nc(N4CC[C@@H]4C)n3)cn2)[C@@H](C)CN1] | 438 |

Example 33

4-[1-(Azetidin-3-yl)pyrazol-4-yl]-2-[(2S)-2-methyl-azetidin-1-yl]-6-(trifluoromethyl)pyrimidine

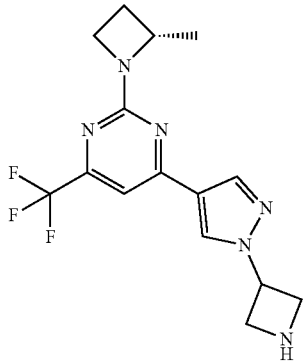 [SMILES: C[C@H]1CCN1c1nc(-c2cnn(C3CNC3)c2)cc(C(F)(F)F)n1]

Dissolve tert-butyl 3-[4-[2-[(2S)-2-methylazetidin-1-yl]-6-(trifluoromethyl)pyrimidin-4-yl]pyrazol-1-yl]azetidine-1-carboxylate (530 mg, 1.21 mmol) in DCM (50 mL). Add TFA (6 mL) and stir the mixture at RT for 1h. Concentrate the mixture in-vacuo to give the crude title compound. Purify half of this material by preparative HPLC [parameters: solvents—aqueous 10 mM ammonium bicarbonate pH 10/5% MeOH (Solvent A) and ACN (Solvent B); precolumn—Waters BEH HILIC 100×30 mm 5 μm, 110 Å with a 15×30 mm BEH HILIC guard column; column—Phenomenex® Kinetex® EVO C18, 100×30 mm, 5 μm, 100 Å with a 15×30 mm EVO guard column using in-line heater at 50° C.; gradient 23 to 58% B] to give the title compound (162 mg, 80% yield from half of the starting material) as a white solid. ES/MS (m/z): 339 (M+H).

Example 34

2-[(2S)-2-Methylazetidin-1-yl]-4-[1-(1-methylazetidin-3-yl)pyrazol-4-yl]-6-(trifluoromethyl)pyrimidine

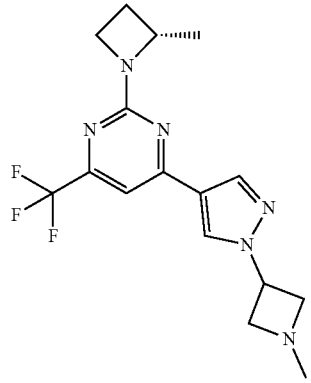 [SMILES: C[C@H]1CCN1c1nc(-c2cnn(C3CN(C)C3)c2)cc(C(F)(F)F)n1]

Dissolve half of the crude 4-[1-(azetidin-3-yl)pyrazol-4-yl]-2-[(2S)-2-methylazetidin-1-yl]-6-(trifluoromethyl)pyrimidine prepared in Example 33 (0.6 mmol) in MeOH (6 mL). Add acetic acid (0.1 mL) and 3.45 M aqueous formaldehyde (1 mL) and stir the mixture at RT for 30 min. Add sodium triacetoxyborohydride (300 mg, 1.4 mmol) and stir for the mixture 2 h. Concentrate the mixture in-vacuo and purify the residue by preparative HPLC [parameters: solvents—aqueous 10 mM ammonium bicarbonate pH 10/5% MeOH (Solvent A) and ACN (Solvent B); precolumn—Waters BEH HILIC 100×30 mm 5 μm, 110 Å with a 15×30 mm BEH HILIC guard column; column—Phenomenex® Kinetex® EVO C18, 100×30 mm, 5 μm, 100 with a 15×30 mm EVO guard column using inline heater at 50° C.; gradient 33-67% B] to give the title compound (128 mg, 61% yield from half of the starting material in Example 33) as a white solid. ES/MS (m/z): 353 (M+H).

Example 35

(2S,3R)-2-Methyl-1-[4-[1-(1-methylazetidin-3-yl)pyrazol-4-yl]-6-(trifluoromethyl)pyrimidin-2-yl]azetidin-3-ol

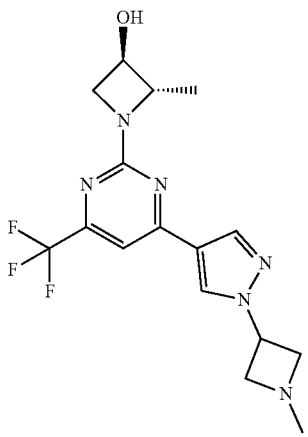 [SMILES: C[C@H]1[C@H](O)CN1c1nc(-c2cnn(C3CN(C)C3)c2)cc(C(F)(F)F)n1]

Prepare the title compound using essentially the same procedure as Example 34 beginning with (2S,3R)-1-[4-[1-(azetidin-3-yl)pyrazol-4-yl]-6-(trifluoromethyl)pyrimidin-2-yl]-2-methyl-azetidin-3-ol (Example 4). ES/MS (m/z): 369 (M+H), 367 (M–H).

Example 36

[(2R)-1-[4-[1-(1-Methylazetidin-3-yl)pyrazol-4-yl]-6-(trifluoromethyl)pyrimidin-2-yl]azetidin-2-yl]methanol

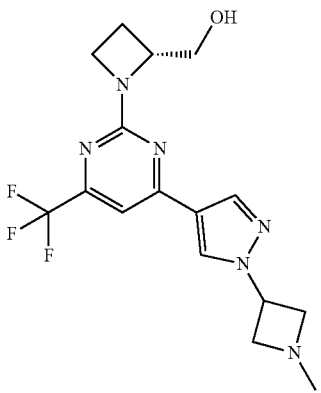 [SMILES: CN1CC(n2cc(-c3cc(C(F)(F)F)nc(N4CC[C@@H]4CO)n3)cn2)C1]

Prepare the title compound using essentially the same procedure as Example 34 beginning with [(2R)-1-[4-[1-(azetidin-3-yl)pyrazol-4-yl]-6-(trifluoromethyl)pyrimidin-2-yl]azetidin-2-yl]methanol (Example 3). ES/MS (m/z): 369 (M+H), 367 (M–H).

Assays

KHK Enzyme Activity Assay for Human KHK-C and Human KHK-A

The intrinsic potency for inhibition of KHK C or A activity may be measured using an enzymatic assay which measures the production of F1P. Compounds are prepared in DMSO and tested in a 10-point concentration curve, to create 3-fold serial dilutions of the compounds in a 96-well plate ranging from 20 µM to 1.02 nM. Enzyme is prepared in assay buffer [50 mM 4-(2-hydroxyethyl)piperazine-1-ethanesulfonic acid (HEPES), 10 mM potassium chloride, 100 mM magnesium chloride, 2 mM tris(2-carboxyethyl)phosphine (TCEP), 0.01% n-octyl glucoside] and incubated with compounds at RT for 15 min. The reaction is carried out in 100 µL volumes containing substrate concentrations of fructose (250 µM for KHK-C assay and 1.25 mM for KHK-A assay) and ATP (150 µM for both isoforms); which are further incubated at RT for 20 min. The reaction is then halted by the addition of stop buffer; consisting of 0.2% formic acid and 1 µg/ml $^{13}C_6$-fructose-6-phosphate ($^{13}C_6$-F6P) internal standard. Plates are stored in –20° C. until RapidFire MS analysis.

RapidFire MS Analysis for Quantitation of F1P

An Agilent 300 RapidFire automated extraction system (Agilent, Santa Clara, Calif.) with three HPLC quaternary pumps is coupled to an Agilent 6495 triple quadrupole mass spectrometer (Agilent Technologies, Santa Clara, Calif.) equipped with an electrospray ionization (ESI) interface source. The RapidFire Mass Spec system is equipped with a reusable RapidFire C18 (type C) solid-phase extraction (SPE) cartridge (G9205 Å).

Solvent A, used for sample loading and washing, is 6 mM octylamine (Acros Organics 129495000) brought to pH 5.0 using acetic acid. Solvent B, used for sample elution, is 20% water in ACN containing 0.1% formic acid. Samples are sequentially analyzed by aspirating 10 µL onto the collection loop under vacuum directly from multiwell plates. The 10 µL of sample is loaded onto the C18 cartridge and washed using solvent A at a flow rate of 1.25 mL/min for 5000 ms. The retained analytes are then eluted to the mass spectrometer using solvent B at a flow rate of 1.25 mL/min for 5000 ms. The system is re-equilibrated using solvent at flow rate of 1.25 mL/min for 2000 ms.

The triple quadrupole mass spectrometer is equipped with an ESI source and analytes are monitored using selected reaction monitoring (SRM) in negative mode [M–H]–. F1P is monitored at m/z 259.02/96.9 and $^{13}C_6$-fructose-6-phosphate is monitored at m/z 264.99/97. The area ratio values for F1P is calculated using $^{13}C_6$-fructose-6-phospate as internal standard.

The compounds of Examples 1 to 36 were tested essentially as described above:

TABLE 6

| Example Number | hKHK-C IC$_{50}$ (nM) | | hKHK-A IC$_{50}$ (nM) | |
|---|---|---|---|---|
| 1 | 20.7 ± 3.88 | (n = 4) | 24.2 ± 2.9 | (n = 4) |
| 2 | 134 ± 43.1 | (n = 7) | 98.2 ± 25.0 | (n = 7) |
| 3 | 41.9 ± 6.77 | (n = 3) | 45.4 ± 29.5 | (n = 4) |
| 4 | 14.4 ± 1.12 | (n = 3) | 11.4 ± 4.34 | (n = 4) |
| 5 | 57.0 ± 32.6 | (n = 5) | 37.7 ± 19.9 | (n = 5) |
| 6 | 25.7 ± 5.14 | (n = 2) | 15.4 ± 5.05 | (n = 3) |
| 7 | 18.1 ± 4.85 | (n = 2) | 6.02 ± 2.27 | (n = 3) |
| 8 | 56.1 ± 62.5 | (n = 3) | 25.2 ± 15.7 | (n = 3) |
| 9 | 6.26 | (n = 1) | 3.58 | (n = 1) |
| 10 | 418 ± 503 | (n = 3) | 246 ± 248 | (n = 3) |
| 11 | 8.03 | (n = 1) | 5.23 | (n = 1) |
| 12 | 3.87 ± 0.391 | (n = 4) | 3.65 ± 0.817 | (n = 4) |
| 13 | 15.5 ± 20.4 | (n = 3) | 7.69 ± 7.97 | (n = 3) |
| 14 | 15.9 ± 4.37 | (n = 2) | 19.1 ± 2.98 | (n = 3) |
| 15 | 27.2 ± 8.60 | (n = 2) | 26.7 ± 3.66 | (n = 3) |
| 16 | 28.0 ± 17.3 | (n = 2) | 30.0 ± 5.09 | (n = 3) |
| 17 | 16.1 ± 7.96 | (n = 4) | 13.2 ± 12.7 | (n = 4) |

TABLE 6-continued

| Example Number | hKHK-C IC$_{50}$ (nM) | | hKHK-A IC$_{50}$ (nM) | |
|---|---|---|---|---|
| 18 | 59.2 ± 67.8 | (n = 3) | 35.6 ± 32.4 | (n = 3) |
| 19 | 54.3 | (n = 1) | 29.2 | (n = 1) |
| 20 | 150 ± 243 | (n = 3) | 81.8 ± 92.6 | (n = 3) |
| 21 | 55.2 ± 28.1 | (n = 3) | 39.2 ± 13.6 | (n = 3) |
| 22 | 61.3 ± 57.5 | (n = 3) | 33.7 ± 17.8 | (n = 3) |
| 23 | 41.6 ± 47.1 | (n = 3) | 24.9 ± 15.3 | (n = 3) |
| 24 | 7.91 | (n = 1) | 7.29 | (n = 1) |
| 24a | 6.06 | (n = 1) | 9.99 | (n = 1) |
| 24b | 4.89 | (n = 1) | 6.75 | (n = 1) |
| 25 | 13.6 ± 7.2 | (n = 4) | 16.9 ± 9.7 | (n = 4) |
| 26 | 28.4 | (n = 1) | 22.2 | (n = 1) |
| 27 | 9.21 | (n = 1) | 4.63 | (n = 1) |
| 28 | 68.0 | (n = 1) | 51.0 | (n = 1) |
| 29 | 38.6 | (n = 1) | 103 | (n = 1) |
| 30 | 46.3 | (n = 1) | 57.8 | (n = 1) |
| 31 | 34.7 | (n = 1) | 70.5 | (n = 1) |
| 32 | 13.3 | (n = 1) | 41.5 | (n = 1) |
| 33 | 4.90 ± 1.31 | (n = 2) | 3.63 ± 1.13 | (n = 3) |
| 34 | 3.71 ± 0.178 | (n = 2) | 5.41 ± 6.13 | (n = 3) |
| 35 | 2.63 | (n = 1) | 1.59 | (n = 1) |
| 36 | 10.0 | (n = 1) | 3.98 | (n = 1) |

Data expressed as average ± SEM (n)

The results as shown in Table 6 above demonstrate that the compounds of Examples 1 to 36 inhibit the enzymatic activity of both KHK-C and KHK-A KHK Cellular Activity Assay Potency can be measured using a cellular assay for the inhibition of conversion of Fructose to F1P by cellular KHK. HepG2 liver cells are plated on 96-well cell culture plates in growth media [Dulbecco's Modified Eagle's medium (DMEM) high glucose, 10% heat-inactivated fetal bovine serum (HI FBS), 1× Penicillin/streptomycin] and allowed to attach overnight in a 37° C. incubator. The growth media is washed and replaced with assay media consisting of Gibco OptiMEM 1 Reduced Serum Medium, 0.1% Casein, 8.33 mM D-Fructose-$^{13}C_6$, and compound concentrations ranging from 100 μM to 0.0051 μM (10-point concentration curve). Plates are incubated at 37° C. for 3 h, after which assay media is aspirated from the cell wells. Stop solution consisting of 80% MeOH, 2 mM ammonium acetate, and 50 ng/mL fructose-6-phosphate-$^{13}$C6 is then added to the cells. Plates are stored in −20° C. until RapidFire MS analysis (described above).

The compounds of Examples 1 to 36 were tested essentially as described above:

TABLE 7

| Example Number | HepG2 IC50 |
|---|---|
| 1 | 41.1 ± 8.13 (n = 3) |
| 2 | 98.4 ± 8.69 (n = 3) |
| 3 | 40.2 ± 10.9 (n = 4) |
| 4 | 16.8 ± 4.97 (n = 4) |
| 5 | 83.6 ± 8.16 (n = 3) |
| 6 | 22.9 ± 5.15 (n = 3) |
| 7 | 8.06 ± 1.41 (n = 3) |
| 8 | 20.4 ± 8.09 (n = 3) |
| 9 | 15.0 (n = 1) |
| 10 | 118 ± 24.2 (n = 3) |
| 11 | 48.4 (n = 1) |
| 12 | 5.36 ± 0.0912 (n = 3) |
| 13 | 26.2 ± 4.30 (n = 3) |
| 14 | 34.9 ± 8.26 (n = 3) |
| 15 | 52.7 ± 3.08 (n = 3) |
| 16 | 73.2 ± 14.9 (n = 3) |
| 17 | 1.66 ± 0.435 (n = 3) |
| 18 | 16.3 ± 1.84 (n = 3) |
| 19 | 95.9 (n = 1) |
| 20 | 35.7 ± 3.47 (n = 3) |
| 21 | 102 ± 5.47 (n = 3) |
| 22 | 109 ± 9.69 (n = 3) |
| 23 | 76.2 ± 7.07 (n = 3) |
| 24 | 27.0 (n = 1) |
| 24a | 18.2 (n = 1) |
| 24b | 27.2 (n = 1) |
| 25 | 33.5 ± 9.07 (n = 3) |
| 26 | 81.6 (n = 1) |
| 27 | 6.93 (n = 1) |
| 28 | 144 (n = 1) |
| 29 | 145 (n = 1) |
| 30 | 143 (n = 1) |
| 31 | 119 (n = 1) |
| 32 | 62.9 (n = 1) |
| 33 | 6.13 ± 0.528 (n = 3) |
| 34 | 2.93 ± 0.156 (n = 3) |
| 35 | 6.41 (n = 1) |
| 36 | 13.4 (n = 1) |

Data expressed as average ± SEM (n)

The results as shown in Table 7 above demonstrate that the compounds of Examples 1 to 36 inhibit the metabolism of fructose to F1P in HepG2 cells. Liquid Chromatography with Tandem Mass Spectrometry (LC-MS/MS) Method for Pharmacokinetic Assays: Samples are extracted using a protein precipitation by adding 180 μL of MeOH:ACN (1:1, v/v) containing an internal standard to 50 μL of plasma. Samples are then diluted with MeOH:Water (1:1, v/v) to get concentrations within standard curve range. Diluted samples are analyzed by LC-MS/MS using a Sciex API 4000 triple quadrupole mass spectrometer (Applied Biosystems/MDS; Foster City, Calif.) equipped with a TurboIonSpray interface, and operated in positive ion mode. The analytes are chromatographically separated using a ECHELON C18 4 um 20×2.1 mm column. LC conditions are Water/1 M ammonium bicarbonate, (2000:10, v/v) (Mobile Phase A), and MeOH/1 M ammonium bicarbonate, (2000:10, v/v) (Mobile Phase B).

Pharmacokinetics in Sprague Dawley Rats

The in vivo pharmacokinetic properties of Example 1 and Example 2 are demonstrated using Sprague Dawley Rats (fasted; n=3/dose route). The compound is administered by a single oral (PO; 2 or 3 mg/kg; volume of 10 mL/kg) or intravenous (IV; 1 mg/kg; volume of 1 mL/kg) dose in vehicle. Blood is collected from each animal at multiple time points between 0 and up to 48 hours post-dosage. The plasma concentrations of Example 1 and Example 2 are determined by a LC-MS/MS method as described above.

For Example 1, the mean half-life is 12.9 hours and bioavailability is 83% as determined by PO dosing, while IV dosing revealed mean half-life is 12.8 hours and the mean clearance is 5.86 mL/min/kg. For Example 2, the mean half-life is 5.12 hours and bioavailability is 95% as determined by PO dosing, while IV dosing revealed mean half-life is 4.29 hours and the mean clearance is 56.4 mL/min/kg. This data shows Examples 1 and 2 have differing levels of clearance, yet both have high oral bioavailability and prolonged elimination evidenced by adequate mean half-life.

Pharmacokinetics in Dogs

The in vivo pharmacokinetic properties of Example 1 and Example 2 are demonstrated using Beagle Dogs (fed, n=3). The compound is administered by a single oral (PO; 2 or 3 mg/kg; volume of 2 mL/kg) or intravenous (IV; 1 mg/kg; volume of 1 mL/kg) dose in vehicle. Blood is collected from each animal at multiple time points between 0 and up to 72 hours post-dosage. The plasma concentrations of Example 1 and Example 2 are determined by a LC-MS/MS method as described above.

For Example 1, the mean half-life is 36.6 hours and bioavailability is 87% as determined by PO dosing, while IV dosing revealed mean half-life is 28 hours and the mean clearance is 3.41 mL/min/kg. For Example 2, the mean half-life is 9.79 hours and bioavailability is ~100% as determined by PO dosing, while IV dosing revealed mean half-life is 10.3 hours and the mean clearance is 19.6 mL/min/kg. This data shows Examples 1 and 2 have differing levels of clearance, yet both have high oral bioavailability and prolonged elimination evidenced by adequate mean half-life.

The invention claimed is:

1. A compound of the formula:

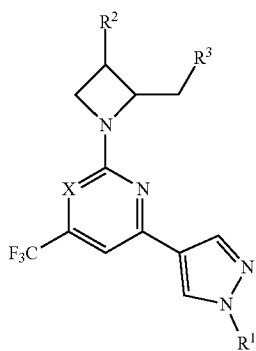

wherein
X is N, or C substituted with CN;
$R^1$ is selected from: H,

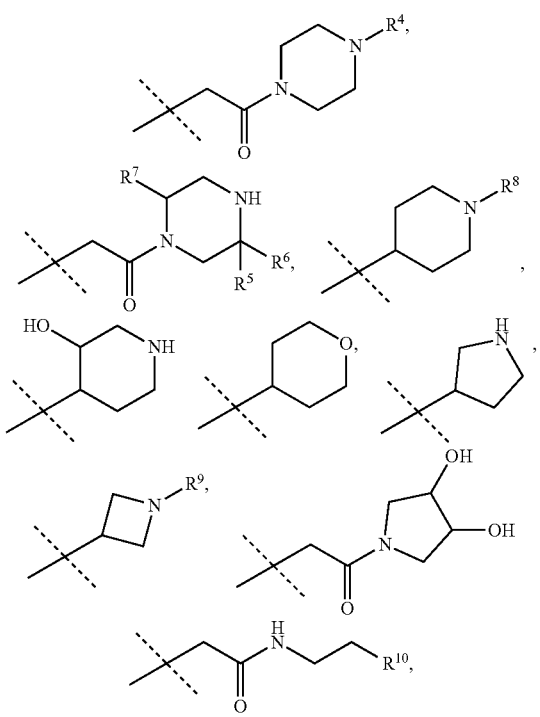

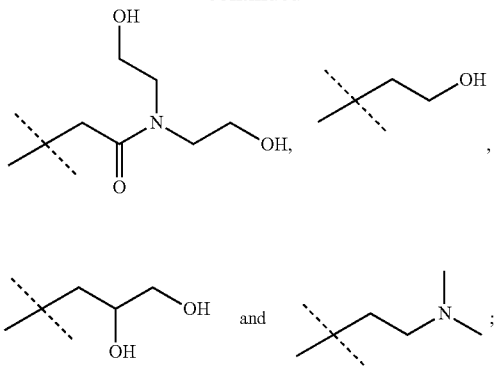

$R^2$ and $R^3$ are both H, or one is H and the other is OH;
$R^4$, $R^5$, $R^6$, $R^7$ and $R^9$ are independently H or $CH_3$;
$R^8$ is H, $CH_3$, $CH_2CH_2OH$, $C(=O)CH_2NH_2$, or $C(=O)CH_3$; and
$R^{10}$ is OH or $NH_2$;

or a pharmaceutically acceptable salt thereof.

2. The compound according to claim 1, wherein $R^1$ is selected from:

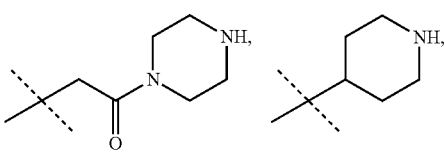

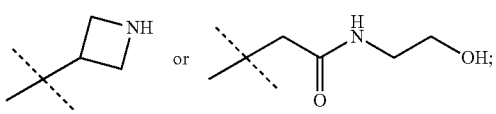

or a pharmaceutically acceptable salt thereof.

3. The compound according to claim 1, wherein the compound is:

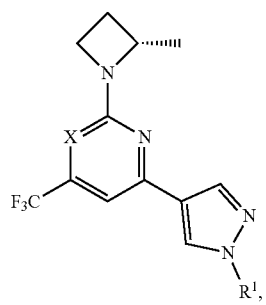

or a pharmaceutically acceptable salt thereof.

4. The compound according to claim 1, wherein X is N, or a pharmaceutically acceptable salt thereof.

5. The compound according to claim 1, wherein X is C substituted with CN, or a pharmaceutically acceptable salt thereof.

6. The compound according to claim 1, wherein the compound is:

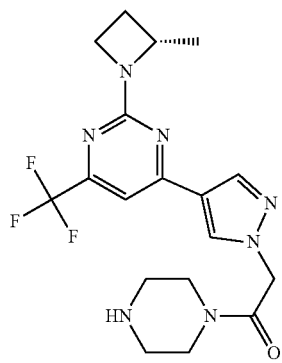 [SMILES: C[C@H]1CCN1c1nc(-c2cnn(CC(=O)N3CCNCC3)c2)cc(C(F)(F)F)n1]

or a pharmaceutically acceptable salt thereof.

7. The compound, or pharmaceutically acceptable salt thereof, according to claim 6, which is a succinate salt.

8. A method of treating type 2 diabetes mellitus in a patient, comprising administering to a patient in need of such treatment an effective amount of a compound of claim 1, or a pharmaceutically acceptable salt thereof.

9. A method of treating heart failure in a patient, comprising administering to a patient in need of such treatment an effective amount of a compound of claim 1, or a pharmaceutically acceptable salt thereof.

10. A method of treating diabetic kidney disease in a patient, comprising administering to a patient in need of such treatment an effective amount of a compound of claim 1, or a pharmaceutically acceptable salt thereof.

11. A method of treating non-alcoholic steatohepatitis in a patient, comprising administering to a patient in need of such treatment an effective amount of a compound of claim 1, or a pharmaceutically acceptable salt thereof.

12. A method of treating type 2 diabetes mellitus in a patient, comprising administering to a patient in need of such treatment an effective amount of a compound of claim 6, or a pharmaceutically acceptable salt thereof.

13. A method of treating heart failure in a patient, comprising administering to a patient in need of such treatment an effective amount of a compound of claim 6, or a pharmaceutically acceptable salt thereof.

14. A method of treating diabetic kidney disease in a patient, comprising administering to a patient in need of such treatment an effective amount of a compound of claim 6, or a pharmaceutically acceptable salt thereof.

15. A method of treating non-alcoholic steatohepatitis in a patient, comprising administering to a patient in need of such treatment an effective amount of a compound of claim 6, or a pharmaceutically acceptable salt thereof.

16. A pharmaceutical composition, comprising a compound, or a pharmaceutically acceptable salt thereof, according to claim 1 with one or more pharmaceutically acceptable carriers, diluents, or excipients.

17. A process for preparing a pharmaceutical composition, comprising admixing a compound, or a pharmaceutically acceptable salt thereof, according to claim 1 with one or more pharmaceutically acceptable carriers, diluents, or excipients.

* * * * *

UNITED STATES PATENT AND TRADEMARK OFFICE
CERTIFICATE OF CORRECTION

Page 1 of 2

PATENT NO. : 11,124,500 B2
APPLICATION NO. : 16/902806
DATED : September 21, 2021
INVENTOR(S) : Coates et al.

It is certified that error appears in the above-identified patent and that said Letters Patent is hereby corrected as shown below:

On the Title Page

Column 2, item (56) Line 26: Delete "o" and insert -- of --, therefor.
Column 2, item (56) Line 28: Delete "Softie," and insert -- Softic, --, therefor.
Column 2, item (56) Line 29: Delete "I." and insert -- T. --, therefor.
Column 2, Line 1: Delete "I" and insert -- I: --, therefor.

In the Claims

Column 75, Line 51-54 (approx.): In Claim 1, delete " 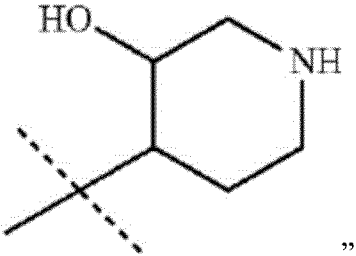 "

and insert -- 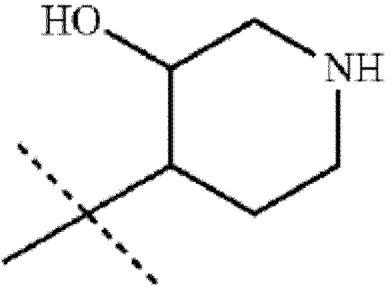 , --, therefor.

Signed and Sealed this
Seventeenth Day of May, 2022

Katherine Kelly Vidal
*Director of the United States Patent and Trademark Office*

CERTIFICATE OF CORRECTION (continued)
U.S. Pat. No. 11,124,500 B2

In Column 75, Lines 56-63 (approx.), In Claim 1, delete "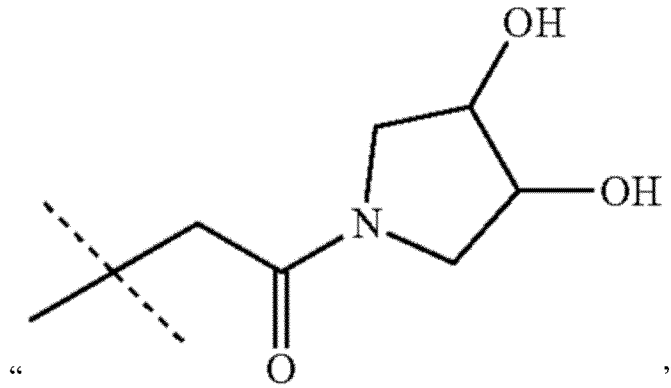" and insert -- 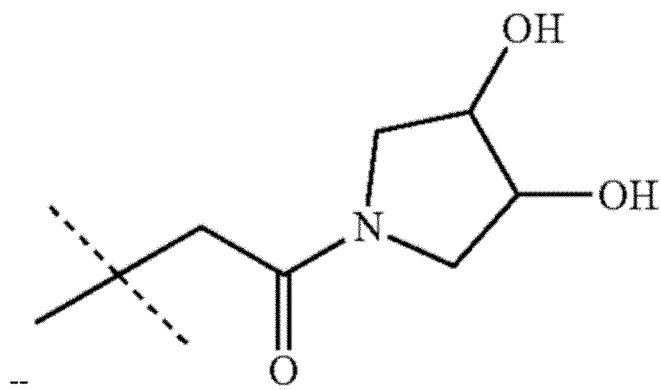 , --, therefor.

In Column 76, Lines 11-15 (approx.), In Claim 1, delete " 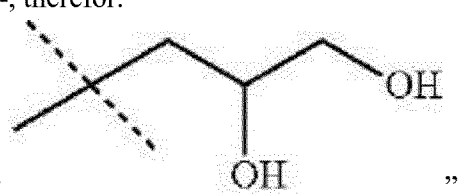 "

and insert -- 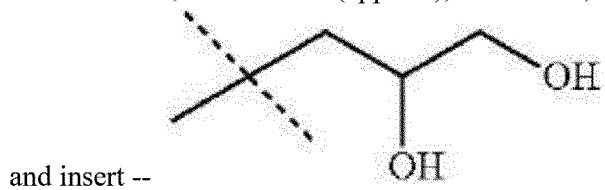 , --, therefor.

In Column 76, Lines 36-40 (approx.), In Claim 2, delete " 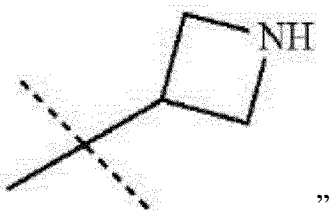 "

and insert -- 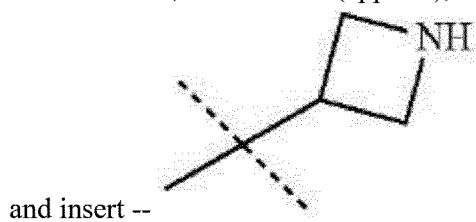 , --, therefor.